United States Patent
Tanaka et al.

(10) Patent No.: US 8,517,917 B2
(45) Date of Patent: Aug. 27, 2013

(54) CAPSULE MEDICAL APPARATUS

(75) Inventors: Shinsuke Tanaka, Hino (JP); Hironobu Takizawa, Hino (JP); Hironao Kawano, Machida (JP); Masaki Takahashi, Hachoji (JP)

(73) Assignee: Olympus Medical Systems Corp., Tokyo (JP)

( * ) Notice: Subject to any disclaimer, the term of this patent is extended or adjusted under 35 U.S.C. 154(b) by 657 days.

(21) Appl. No.: 12/435,121

(22) Filed: May 4, 2009

(65) Prior Publication Data

US 2009/0306473 A1     Dec. 10, 2009

(30) Foreign Application Priority Data

Jun. 4, 2008 (JP) ................................ 2008-147321
Jun. 4, 2008 (JP) ................................ 2008-147322

(51) Int. Cl.
| A61B 1/00 | (2006.01) |
| A61B 1/04 | (2006.01) |
| A61B 6/00 | (2006.01) |
| A61M 31/00 | (2006.01) |
| A61M 37/00 | (2006.01) |

(52) U.S. Cl.
USPC ........... 600/106; 600/118; 600/432; 604/506; 604/131

(58) Field of Classification Search
USPC ................ 600/106, 118, 109, 424, 160, 321, 600/407, 181, 432; 424/457; 604/274, 272, 604/266, 264, 506, 117, 198, 192, 131, 134, 604/132, 139, 156, 30; 425/149; 239/96
See application file for complete search history.

(56) References Cited

U.S. PATENT DOCUMENTS

| 4,147,165 A * | 4/1979 | Tauschinski .................. 604/161 |
| 4,890,621 A | 1/1990 | Hakky |
| 4,967,762 A * | 11/1990 | DeVries ......................... 600/566 |
| 5,702,367 A * | 12/1997 | Cover et al. .................... 604/110 |
| 5,853,390 A * | 12/1998 | Freschi .......................... 604/110 |
| 6,843,783 B2 * | 1/2005 | Ooyauchi ...................... 604/239 |
| 2003/0167053 A1 * | 9/2003 | Taufig ............................ 604/542 |
| 2004/0186422 A1 | 9/2004 | Rioux et al. |
| 2005/0148847 A1 * | 7/2005 | Uchiyama et al. ............. 600/407 |
| 2008/0154254 A1 * | 6/2008 | Burger et al. .................... 606/23 |

FOREIGN PATENT DOCUMENTS

| CN | 2603657 Y | 2/2004 |
| EP | 1 970 094 A1 | 9/2008 |
| JP | 07-088114 | 4/1995 |
| JP | 07-313513 | 12/1995 |

(Continued)

OTHER PUBLICATIONS

Extended European Search Report dated Sep. 8, 2010.

(Continued)

Primary Examiner — John P Leubecker
Assistant Examiner — Ronald D Colque
(74) Attorney, Agent, or Firm — Scully, Scott, Murphy & Presser, P.C.

(57) ABSTRACT

A capsule medical apparatus includes a needle driving unit that punctures an internal region of a subject with an injection needle and pulls out the injection needle from the internal region, a liquid injection unit that injects a liquid into the internal region through the injection needle, and a leak prevention unit that prevents the liquid that is injected into the internal region from leaking from the internal region.

5 Claims, 39 Drawing Sheets

(STATE A14)

(STATE A15)

(56) References Cited

FOREIGN PATENT DOCUMENTS

| JP | 08-117335 | 5/1996 |
| JP | 08-252925 | 10/1996 |
| JP | 11-114059 A | 4/1999 |
| JP | 11-114060 A | 4/1999 |
| JP | 11-318925 A | 11/1999 |
| JP | 2001-516608 | 10/2001 |
| JP | 2002-530162 | 9/2002 |
| JP | 2003-093332 | 4/2003 |
| JP | 2003-530897 | 10/2003 |
| JP | 2003-325438 A | 11/2003 |
| JP | 2004-041709 | 2/2004 |
| JP | 2004-222998 A | 8/2004 |
| JP | 2006-043115 | 2/2006 |
| JP | 2007-151913 A | 6/2007 |
| JP | 2007-260241 A | 10/2007 |
| WO | WO 99/13779 | 3/1999 |
| WO | WO 00/30705 | 6/2000 |
| WO | WO 00/67655 | 11/2000 |
| WO | WO 2007/037164 A1 | 4/2007 |
| WO | WO 2007/069697 A1 | 6/2007 |

OTHER PUBLICATIONS

Notice of Rejection dated Oct. 30, 2012 from corresponding Japanese Patent Application No. 2008-147321 together with an English language translation.
Decision of a Patent Grant dated Dec. 11, 2012 from corresponding Japanese Patent Application No. 2008-147322 together with an English language translation.
Chinese Office Action dated Aug. 3, 2012 from related Chinese Application No. CN 201110187724.8.

\* cited by examiner

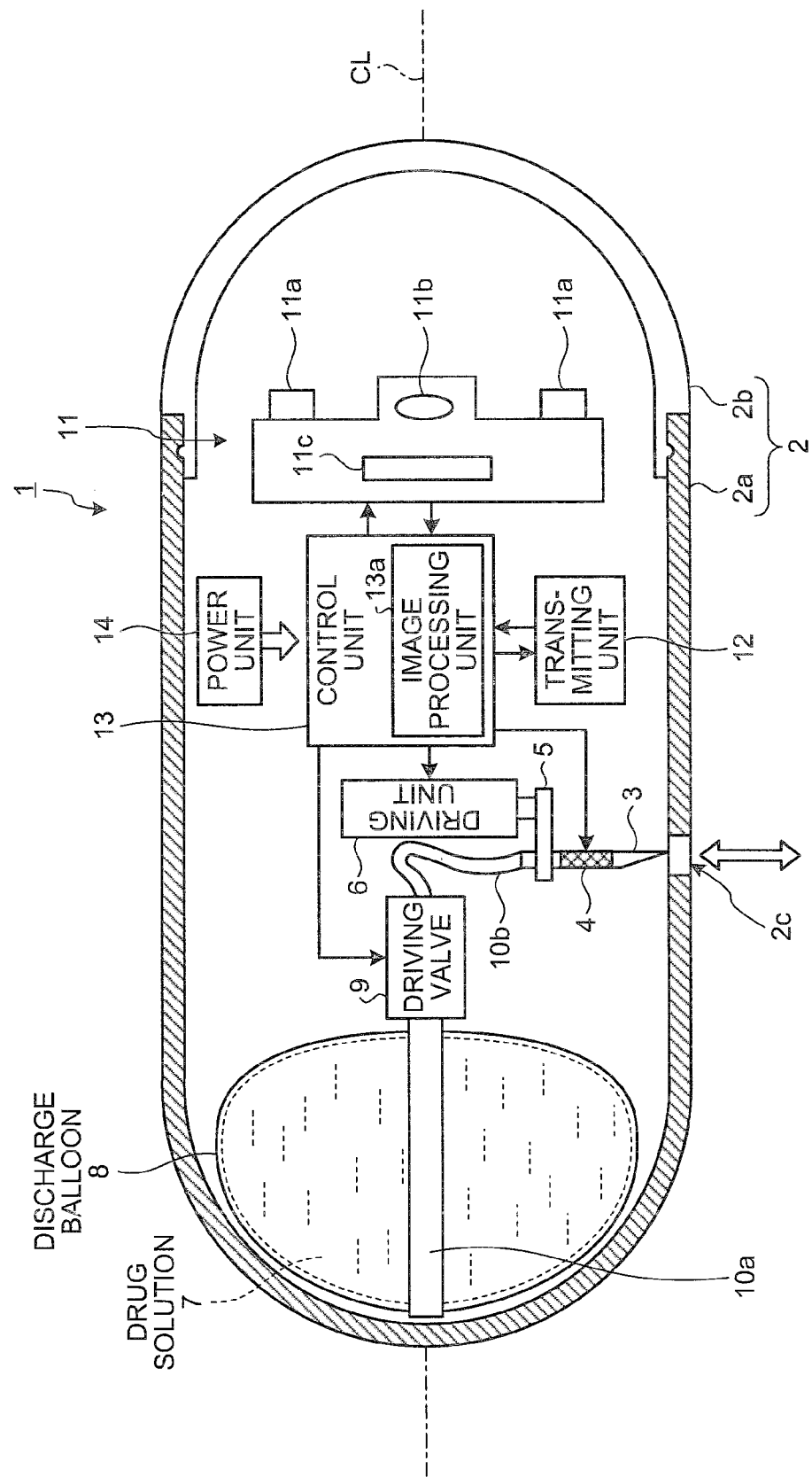

(STATE A1)

(STATE A2)

(STATE A3)

(STATE A4)

(STATE A5)

(STATE A6)

(STATE A7)

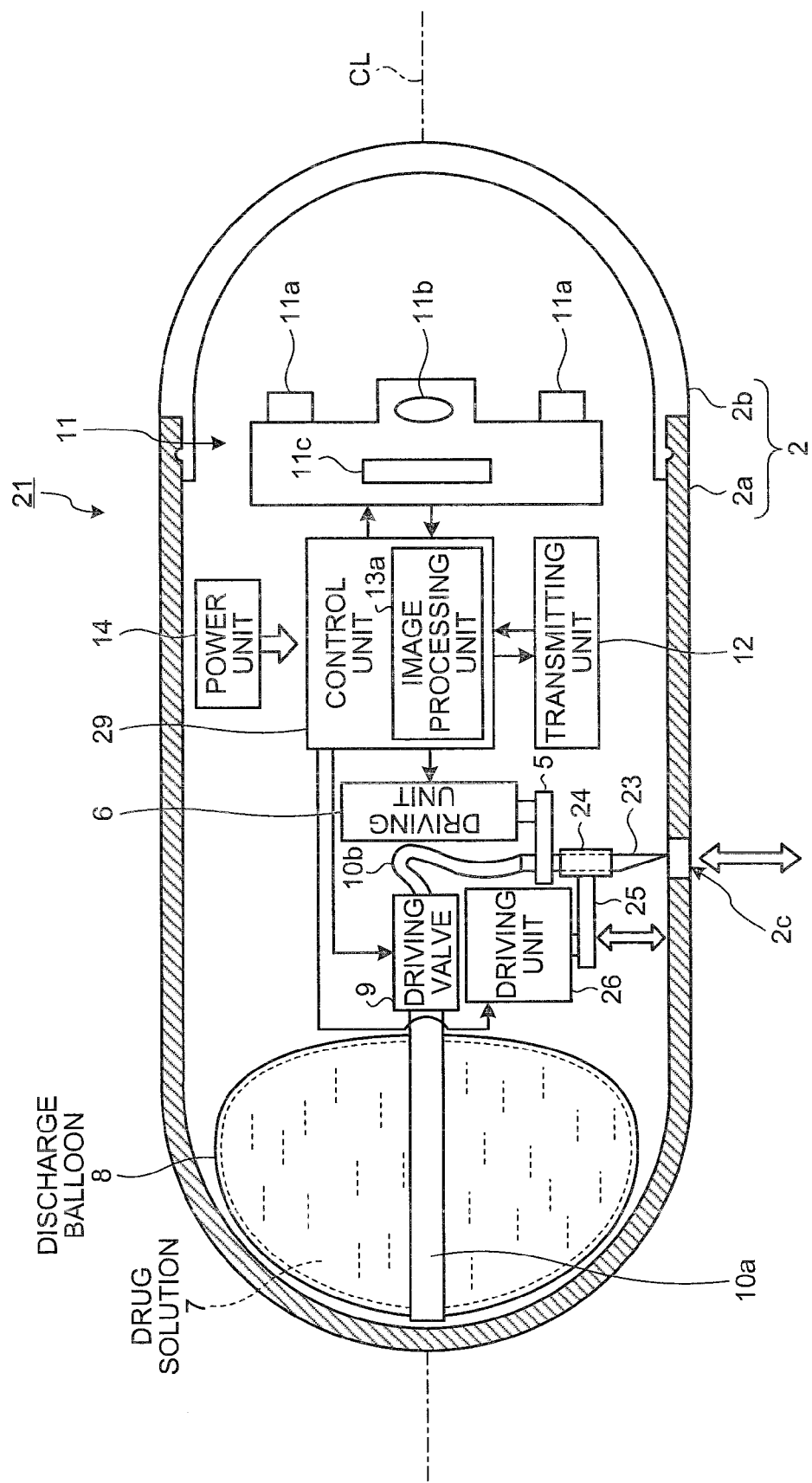

(STATE B3)

(STATE B4)

(STATE B5)

(STATE B6)

(PUNCTURING)

(DRUG SOLUTION 7)

(PULLING OUT)

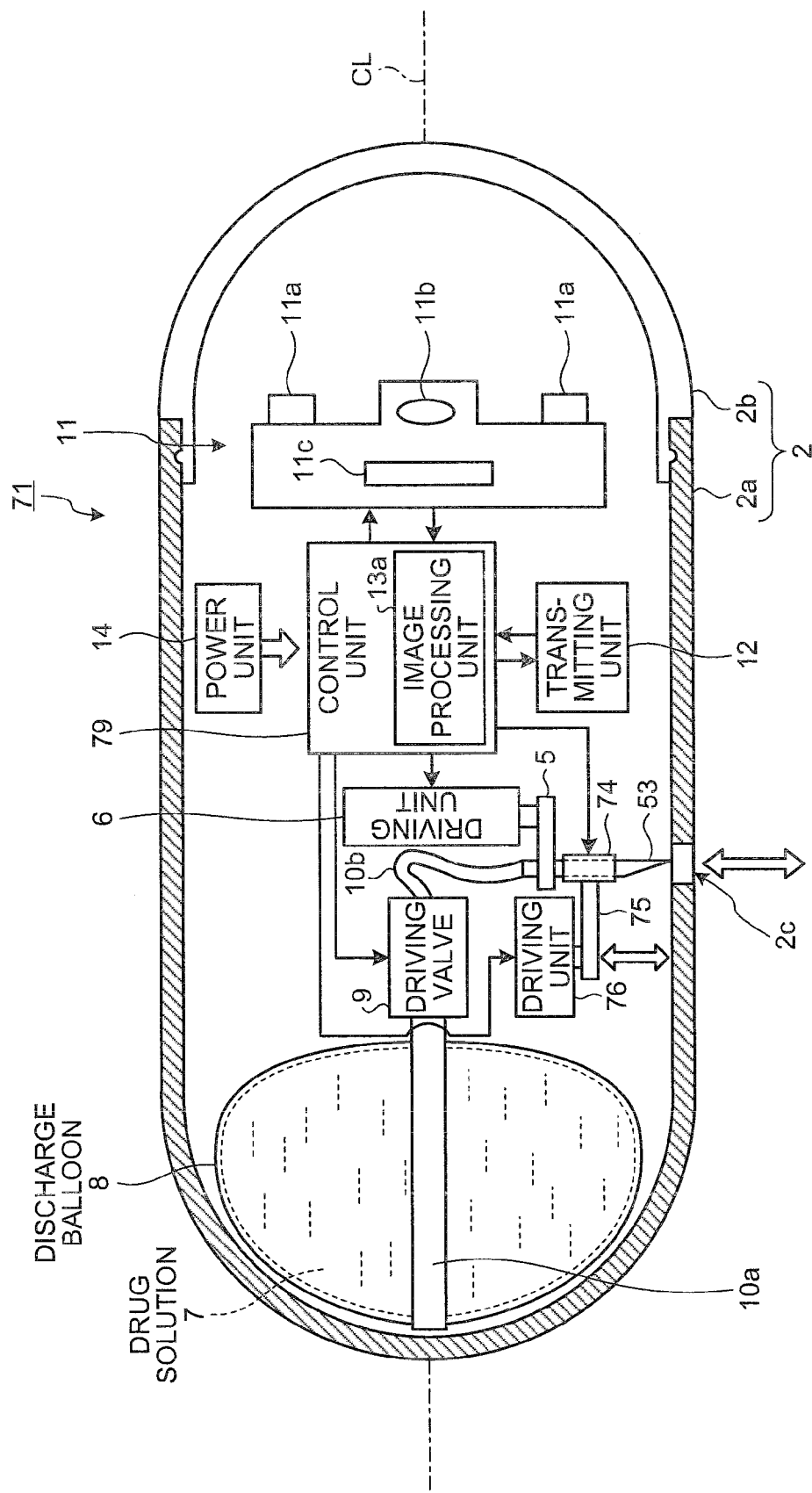

(PUNCTURING)

(PULLED OUT)

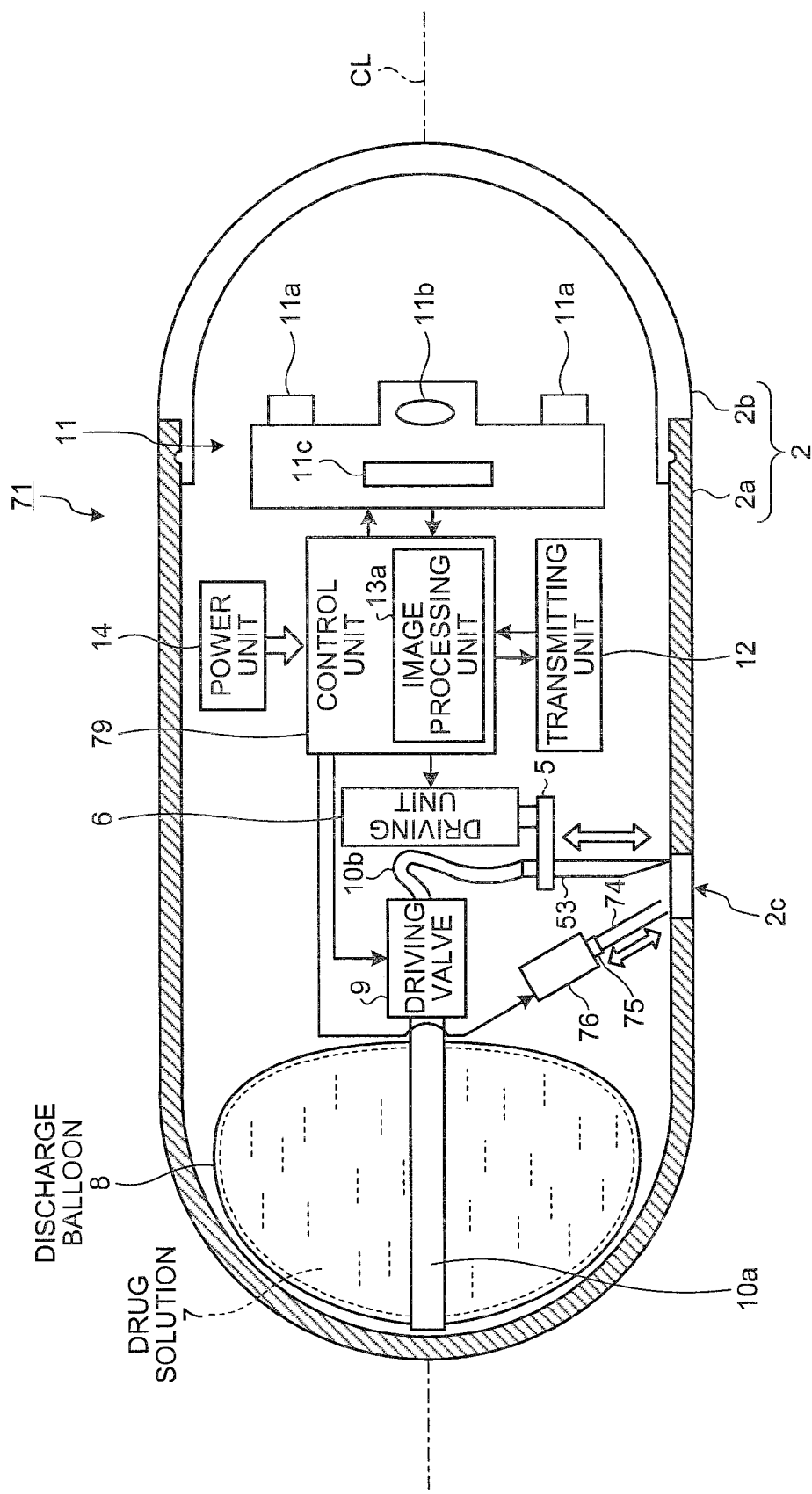

(STATE A11)

(STATE A12)

(STATE A13)

(STATE A14)

(STATE A15)

(STATE A16)

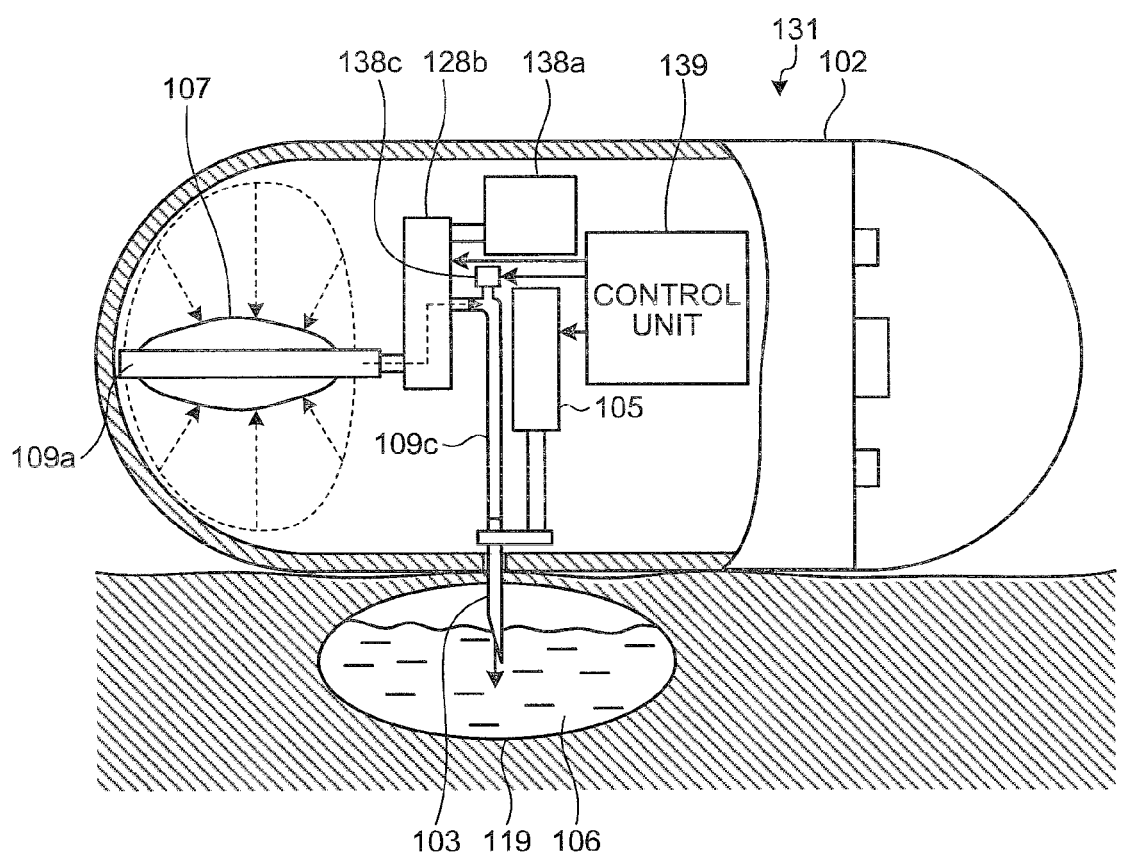

CAPSULE MEDICAL APPARATUS

CROSS-REFERENCE TO RELATED APPLICATIONS

This application is based upon and claims the benefit of priority from Japanese Patent Application Nos. 2008-147321 and 2008-147322, both filed Jun. 4, 2008, the entire contents of which are incorporated herein by reference.

BACKGROUND OF THE INVENTION

1. Field of the Invention

The present invention relates to a capsule medical apparatus that is introduced into a subject and has a local injection function. The local injection function is for injecting a liquid, e.g., a drug solution, into a desired region inside the subject.

2. Description of the Related Art

In conventional endoscopy technology, capsule medical apparatuses that are introduced into organs of a subject and capture images of the inside of the organs (hereinafter, "in-vivo images") have been proposed. Such capsule medical apparatuses have imaging and wireless transmission functions therein. The capsule medical apparatus is swallowed by a subject, e.g., a patient, and sequentially captures in-vivo images of the subject while moving through the digestive tracts due to peristalsis or the like. Each time the capsule medical apparatus captures an in-vivo image of the subject, the capsule medical apparatus wirelessly transmits the in-vivo image in sequence to a receiving apparatus, which is located outside the subject. The capsule medical apparatus introduced into the subject is later excreted.

Some capsule medical apparatuses have been proposed that have not only the above functions but also a local injection function for injecting a drug solution into an internal region of a subject (e.g., Japanese Patent Application Laid-Open Nos. 2006-43115 and 2004-41709). The capsule medical apparatus disclosed in Japanese Patent Application Laid-Open Nos. 2006-43115 and 2004-41709 punctures an internal region of a subject with an injection needle and injects a drug solution into the internal region using the injection needle that punctures the internal region. Then, the capsule medical apparatus pulls out the injection needle that punctures the internal region and stores the injection needle in the capsule medical apparatus.

A method for injecting medicines into tissue has been proposed (e.g. Japanese translation No. 2003-530897 of PCT international application). In this method, an injecting apparatus injects a drug solution into tissue and then pulls out an injection needle from the tissue. The injection apparatus cauterizes and hardens a region of the tissue where the injection has been performed, i.e., an injection region, by high frequency cauterization or laser heating to seal the site of the injection in the injection region.

SUMMARY OF THE INVENTION

A capsule medical apparatus according to one aspect of the present invention includes: a needle driving unit that punctures an internal region of interest in a subject with an injection needle and pulls out the injection needle from the internal region of interest; a liquid injection unit that injects a liquid into the internal region of interest through the injection needle that punctures the internal region of interest; and a leak prevention unit that prevents the liquid that is injected into the internal region of interest from leaking from the internal region of interest.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 1 is a schematic diagram of an exemplary configuration of a capsule medical apparatus according to a first embodiment of the present invention;

FIG. 6 is a schematic diagram of an exemplary configuration of a capsule medical apparatus according to a second embodiment of the present invention;

FIG. 19 is a schematic diagram of an exemplary configuration of a capsule medical apparatus according to a second variation of the fourth embodiment of the present invention;

FIG. 24 is a schematic diagram of another aspect of the capsule medical apparatus according to the second variation of the fourth embodiment of the present invention;

FIG. 39 is a schematic diagram in which the capsule medical apparatus inside the subject injects a drug solution into the affected area after discharging the gas.

DETAILED DESCRIPTION OF THE PREFERRED EMBODIMENTS

Figure 2A:
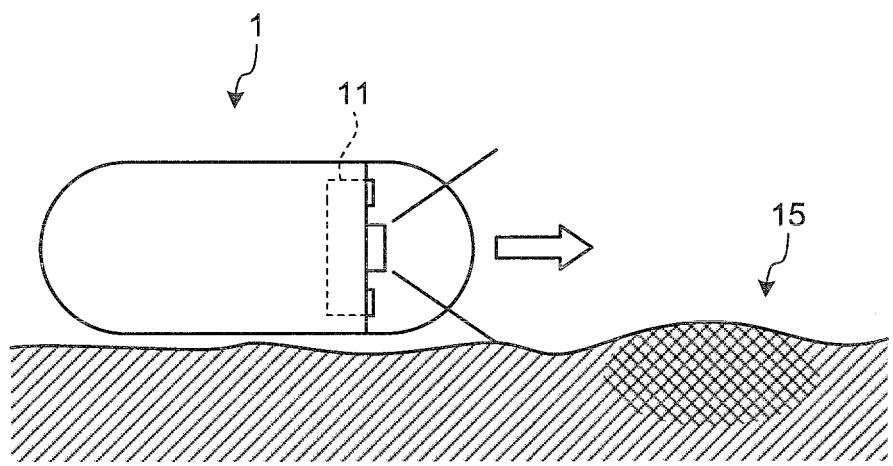
FIGS. 2A and 2B are schematic diagrams in which the capsule medical apparatus inside the subject approaches (FIG. 2A) and reaches (FIG. 2B) an affected area.

Exemplary embodiments of a capsule medical apparatus according to the present invention are described in detail below with reference to the accompanying drawings. An example of such a capsule medical apparatus is described. The capsule medical apparatus injects a drug solution into an internal region of interest, e.g., an affected area, inside a subject. The embodiments do not limit the scope of the present invention.

FIG. 1 is a schematic diagram of an exemplary configuration of a capsule medical apparatus according to a first embodiment of the present invention. As shown in FIG. 1, a capsule medical apparatus 1 according to the first embodiment includes a capsule casing 2, an injection needle 3, a heater 4, a supporter 5, and a driving unit 6. The capsule casing 2 consists of a cylinder-shaped container 2a and a dome-shaped container 2b. The injection needle 3 punctures an internal region of a subject. The heater 4 heats the injection needle 3 so that the injection needle 3 contracts. The supporter 5 supports the injection needle 3. The driving unit 6 drives the injection needle 3 so that the injection needle 3 protrudes from the capsule casing 2. The capsule medical apparatus 1 further includes a discharge balloon 8 that injects a drug solution 7 into an internal region through the injection needle 3, a driving valve 9 that switches the state between the discharge balloon 8 and the injection needle 3 from a communicated state to a blocked state and vice versa (being "communicated" means that a drug solution or the like can flow between the discharge balloon 8 and the injection needle 3), a communicating tube 10a, and a tube 10b. The capsule medical apparatus 1 further includes an imaging unit 11, a transmitting unit 12, a control unit 13, and a power unit 14. The imaging unit 11 captures in-vivo images of the subject. The transmitting unit 12 performs wireless transmission with a transmitting apparatus (not shown), which is located outside the subject. The control unit 13 controls each of the components of the capsule medical apparatus 1. The power unit 14 can be a battery or the like.

The capsule casing 2 is shaped like a capsule and is of a size that can be introduced into a subject, e.g., a patient. The capsule casing 2 is made by sealing the open end of the cylinder-shaped container 2a, which is dome-shaped at its other end, with the dome-shaped container 2b. The dome-shaped container 2b is an optical member and is transparent to light of a predetermined waveband (e.g., visible light). In contrast, the cylinder-shaped container 2a is substantially opaque to visible light. There is an opening 2c on the cylinder-shaped container 2a, from which the injection needle 3 protrudes. The capsule casing 2 contains each of the components (the injection needle 3, the heater 4, the driving unit 6, the discharge balloon 8, the driving valve 9, the communicating tube 10a, the tube 10b, the imaging unit 11, the transmitting unit 12, the control unit 13, the power unit 14, and the like). The capsule casing 2 has a predetermined watertight structure (not shown) and maintains a watertight state of electric components, e.g., the driving unit 6, the driving valve 9, the imaging unit 11, the transmitting unit 12, the control unit 13, and the power unit 14.

The injection needle 3 is a hollow needle that has a pointed end (front end) and is made of a thermoplastic resin. The tube 10b is attached to the other end (rear end) of the injection needle 3. The supporter 5 is fixed near the rear end of the injection needle 3. The supporter 5 supports the injection needle 3 in a manner such that the injection needle 3 can protrude from the opening 2c in the capsule casing 2. The supporter 5 is connected with the driving unit 6. Furthermore, the heater 4 is attached to the outer surface of the injection needle. When the injection needle 3 is at a temperature lower than a predetermined temperature (e.g., lower than a body temperature), the injection needle 3 maintains its outer shape as a hollow needle. When the injection needle is heated by the heater 4 to a temperature equal to or higher than the predetermined temperature, the injection needle softens and becomes flexible so that the injection needle 3 easily changes its shape according to any contraction of the internal region.

The heater 4 functions as a sealing unit that is an exemplary leak prevention unit. The heater 4 heats the injection needle 3, which is made of a thermoplastic resin. The injection needle 3 then contracts so that the puncture hole of the internal region of the subject is sealed. The heater 4 is a thin-film electrical heater. The heater 4 surrounds the outer wall of the injection needle 3 and is fixed thereon. The heater 4 heats the injection needle 3 using power supplied from the control unit 13 to soften the injection needle, which then can easily change its shape, i.e., contract. The injection needle 3, which has been heated by the heater 4, easily changes its shape according to the contraction of the internal region that has been punctured and thus contracts to seal the puncture hole.

The puncture hole (i.e., the site of the puncture) is deemed to be in a sealed state (i.e., be sealed) when the opening size of the puncture hole contracts (i.e., is minimized) so that the liquid injected into the internal region (a liquid, e.g., a drug solution, that is injected into the internal region through the injection needle 3) does not leak from the puncture hole. Therefore, the puncture hole may not actually be completely sealed. The contraction of the injection needle 3 described above allows the opening size of the puncture hole to be minimized. The contraction can include crushing the opening of the injection needle 3 flat and other shape changes.

The driving unit 6 functions as a needle driving unit. The driving unit 6 protrudes the injection needle 3 from the capsule casing 2, punctures an internal region of a subject using the injection needle 3, pulls out the injection needle 3 that punctures the internal region, and stores the injection needle 3 inside the capsule casing 2. The driving unit 6 can be a linear actuator or the like and be connected with the supporter 5 that supports the injection needle 3. The driving unit 6 reciprocates the injection needle 3 in a predetermined direction (the direction of the arrow drawn with a thick line in FIG. 1) using the supporter 5. The driving unit 6 protrudes the injection needle 3 from the opening 2c to the outside of the capsule casing 2 and punctures an internal region using the injection needle 3. At the operational timing of the control unit 13, the driving unit 6 pulls out the injection needle 3 from the internal region and stores the injection needle 3 inside the capsule casing 2.

The discharge balloon 8 functions as a liquid injection unit that injects a liquid into an internal region using the injection needle 3 that punctures the internal region of the subject. The discharge balloon 8 can be made of an extendable elastic film. The discharge balloon 8 is attached to the communicating tube 10a. The discharge balloon 8, when it is expanded, contains and stores the drug solution 7 therein. The inside of the discharge balloon 8 is communicated with the communicating tube 10a and, when the driving valve 9 described later is open, communicated with the injection needle 3 through the tube 10b or the like. When the discharge balloon 8 is communicated with the injection needle 3, the discharge balloon 8 discharges the drug solution 7 to the injection needle 3 due to a contraction of the discharge balloon 8. The drug solution 7 is then injected into the internal region using the injection needle 3. When the communicated state between the discharge balloon 8 and the injection needle 3 is blocked by the driving valve 9 or the discharge balloon 8 cannot contract any more, the discharge balloon 8 stops discharging the drug solution 7 (i.e., injection stops).

The driving valve 9 can be an electromagnetic valve. The driving valve 9 opens and closes itself under the control of the control unit 13. The communicating tube 10a and the tube 10b are communicated with the driving valve 9. The driving valve 9 is communicated with the discharge balloon 8 through the communicating tube 10a. The driving valve 9 is communicated with the injection needle 3 through the tube 10b. When the driving valve 9 is in an open state, the discharge balloon 8 is communicated with the injection needle 3 by the communicating tube 10a and the tube 10b. When the driving valve 9 is in a closed state, the discharge balloon 8 and the injection needle 3 are not communicated.

The tube 10b, which connects the driving valve 9 with the injection needle 3 so that the driving valve 9 and the injection needle 3 are communicated with each other, may be a tube that is made of thermoplastic materials or a tube that is made of extendable elastic materials. The tube 10b can be of any length that does not hinder the protrusion of the injection needle 3.

The imaging unit 11 captures in-vivo images of a subject. The imaging unit 11 includes an illumination unit 11a (e.g., an LED), an optical system 11b (e.g., a collective lens), a solid-state imaging device 11c (e.g., CCD and CMOS imaging sensors and the like). The imaging unit 11 is fixed in the capsule casing 2 in a manner such that the optical axis of the optical system 11b is consistent with an axis along a predetermined relative direction of the capsule casing 2 (e.g., a central axis CL along the longitudinal direction of the capsule casing 2) and such that the imaging view of the imaging unit 11 is directed in a predetermined direction (e.g., the longitudinal direction of the capsule casing 2). One or more illumination units 11a of the imaging unit 11 (it is preferable that the number be more than one) illuminate the inside of the organ of the subject. The internal organs of the subject are the photographic subject of the imaging unit 11. The optical system 11b collects reflective light from the photographic subject and forms an optical image of the photographic subject on the light-receiving surface of the solid-state imaging device 11c. The solid-state imaging device 11c captures an optical image of the photographic subject, i.e., an in-vivo image of the subject, which has been formed by the optical system 11b. The solid-state imaging device 11c generates a signal by performing a photoelectric conversion process. The imaging unit 11 transmits the signal to the control unit 13.

The transmitting unit 12 transmits and receives wireless signals to and from an external apparatus (not shown), e.g., an image displaying apparatus. The transmitting unit 12 includes a wireless antenna (not shown) and transmits and receives wireless signals via the wireless antenna. Under the control of the control unit 13, the transmitting unit 12 wirelessly transmits the in-vivo image of the subject captured by the imaging unit 11 described above to the external apparatus outside the subject. The transmitting unit 12 performs a modulation process or the like on the image signals (including data of in-vivo images) obtained from the control unit 13 in order to generate wireless signals that include the image signals. The transmitting unit 12 transmits the generated wireless signals to the external apparatus that is located outside the subject via the wireless antenna. Under the control of the control unit 13, the transmitting unit 12 receives the wireless signals transmitted from the receiving apparatus that is located outside the subject and then performs a demodulation process or the like on the received wireless signals to extract control signals from the wireless signals. The transmitting unit 12 transmits the control signal obtained from the external apparatus to the control unit 13.

The control unit 13 includes a CPU that executes predetermined programs, a ROM that stores various kinds of data therein, and a RAM that stores arithmetic parameters and the like therein. The control unit 13 controls each of the components in the capsule medical apparatus 1 (e.g., the heater 4, the driving unit 6, the driving valve 9, the imaging unit 11, and the transmitting unit 12) and controls input and output of signals among the components. Further, the control unit 13 controls the driving valve 9, which in turn controls the discharge operation (injection operation) of the discharge balloon 8 described above. According to the control signal that is transmitted from the external apparatus and obtained by the transmitting unit 12, the control unit 13 controls the heater 4, the driving unit 6, and the driving valve 9. In doing so, a series of operations are completed that include puncturing of an internal region with the injection needle 3, injecting the drug solution 7 into the internal region, and pulling out the injection needle 3 from the internal region after the injection, and storing the injection needle 3 inside the capsule casing 2. The series of operations further include the heating process that heats the injection needle 3 using the heater 4 (i.e., the sealing process that seals the puncture hole in the internal region), the protruding process that protrudes the injection needle 3 using the driving unit 6, and the discharge (injection) operation that discharges the drug solution 7 using the discharge balloon 8.

The control unit 13 further includes an image processing unit 13a. The control unit 13 controls the operational timing of the imaging unit 11, and then the solid-state imaging device 11c captures an image of a photographic subject (i.e., an in-vivo image of the subject), which is illuminated by the illuminating unit 11a. The image processing unit 13a obtains the signal, on which the photoelectric conversion is performed by the solid-state imaging device 11c, and performs predetermined signal processes on the obtained signal to generate the image signal, which includes the data of the in-vivo image of the subject. Under the control of the control unit 13, the transmitting unit 12 wirelessly transmits the image signal to the external apparatus that is located outside the subject. Each time the image processing unit 13a generates an image signal (i.e., each time the imaging unit 11 captures an in-vivo image of the subject), the control unit 13 repeats the control process on the transmitting unit 12. The control unit 13 also controls the transmitting unit 12 when the transmitting unit 12 obtains the control signal from the external apparatus that is located outside the subject.

The power unit 14 can be a switch, a button-shaped battery, and the like. When the power unit 14 is switched to an ON state by the switch, the power unit 14 supplies power to the heater 4, the driving unit 6, the driving valve 9, the imaging unit 11, the transmitting unit 12, and the control unit 13, which have been described above, as needed. When the power unit 14 is switched to an OFF state by the switch, the power unit 14 stops supplying power to each of the components, e.g., the control unit 13. The switch of the power unit 14 can be a magnetic switch that switches the state of the power unit 14 from the ON state to the OFF state and vice versa according to a magnetic field that is applied from the outside, or an optical switch that switches the state of the power unit 14 from the ON state to the OFF state and vice versa according to a predetermined optical signal, e.g., infrared light.

The capsule medical apparatus 1 configured as above is swallowed and introduced into the organs of a subject. The capsule medical apparatus 1 moves through the organs (i.e., inside the digestive tracts) of the subject due to the peristalsis or the like. The capsule medical apparatus 1 captures in-vivo images of the subject in sequence using the imaging unit 11 at predetermined intervals (e.g., 0.5-second intervals). The capsule medical apparatus 1 wirelessly transmits image signals of the in-vivo images in sequence to the external apparatus that is located outside the subject using the transmitting unit 12.

As described, the capsule medical apparatus 1 inside the subject continuously captures the in-vivo images of the subject in sequence and wirelessly transmits these in-vivo images while moving through the organs of the subject. The capsule medical apparatus 1 eventually reaches an internal region of interest, into which the drug solution 7 is to be injected. The capsule medical apparatus 1 that has reached the internal region punctures the internal region of interest with the injection needle 3 and injects the drug solution 7 through the injection needle 3. The capsule medical apparatus 1 seals the puncture hole in the internal region during a period of time between when the drug solution 7 is injected and when the injection needle 3 is pulled out. After pulling out the injection needle 3, the capsule medical apparatus 1 stores the injection needle 3 inside the capsule casing 2. Thus, the series of operations for injecting the drug solution 7 into the internal region are completed. After storing the injection needle 3 inside the capsule casing 2, the capsule medical apparatus 1 moves through the organs of the subject until excreted by the subject.

Figure 2B:
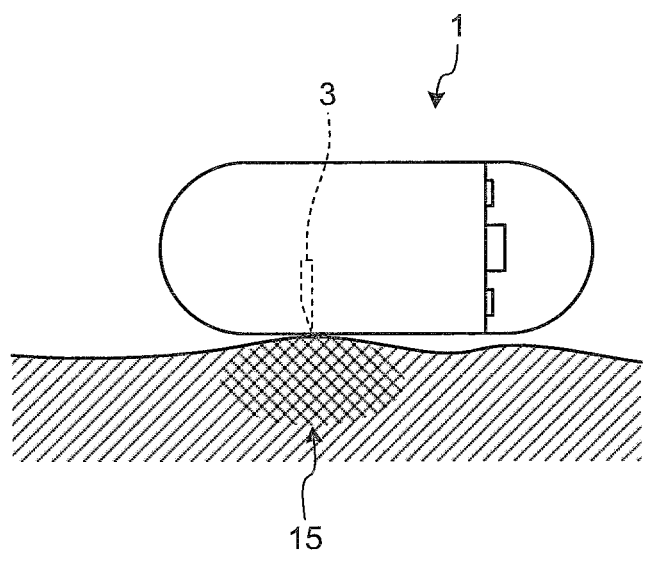
Figure 3A:
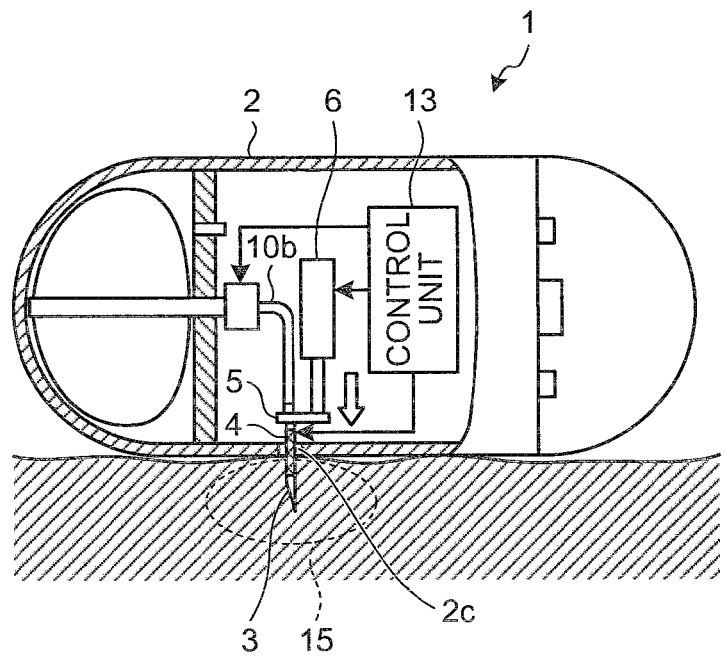
FIGS. 3A and 3B are schematic diagrams in which the capsule medical apparatus inside the subject injects a drug solution into the affected area.
Figure 3B:
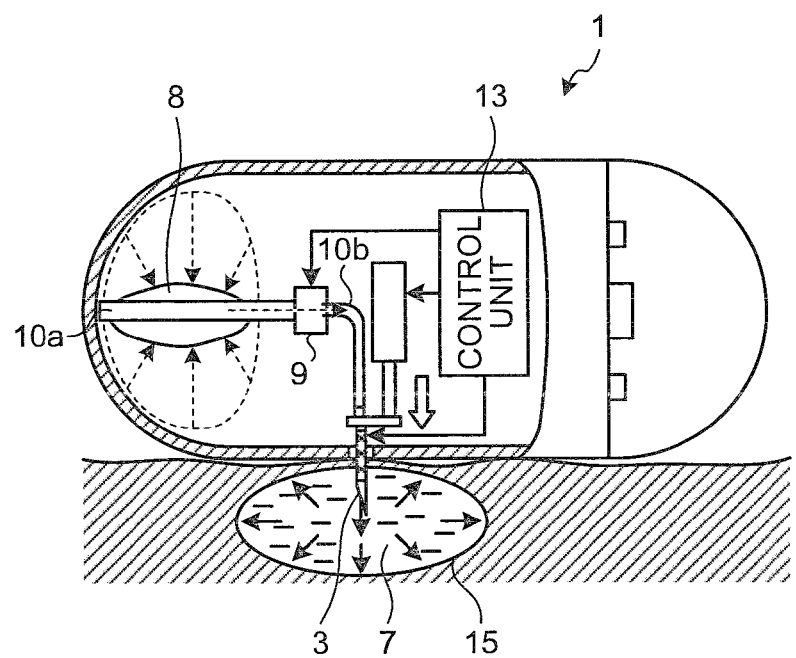
Figure 4A:
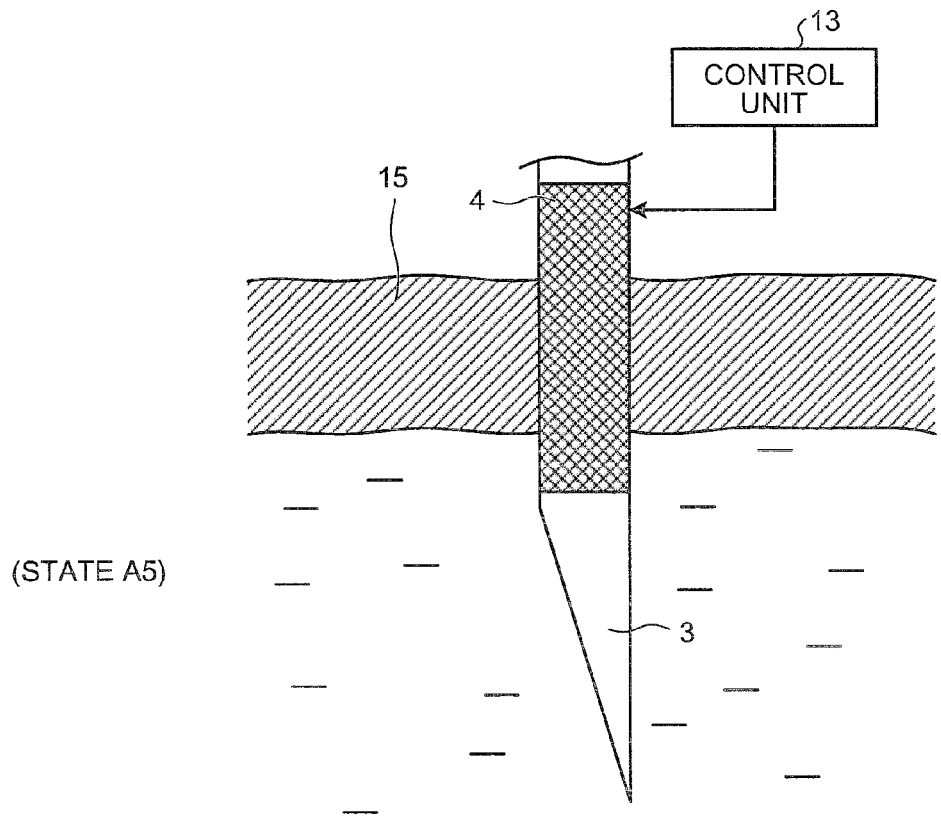
FIGS. 4A and 4B are schematic diagrams in which a puncture hole contracts due to the contraction of the injection needle.
Figure 4B:
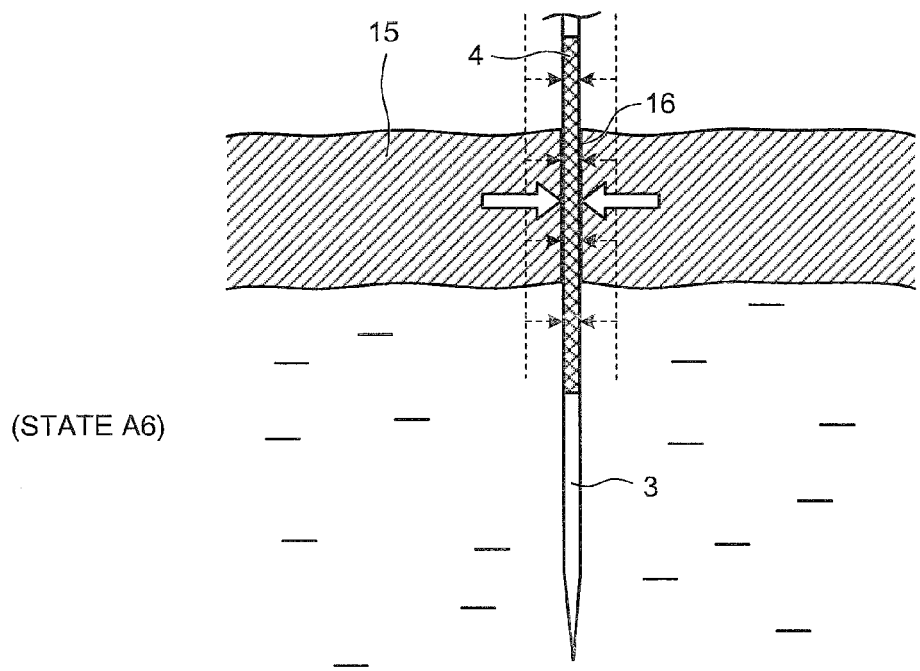
Figure 5:
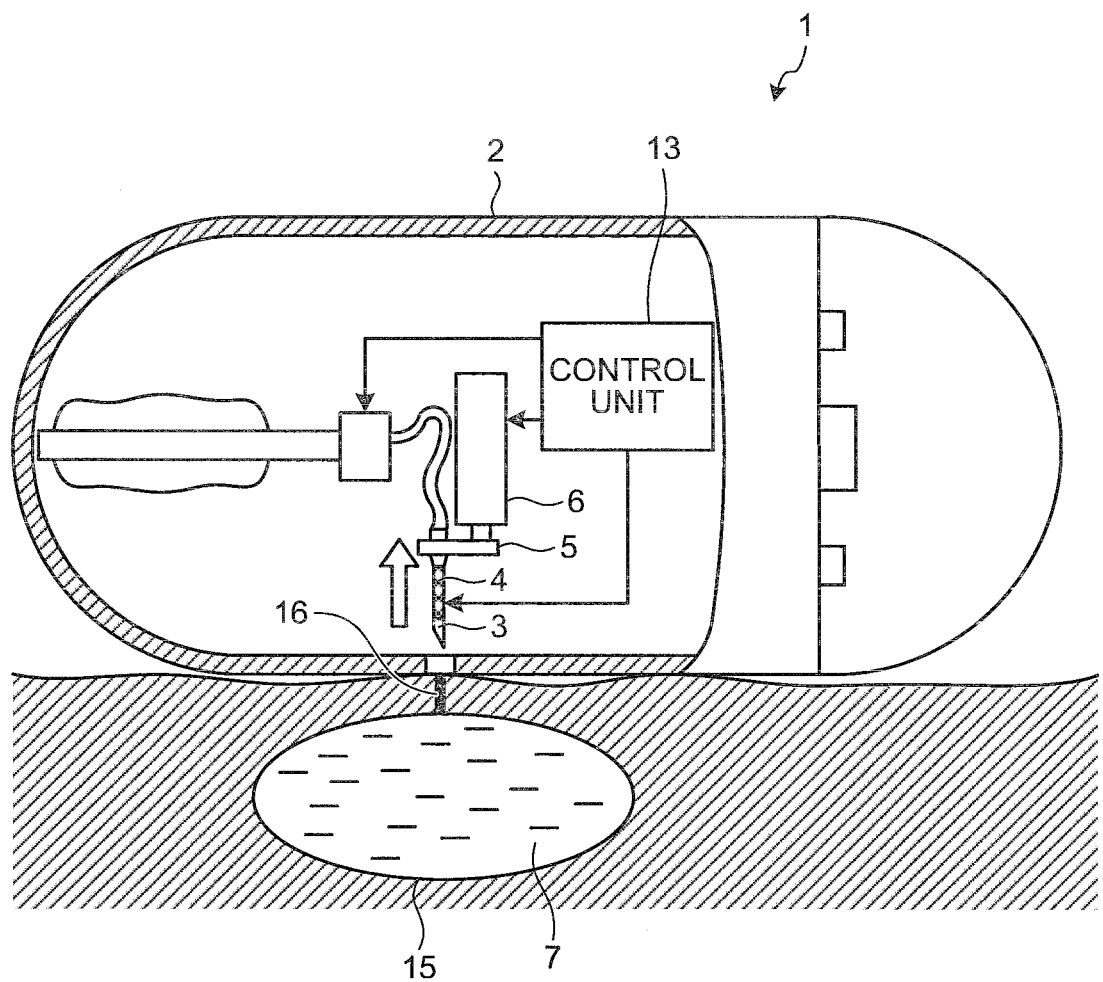
FIG. 5 is a schematic diagram in which the contracted injection needle is stored in a capsule casing.

The capsule medical apparatus 1 according to the first embodiment of the present invention is described in detail. As an example of operations of the capsule medical apparatus 1, the capsule medical apparatus 1 injects a drug solution into an affected area, which is an example of a region of interest, inside a subject. FIGS. 2A and 2B are schematic diagrams in which the capsule medical apparatus inside the subject approaches (FIG. 2A) and reaches (FIG. 2B) the affected area. FIGS. 3A and 3B are schematic diagrams in which the capsule medical apparatus inside the subject injects the drug solution into the affected area. FIGS. 4A and 4B are schematic diagrams in which a puncture hole is sealed by the contraction of the injection needle. FIG. 5 is a schematic diagram in which the injection needle, which has contracted, is stored into the capsule casing.

As described, the capsule medical apparatus 1 is swallowed and introduced into the organs of the subject, e.g., a patient. The capsule medical apparatus 1 inside the subject captures in-vivo images of the subject and wirelessly transmits the in-vivo images while moving through the digestive organs due to the peristalsis or the like. As shown in FIG. 2A, the capsule medical apparatus 1 eventually approaches an affected area 15 (State A1). The capsule medical apparatus 1 wirelessly transmits the in-vivo images captured by the imaging unit 11 to the external apparatus that is located outside the subject. The external apparatus displays the in-vivo images received from the capsule medical apparatus 1 on a display. Users, such as doctors and nurses, view information displayed by the external apparatus to confirm that the capsule medical apparatus 1 inside the subject has approached the affected area 15.

As shown in FIG. 2B, the capsule medical apparatus 1 near the affected area 15 reaches the affected area 15 due to the peristalsis or the like and adjusts the injection needle 3 to hit the affected area 15 (State A2). The users view the information displayed by the external apparatus to confirm that the capsule medical apparatus 1 inside the subject has reached the affected area 15.

The external apparatus generates a control signal for the capsule medical apparatus 1 based on commands from users and wirelessly transmits the generated control signal to the capsule medical apparatus 1 inside the subject. The capsule medical apparatus 1 inside the subject receives the control signal from the external apparatus via the transmitting unit 12 described above. Based on the received control signal, the capsule medical apparatus 1 performs a series of operations that puncture the affected area with the injection needle 3, inject the drug solution 7 into the affected area 15, and store the injection needle 3 inside the capsule casing 2.

In the capsule medical apparatus 1, the control unit 13 controls the driving unit 6 so that the injection needle 3 protrudes from the capsule casing 2 according to the above-described control signal from the external apparatus. Firstly, the driving unit 6 moves the supporter 5 toward the opening 2c. As shown in FIG. 3A, the injection needle 3 supported by the supporter 5 moves through the opening 2c and protrudes from the capsule casing 2 to puncture the affected area 15 (State A3). The tube 10b does not hinder the protrusion of the injection needle 3. The heater 4 does not hinder the puncture of the injection needle 3 inside the affected area 15 and stays fixed on the outer surface of the injection needle 3.

When puncturing the affected area 15 with the injection needle 3 is completed, the control unit 13 controls the driving valve 9 so that the discharge operation that discharges the drug solution 7 using the discharge balloon 8 is started. The driving valve 9 opens itself and thus switches the state between the discharge balloon 8 and the injection needle 3 to the communicated state so that the discharge balloon 8 and the injection needle 3 are communicated by the communicating tube 10a and the tube 10b. The discharge balloon 8 makes the drug solution 7 flow through the communicating tube 10a, the driving valve 9, and the tube 10b to inject the drug solution 7 into the affected area 15. After the drug solution 7 is discharged through the injection needle 3 and injected into the affected area 15, the drug solution 7 causes the inside of the affected area 15 to expand as shown in FIG. 3B (State A4).

In a predetermined time after the drug solution 7 starts to be injected into the affected area 15 through the injection needle 3, the control unit 13 controls the driving valve 9 so that the communicated state between the injection needle 3 and the discharge balloon 8a is blocked. During this operation, the affected area 15 stays punctured by the injection needle 3. The driving valve 9 blocks communicated state between the discharge balloon 8 and the injection needle 3 by closing itself. Thus, the injection operation that injects the drug solution 7 into the affected area 15 using the discharge balloon 8 is completed. The control unit 13 can control the discharged (injected) amount of the drug solution 7 from the discharge balloon 8 by changing the instant when the driving valve 9 is switched so that a desired amount of the drug solution 7 for the affected area 15 is injected.

After the injection operation is completed, the control unit 13 controls a heating process that heats the injection needle 3 by applying power to the heater 4. The heater 4 starts to produce heat using the power supplied from the control unit 13 and heats the injection needle 3 that punctures the affected area 15. The injection needle 3 is heated by the heater 4 to a temperature equal to or higher than a predetermined temperature, which is at least higher than the body temperature. The injection needle 3 softens due to the heat while the injection needle 3, which has punctured the affected area 15, remains in the affected area 15. The outer shape of the injection needle 3 has been a hollow needle as shown in FIG. 4A (State A5). When the injection needle 3 softens as described above, the injection needle 3 changes its outer shape and contracts due to the contraction of the affected area 15 as shown in FIG. 4B (State A6). As a result, the opening size of a puncture hole 16 that is made by the injection needle 3 in the affected area 15 is minimized. The puncture hole 16 is thus sealed so that the drug solution 7 inside the affected area 15 does not leak therefrom.

In a predetermined time after the heater 4 starts the heating process on the injection needle 3 (i.e., when the injection needle 3 that punctures the affected area 15 contracts enough due to the contraction of the affected area 15), the control unit 13 controls the heater 4 so that the heating process on the injection needle 3 is stopped. The power supply for the heater 4 is stopped by the control unit 13. Thus, the heating process on the injection needle 3 is completed.

Then, when the injection needle 3 contracts enough (i.e., when the puncture hole 16 in the affected area 15 has been sealed), the control unit 13 controls the driving unit 6 so that the injection needle 3 is stored inside the capsule casing 2. The driving unit 6 moves the supporter 5 away from the opening 2c to pull out the injection needle 3 from the affected area 15 and stores the injection needle into the capsule casing 2 (State A7).

The puncture hole 16 (site of puncture) in the affected area 15, from which the injection needle 3 has been pulled out, is sealed as described above. Therefore, the drug solution 7 is contained in the affected area 15 and does not leak from the puncture hole 16 even after the injection needle 3 is pulled out. As a result, the drug solution 7 in the affected area 15 does not spread over regions inside the subject other than the affected area 15.

As described above, in the first embodiment of the present invention, the injection needle that punctures the internal region is made of thermoplastic materials. The discharge balloon injects the drug solution into the internal region with the injection needle that punctures the internal region. The heater heats the injection needle that punctures the internal region so that the injection needle softens. The softened injection needle easily contracts according to the contraction of the internal region, whereby the puncture hole in the internal region is sealed. Thus, the opening size of the puncture hole can contract due to the contraction of the injection needle while the injection needle remains in the internal region. In this way, the puncture hole can be sealed and, at the same time, injected liquids, e.g., the drug solution, do not leak from the puncture hole in the internal region. Therefore, the capsule medical apparatus can prevent the drug solution from leaking from the internal region after the injection needle, which has been used for injecting the drug solution, is pulled out from the internal region.

The capsule medical apparatus according to the present invention can prevent a drug solution that is injected into a region of interest, e.g., an affected area, inside a subject from leaking from a puncture hole of the region of interest. Therefore, the capsule medical apparatus can prevent the drug solution from spreading and causing unintended effects on internal regions other than the region of interest (i.e., on unintended internal regions). Furthermore, when the drug solution is a colored liquid, the capsule medical apparatus has an additional advantage of preventing the colored liquid from leaking from the internal region to be attached to the outer surface of the capsule medical apparatus and impairing the field of view (imaging field) of the capsule medical apparatus.

A second embodiment of the present invention is described below. In the first embodiment described above, in order to seal a puncture hole that is made by the injection needle 3 in an internal region, the injection needle 3 is heated for the contraction of the injection needle. In the second embodiment, a flexible tube is fitted to the outer surface of the injection needle in a manner such that the flexible tube can slide. The injection needle with the flexible tube punctures an internal region and injects a drug solution into the internal region. Then, only the injection needle is pulled out from the puncture hole in the internal region, and the flexible tube is left. The flexible tube contracts according to the contraction of the internal region so as to seal the puncture hole.

FIG. 6 is a schematic diagram of an exemplary configuration of a capsule medical apparatus according to the second embodiment of the present invention. As shown in FIG. 6, a capsule medical apparatus 21 according to the second embodiment includes an injection needle 23 and a control unit 29 instead of the injection needle 3 and the control unit 13 of the capsule medical apparatus 1. The capsule medical apparatus 21 further includes a thin-film tube 24 that is fitted to the outer surface of the injection needle 23 in a manner such that the thin-film tube can slide, a supporter 25 that supports the thin-film tube 24, and a driving unit 26 that reciprocates the thin-film tube 24 in linear directions using the supporter 25. Other configurations of the capsule medical apparatus 21 are the same as those of the first embodiment, and same numerals are attached to same components.

The injection needle 23 is a hard hollow needle that is made of metals or the like. The injection needle 23 does not contract due to the contraction of the internal region that is punctured by the injection needle 23. The tube 10b is attached to the rear end of the injection needle. The injection needle 23 is communicated with the driving valve 9 through the tube 10b. The supporter 5 is attached to the injection needle 23 near the rear end of the injection needle 23. The injection needle 23 is driven by the driving unit 6 to protrude from the capsule casing 2, similarly to the injection needle 3 according to the first embodiment described above. The injection needle 23 has a hollow structure similar to that of the injection needle 3 according to the first embodiment described above.

The thin-film tube 24 is a soft tube that is made of soft resinous film. The inner diameter of the thin-film tube 24 is substantially equal to the outer diameter of the injection needle 23. The supporter 25 is fixed on the thin-film tube 24 near the rear end of the thin-film tube 24. The supporter 25 supports the thin-film tube 24 in a manner such that the thin-film tube 24 can protrude from the opening 2c in the capsule casing 2. The thin-film tube 24 is fitted to the outer surface of the injection needle 23 in a manner such that the thin-film tube 24 can slide. Thus, the thin-film tube 24 enters a puncture hole in an internal region along with the injection needle 23 that punctures the internal region. The thin-film tube 24, which has entered the puncture hole, keeps being fitted to the injection needle 23 and thus maintains its cylinder shape. When the injection needle 23 is pulled out, the thin-film tube 24 is easily crushed due to the contraction of the internal region so that the thin-film tube 24 contracts.

The driving unit 26 functions as a tube driving unit that makes the thin-film tube 24 protrude from the opening 2c in the capsule casing 2. The driving unit 26 can operate independently of the driving unit 6 that makes the injection needle 23 protrude. The driving unit 26 can be a linear actuator or the like. The driving unit 26 is connected with the supporter 25 that supports the thin-film tube 24 and reciprocates the thin-film tube 24 in a direction to which the injection needle 23 protrudes (in the direction of the arrow drawn with a thick line in FIG. 6). Under the control of the control unit 29, between when the driving unit 26 makes the thin-film tube protrude along with the injection needle 23 toward an internal region and when the driving unit 6 described above pulls out the injection needle 23 from the internal region, the driving unit 6 keeps the thin-film tube 24 remaining in the puncture hole of the internal region. Under the control of the control unit 29, after the pullout of the injection needle 23, the driving unit 26 pulls the thin-film tube 24 from the internal region and stores the thin-film tube 24 into the capsule casing 2.

When being fitted to the injection needle 23, the thin-film tube 24 that has entered the puncture hole in the internal region along with the injection needle 23 will not be crushed by living tissue around the puncture hole and maintains its cylinder shape. However, when the injection needle 23 is gradually pulled out from the internal region by the driving unit described above, the thin-film tube 24 in the puncture hole narrows a hollowed part of the injection needle 23 until the thin-film tube 24 contracts (e.g., is crushed flat) due to the contraction of the internal region so as to seal the puncture hole. The thin-film tube 24 and the driving unit 26 function as a sealing unit that is an exemplary unit for minimizing the opening size of the puncture hole in the internal region that is made by the injection needle 23 to prevent the leak therefrom.

The control unit 29 controls the driving unit 26 so that the thin-film tube 24 protrudes together with the injection needle 23 from the capsule casing 2. Specifically, the control unit 29 controls the driving unit 6 and the driving unit 26 so that the injection needle 23 and the thin-film tube 24 protrude together. The control unit 29 also controls the driving unit 26 so that the driving unit 26 keeps the thin film tube 24 remaining in the puncture hole until the injection needle 23 is pulled out from the internal region by the driving unit 6. After the pullout of the injection needle 23, the control unit 29 controls the driving unit 26 so that the thin-film tube 24 is pulled out from the internal region and then stored into the capsule casing 2. Other than the function to control the operation of the driving unit 26, the control unit 29 has the same functions as those of the control unit 13 of the first embodiment described above.

Figure 7A:
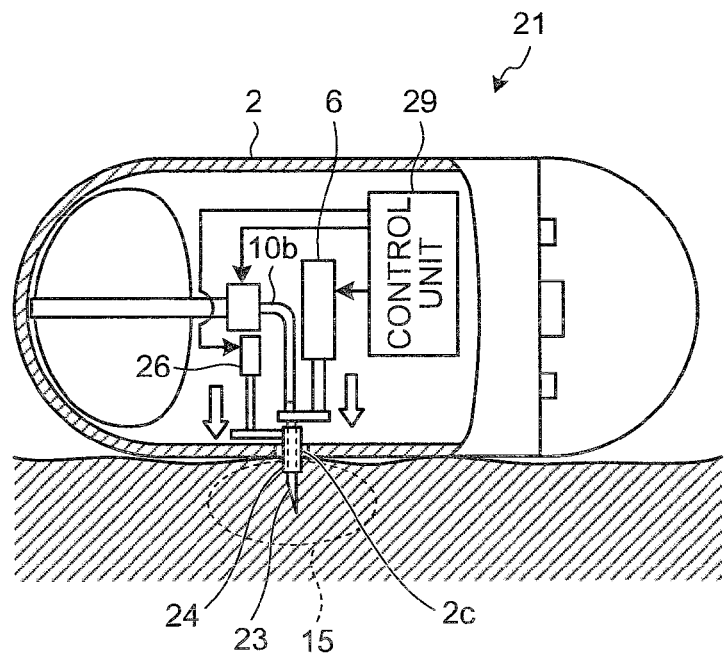
FIGS. 7A and 7B are schematic diagrams in which the capsule medical apparatus inside the subject punctures an affected area using the injection needle and a thin-film tube.
Figure 7B:
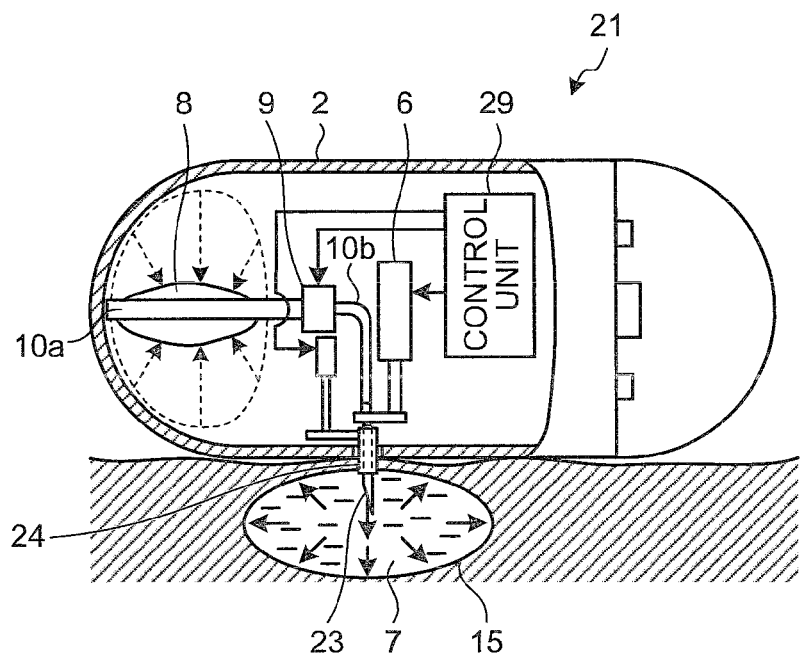
Figure 8:
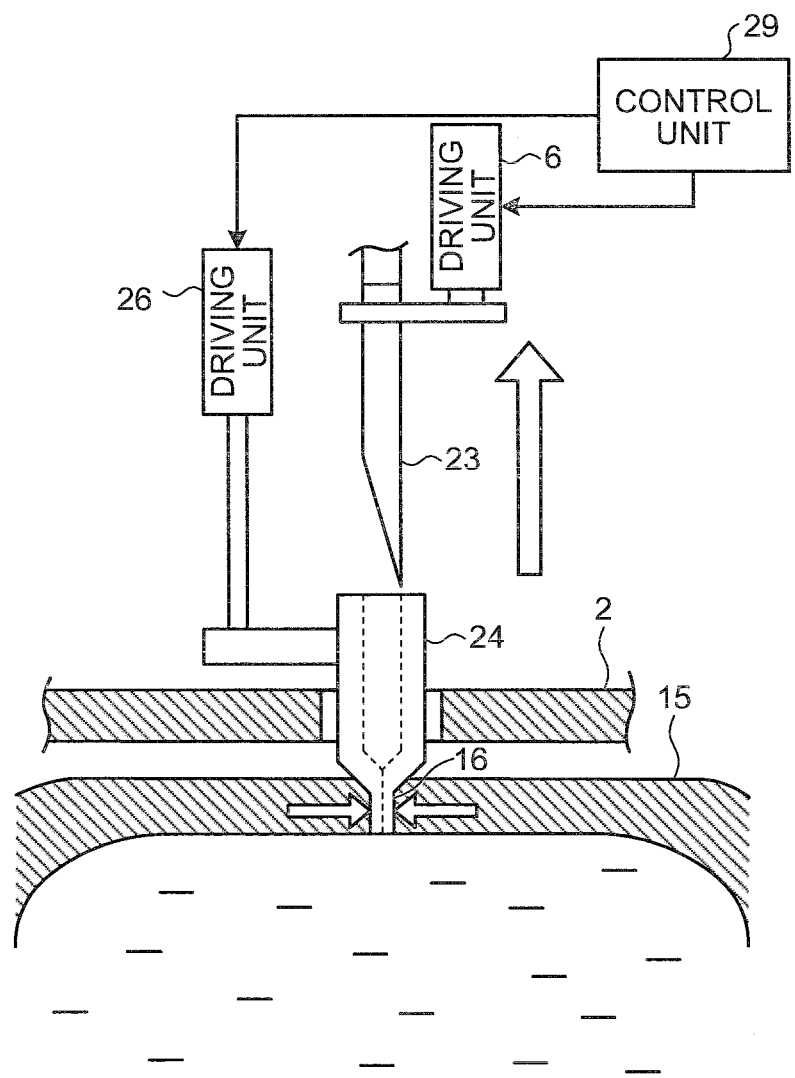
FIG. 8 is a schematic diagram in which the puncture hole in the internal region contracts due to the contraction of the thin-film tube.
Figure 9:
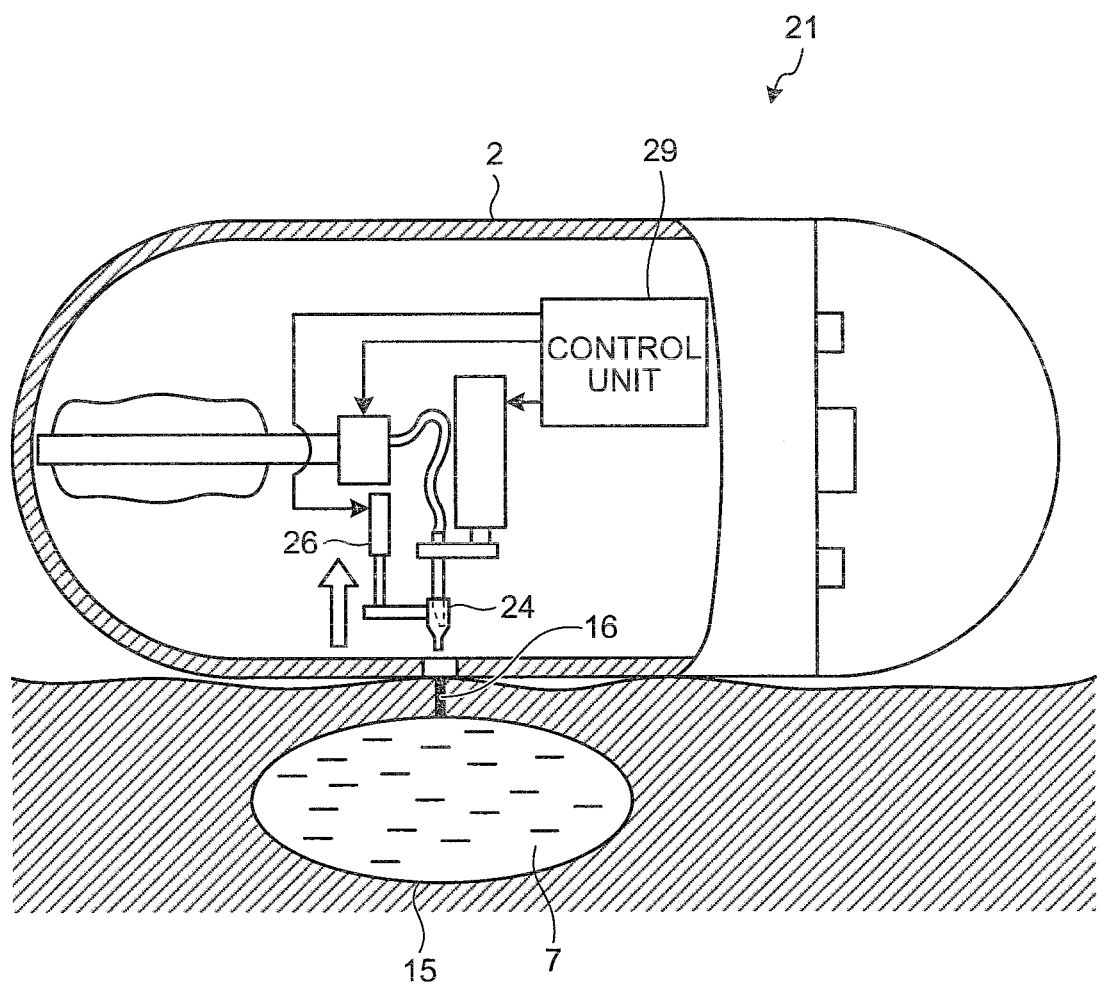
FIG. 9 is a schematic diagram in which the thin-film tube is stored in the capsule casing.

Operations of the capsule medical apparatus 21 according to the second embodiment are described more exactly. An example of the operations is that the capsule medical apparatus 21 injects a drug solution into an affected area, which is an example of an internal region of interest, inside a subject. FIGS. 7A and 7B are schematic diagrams in which the capsule medical apparatus inside the subject punctures the affected area with the injection needle along with the thin-film tube. FIG. 8 is a schematic diagram in which the puncture hole in the internal region is sealed due to the contraction of the thin-film tube. FIG. 9 is a schematic diagram in which the thin-film tube is stored into the capsule casing. The capsule medical apparatus 21 according to the second embodiment adjusts the injection needle 23 to hit the affected area 15 when reaching the affected area 15, similarly to the capsule medical apparatus 1 according to the first embodiment described above.

When the capsule medical apparatus 21 reaches the affected area 15 inside the subject, the control unit 29 controls the driving unit 6 and the driving unit 26 so that the thin-film tube 24 and the injection needle 23 protrude together from the capsule casing 2. Similarly to the first embodiment, the driving unit 6 protrudes, based on the control signal from the external apparatus described above, the injection needle 23 from the opening 2c in the capsule casing 2 to puncture the affected area 15 with the injection needle 23. At the same time with the protrusion of the injection needle 23, the driving unit 26 protrudes the thin-film tube 24 from the opening 2c. As shown in FIG. 7A, the thin-film tube 24 enters the puncture hole in the affected area 15 along with the injection needle 23 while being fitted to the outside of the injection needle 23 (State B3).

When the injection needle 23 with the thin-film tube 24 has punctured the affected area 15, the control unit 29 controls the driving valve 9 so that the discharge operation that discharges the drug solution using the discharge balloon 8 is started. The discharge balloon 8 injects the drug solution 7 into the affected area 15 through the injection needle 23 that punctures the internal region, similarly to the first embodiment described above. As shown in FIG. 7B, the drug solution 7 that is injected into the affected area 15 extends the inside of the affected area 15 (State B4).

The control unit 29 keeps the injection needle 23 and the thin-film tube 24 inside the puncture hole in the affected area 15. In a predetermined time after the drug solution 7 starts to be injected into the affected area 15 through the injection needle 23, the control unit 29 controls the driving valve 9 so that the communicated state between the injection needle 23 and the discharge balloon 8 is blocked. The discharge balloon 8 completes the injection operation after injecting a required amount of the drug solution 7 into the affected area 15.

When the injection operation that discharges the drug solution 7 using the discharge balloon 8 is completed, the control unit 29 controls the driving unit 6 so that the injection needle 23 is pulled out from the affected area 15 and also controls the driving unit 26 so that the thin-film tube 24 remains in the puncture hole 16 in the affected area 15. The injection needle 23, which is driven by the driving unit 6, slides along the inside of the thin-film tube 24 and is gradually pulled out from the puncture hole 16. The thin-film tube 24, which is driven by the driving unit 26, does not hinder the pullout of the injection needle 23 and remains in the puncture hole 16 (see FIG. 8).

The thin-film tube 24 that remains in the puncture hole 16 in the affected area 15 gradually narrows the inner hollowed part due to the pullout of the injection needle 23, until the injection needle 23 is completely pulled out from the puncture hole 16. Then, a part of the thin-film tube 24 that is surrounded by the living tissue of the affected area 15 (i.e., a part of the thin-film tube 24 that is inside the puncture hole) becomes a hollow structure. The part of the thin-film tube 24, which is hollow, is easily crushed flat due to the contraction of the affected area 15 (State B5). As a result, the opening size of the puncture hole 16 in the affected area 15 that is made by the injection needle 23 is minimized to prevent the leak of the drug solution 7 inside the affected area 15. The puncture hole 16 is thus sealed.

In a predetermined time after the control unit 29 starts to control the driving unit 6 so that the injection needle 23 is pulled out from the affected area 15 as described above, the control unit 29 controls the driving unit 26 so that the thin-film tube 24 is pulled out from the puncture hole 16 in the affected area 15. Specifically, when the part of the thin-film tube 24 has been crushed flat sufficiently due to the contraction of the affected area 15 (i.e., when the puncture hole 16 in the affected area 15 has been sealed), the control unit 29 controls the driving unit 26 so that the thin-film tube 24 is stored into the capsule casing 2. The driving unit 26 pulls out the thin-film tube 24 from the puncture hole 16 in the affected area 15 and stores the thin-film tube 24 into the capsule casing 2 (State B6).

The puncture hole (the site of the puncture) 16 in the affected area 15, from which the thin-film tube 24 has been pulled out, is sealed. Therefore, the drug solution 7 remains inside affected area 15 and does not leak from the puncture hole 16 even after the injection needle 23 and the thin-film tube 24 are pulled out as described above. As a result, the drug solution 7 inside the affected area 15 does not leak out and spread over internal regions other than the affected area 15 inside the subject.

As described, in the second embodiment of the present invention, the thin-film tube is fitted to the outside of the hard injection needle. The injection needle with the thin-film tube punctures an internal region, injects the drug solution into the internal region, and pulls out the injection needle from the internal region while the thin-film tube remains in the puncture hole in the internal region. The thin-film tube that remains in the puncture hole easily contracts due to the contraction of the internal region so that the puncture hole in the internal region is sealed. Other configurations are the same as those of the first embodiment. Therefore, the capsule medical apparatus can provide the same operational effects as those of the first embodiment without heating the injection needle to make the injection needle contract. As a result, the capsule medical apparatus can save power.

A capsule medical apparatus according to a third embodiment of the present invention is described below. In the first embodiment described above, the injection needle 3 that punctures the internal region is heated and contracts so that the puncture hole in the internal region is sealed. In contrast, in the third embodiment, the injection needle is pulled out at speed that is lower than a speed of the contraction of the internal region so as to seal the puncture hole in the internal region that is made by the injection needle.

Figure 10:
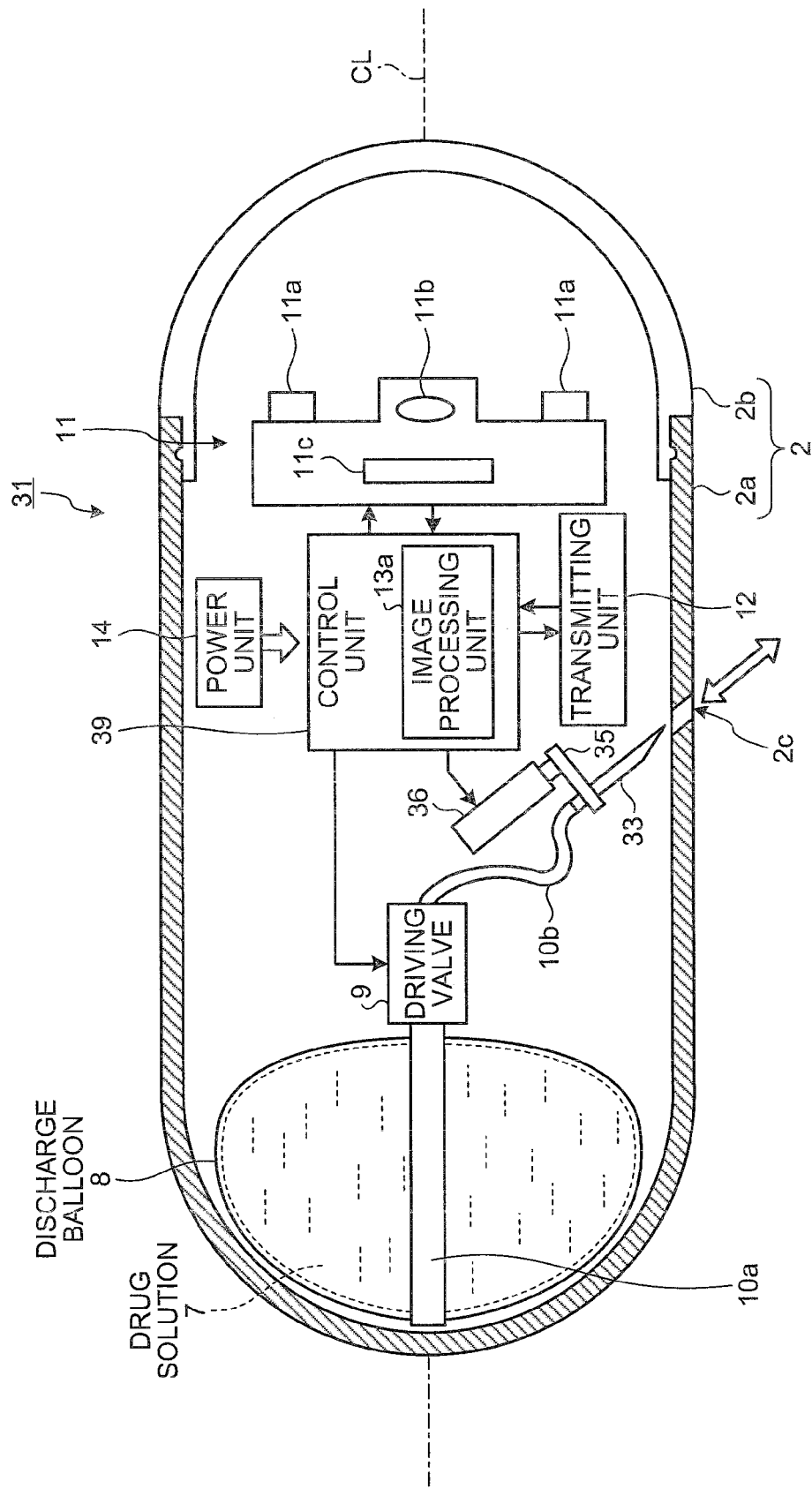
FIG. 10 is a schematic diagram of an exemplary configuration of a capsule medical apparatus according to a third embodiment of the present invention.

FIG. 10 is a schematic diagram of an exemplary configuration of the capsule medical apparatus according to the third embodiment of the present invention. As shown in FIG. 10, a capsule medical apparatus 31 includes an injection needle 33, a supporter 35, a driving unit 36, and a control unit 39 instead of the injection needle 3, the supporter 5, the driving unit 6, and the control unit 13 of the capsule medical apparatus 1 according to the first embodiment described above. Other configurations are the same as those of the first embodiment, and same numerals are attached to same components.

The injection needle 33 is a hard hollow needle that is made of metals or the like. The injection needle 33 does not contract due to the contraction of the internal region that is punctured by the injection needle 33. The tube 10b is attached to the rear end of the injection needle 33. The injection needle 33 is communicated with the driving valve 9 via the tube 10b. The supporter 35 is attached to the injection needle 33 near the rear end of the injection needle 33. The injection needle 33 has a hollow structure similar to that of the injection needle 3 according to the first embodiment.

The supporter 35 supports the injection needle 33 in a manner such that the injection needle 33 can protrude from the opening 2c in the capsule casing 2. Specifically, the supporter 35 supports the injection needle 33 in a manner such that the longitudinal direction of the injection needle 33 is oblique to a radial direction of the capsule casing 2 and that the front opening of the injection needle 33 is directed toward an internal region when the injection needle 33 punctures the internal region. The radial direction of the capsule casing 2 is vertical to the central axis CL, i.e., the longitudinal direction of the capsule casing 2. When the longitudinal direction of the injection needle 33 is oblique to the radial direction of the capsule casing 2, the longitudinal direction of the injection needle 33 makes an acute angle, which is smaller than 90 degree, with the longitudinal direction and the radial direction of the capsule casing 2.

The driving unit 36 functions as a needle driving unit that makes the injection needle 33 protrude from the capsule casing 2, punctures an internal region of a subject with the injection needle 33, pulls out the injection needle 33 that punctures the internal region, and stores the injection needle 33 into the capsule casing 2. The driving unit 36 can be a linear actuator or the like and is connected with the supporter 35 that supports the injection needle 33. The driving unit 36 reciprocates the injection needle 33 along a predetermined oblique direction (the direction of the arrow drawn with a thick line in FIG. 10) using the supporter 35. The driving unit 36 makes the injection needle 33 protrude from the opening 2c in the capsule casing 2 and punctures the internal region of the subject at a predetermined movement speed. Then, at the instant determined by the control unit 39, the driving unit 36 pulls out the injection needle 33 from the internal region at a movement speed lower than the speed of the contraction of the internal region and stores the injection needle 33 into the capsule casing 2.

The control unit 39 controls the movement speed of the driving unit 36 so as to control the movement speed (puncture speed) for the injection needle 33 to puncture the internal region and the movement speed (pullout speed) for the injection needle 33 to be pulled out therefrom. Specifically, the control unit 39 controls the driving unit 36 so that the injection needle 33, which protrudes from the capsule casing 2, punctures the internal region at a predetermined puncture speed. The control unit 39 controls the driving unit 36 so that the injection needle 33 is pulled out from the internal region at a predetermined pullout speed that is lower than the speed of the contraction of the internal region. The pullout speed of the injection needle 33 that is controlled by the control unit 39 may be higher than the puncture speed of the injection needle 33 as long as the pullout speed is lower than the speed of the contraction of the internal region into which the drug solution 7 is injected through the injection needle 33. The pullout speed of the injection needle 33 may be lower than or equal to the puncture speed of the injection needle 33. Other than the function to control the movement speed of the driving unit 36 (i.e., the function to control the puncture speed and the pullout speed of the injection needle 33), the control unit 39 provides the same functions as those of the control unit 13 of the capsule medical apparatus according to the first embodiment described above.

Figure 11:
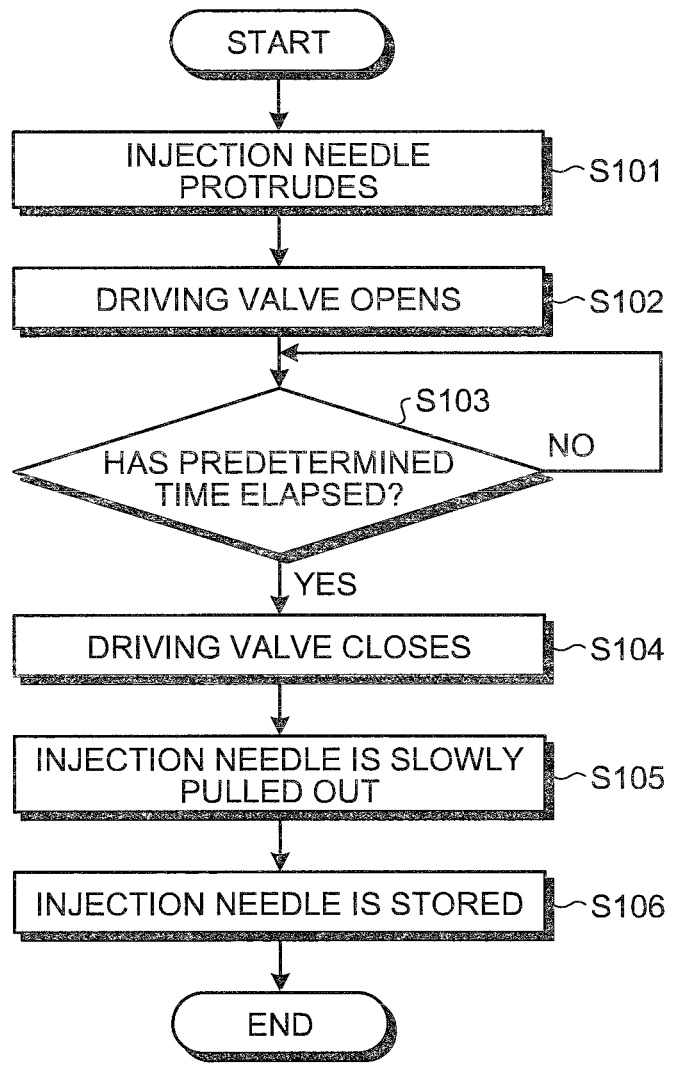
FIG. 11 is a flowchart of a procedure in which the capsule medical apparatus according to the third embodiment of the present invention makes an injection into an internal region.

The following describes a series of operations of the capsule medical apparatus 31 that are performed between when the injection needle 33 protrudes toward an internal region and when the injection needle 33 is pulled out therefrom after the injection and stored into the capsule casing 2. FIG. 11 is a flowchart of a procedure in which the capsule medical apparatus 31 according to the third embodiment of the present invention makes an injection into an internal region. The capsule medical apparatus 31 according to the third embodiment adjusts the injection needle to hit an internal region of interest when reaching an affected area, which is an example of the internal region of interest, inside the subject, similarly to the capsule medical apparatus according to the first embodiment described above.

When the capsule medical apparatus 31 reaches the internal region of interest, e.g., the affected area, inside the subject, the control unit 39 controls, based on the control signal from the external apparatus described above, the driving unit 36 so that the injection needle 33 protrudes from the capsule casing 2 at the predetermined puncture speed as shown in FIG. 11 (Step S101). Under the control of the control unit 39, the driving unit 36 makes the injection needle 33 protrude from the capsule casing 2 and punctures the internal region with the injection needle 33 at the predetermined puncture speed that is controlled by the control unit 39. The injection needle 33 punctures the internal region while the front opening thereof is directed toward the internal region.

The control unit 39 makes the driving valve 9 open while the injection needle 33 remains in the internal region (Step S102). The driving valve 9 is opened so that the discharge balloon 8 and the injection needle 33 are communicated with each other through the communicating tube 10a and the tube 10b. The discharge balloon 8 injects the drug solution 7 into the internal region through the injection needle 33. The drug solution 7 that is injected into the internal region extends the inside of the internal region, similarly to the first embodiment described above.

The control unit 39 determines whether a predetermined time has passed since the drug solution 7 starts to be injected into the internal region through the injection needle 33 (i.e., since the driving valve 9 opens) (Step S103). The determination process is performed while the injection needle 33 remains in the internal region. When the control unit 39 that the predetermined time has not passed since the drug solution 7 starts to be injected (Step S103, No), the control unit 39 repeats Step S103. In this case, the discharge balloon 8 keeps injecting the drug solution 7 into the internal region through the injection needle 33.

In contrast, when the control unit 39 determines that the predetermined time has passed since the drug solution 7 starts to be injected (Step S103, Yes), the control unit 39 makes the driving valve 9 close (Step S104). The driving valve 9 thus blocks the communicated state between the discharge balloon 8 and the injection needle 33 described above. The discharge balloon 8 completes injecting the needed amount of the drug solution 7 into the internal region before the communicated state between the discharge balloon 8 and the injection needle 33 is blocked by the driving valve 9.

When the injection process that injects the drug solution 7 using the discharge balloon 8 is completed, the control unit 39 controls the driving unit 36 so that the injection needle 33 is pulled out from the internal region into which the injection has been performed at a low speed (Step S105). Specifically, the control unit 39 controls the driving unit 36 so that the injection needle 33 is pulled out at the pullout speed that is lower than the speed of the contraction of the internal region into which the injection has been performed. The driving unit 36 moves the injection needle 33 at the low pullout speed. In doing so, a time required for the internal region to seal the puncture hole made by the injection needle 33 due to the contraction of the internal region (i.e., living tissue) is guaranteed before the injection needle 33 is completely pulled out from the internal region into which the injection has been performed. While the driving unit 36 pulls out the injection needle 33 from the puncture hole, the puncture hole in the internal region into which the injection has been performed is gradually sealed due to the contraction of the living tissue. The control unit 39, which controls the driving unit 36, functions as a sealing unit that is an exemplary leak prevention unit that prevents the leak from the puncture hole in the internal region that is made by the injection needle 33.

The control unit 39 controls the driving unit 36 so that the injection needle 33 that has been pulled out the internal region on which the injection has been performed, is stored inside the capsule casing 2 (Step S106). Thus, the series of operations (procedure) are completed. The driving unit 36 stores the injection needle 33 into the capsule casing 2 at the movement speed that is controlled by the control unit 39. The movement speed for storing the injection needle 33 may be equal to or different from the puncture speed or the pullout speed described above.

Figure 12:
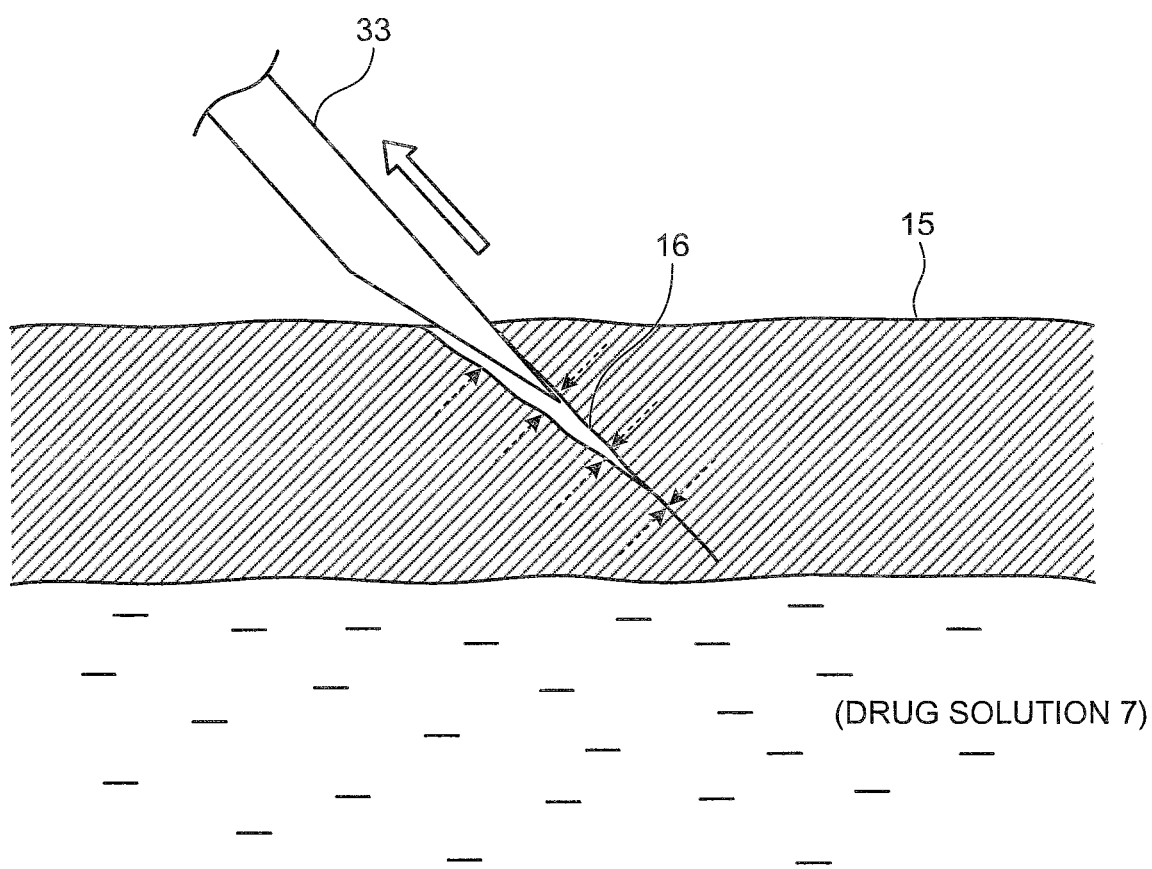
FIG. 12 is a schematic diagram in which a puncture hole contracts due to a slow-speed pullout of the injection needle.

An effect of Step S104, which is performed by the capsule medical apparatus, for the puncture hole in the affected area is described in detail. The affected area is an example of the internal region of interest. FIG. 12 is a schematic diagram in which the injection needle is pulled out from the affected area at the low pullout speed so as to seal the puncture hole.

As shown in FIG. 12, the injection needle 33 that has been used for injecting the drug solution 7 into the affected area 15 is gradually moved by the driving unit 36 to the outside of the affected area 15 at the pullout speed that is lower than the speed of the contraction of the affected area 15. The time required for the contraction of the affected area 15 (i.e., living tissue) to seal the puncture hole 16 is elapsed before the injection needle 33 is completely pulled out from the puncture hole 16. As the injection needle 33 is moved, the opening size of the puncture hole 16 gradually contracts due to the contraction of the affected area 15 so that the puncture hole 16 is sealed when the injection needle 33 is completely pulled out.

As described, the puncture hole 16 is sealed after the injection needle 33 is pulled out from the affected area 15 at the lower pullout speed. Therefore, even after the injection needle 33 is completely pulled out from the puncture hole 16, the drug solution 7 does not leak from the puncture hole 16 and remains inside the affected area 15. As a result, the drug solution 7 inside the affected area 15 does not spread over internal regions other than the affected area 15 inside the subject.

As described above, in the third embodiment of the present invention, the control unit controls the driving unit so that the injection needle is pulled out from the puncture hole at the pullout speed that is lower than the speed of the contraction of the internal region and thereby the puncture hole is sealed. Other configurations are substantially the same as those of the first embodiment. In this way, the time required for the contraction of living tissue to seal the puncture hole in the internal region that is made by the injection needle is guaranteed before the injection needle is completely pulled out from the internal region. The capsule medical apparatus can provide the same operational effects as those of the first embodiment using a fewer number of components, whereby the capsule medical apparatus can be produced easily with less production cost.

In the capsule medical apparatus, the injection needle protrudes from the capsule casing in a manner such that the longitudinal direction of the injection needle is oblique to the radial direction of the capsule casing. Thus, the injection needle can puncture the internal region in a manner such that the injection needle makes an acute angle with the surface (i.e., wall surface of organs) of the internal region inside the subject. In this way, the length of the puncture hole becomes longer than the case where the injection needle punctures the internal region vertically, whereby the drug solution is still less likely to leak from the puncture hole.

Further, the injection needle punctures the internal region with the front opening of the injection needle directed toward the internal region that is punctured. In this way, the front opening (a hole of the needle) of the injection needle that punctures the internal region is directed toward the living tissue of interest. Thus the drug solution can be easily injected into the living tissue of interest.

A first variation of the third embodiment of the present invention is described below. In the third embodiment described above, the injection needle protrudes from the capsule casing 2 with the front opening of the injection needle directed toward the internal region that is to be punctured. In the first variation of the third embodiment, the front opening of the injection needle 33 is directed toward the internal region when the injection needle 33 punctures the internal region, and the front opening of the injection needle 33 is directed in a reverse direction when pulled out from the internal region.

Figure 13:
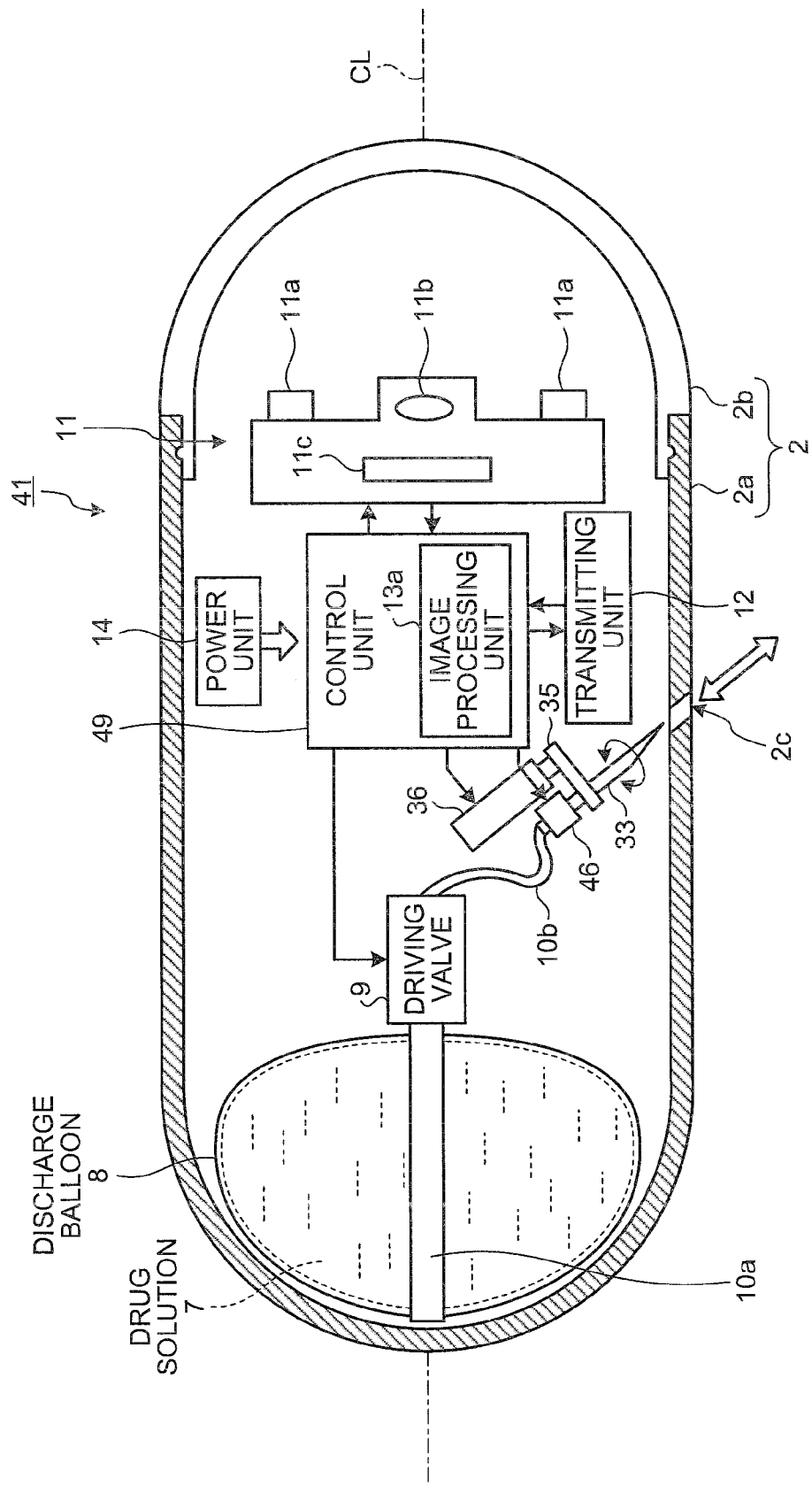
FIG. 13 is a schematic diagram of an exemplary configuration of a capsule medical apparatus according to a first variation of the third embodiment of the present invention.

FIG. 13 is a schematic diagram of an exemplary configuration of a capsule medical apparatus according to a first variation of the third embodiment of the present invention. As shown in FIG. 13, a capsule medical apparatus 41 according to the first variation of the third embodiment includes a control unit 49 instead of the control unit 39 of the capsule medical apparatus 31 according to the third embodiment described above. The capsule medical apparatus 41 further includes a rotation driving unit 46 that rotates the injection needle 33 around the longitudinal direction of the injection needle 33. Other configurations are the same as those of the third embodiment, and same numerals are attached to same components.

The rotation driving unit 46 can be a rotation actuator or the like and is attached to, for example, the injection needle 33 near the rear end of the injection needle 33. The rotation driving unit 46 rotates the injection needle 33 around the longitudinal direction of the injection needle 33 under the control of the control unit 49. The rotation driving unit 46 determines the directions of the front opening of the injection needle 33 when the injection needle 33 punctures the internal region and when it is pulled out from the internal region.

The control unit 49 controls actuation of the rotation driving unit 46 and thus controls the directions of the front opening of the injection needle 33 when the injection needle punctures the internal region and when it is pulled out from the internal region. Specifically, when the injection needle 33 punctures the internal region, the control unit 49 controls the rotation driving unit 46 so that the front opening of the injection needle 33 is directed toward the internal region. When the injection needle 33 is pulled out from the internal region, the control unit 49 controls the rotation driving unit 46 so that the front opening of the injection needle 33 is directed toward the reversed direction. The reversed direction above is reversed to the direction of the front opening of the injection needle 33 that punctures the internal region. Specifically, the front opening of the injection needle 33 is first directed toward the inside of the internal region (where the drug solution is to be injected) and then directed toward the capsule casing 2 (the outside of the punctured region). Other than the function to control the rotation driving unit 46, the control unit 49 has the same functions as those of the control unit 39 of the capsule medical apparatus 31 according to the third embodiment described above.

Figure 14:
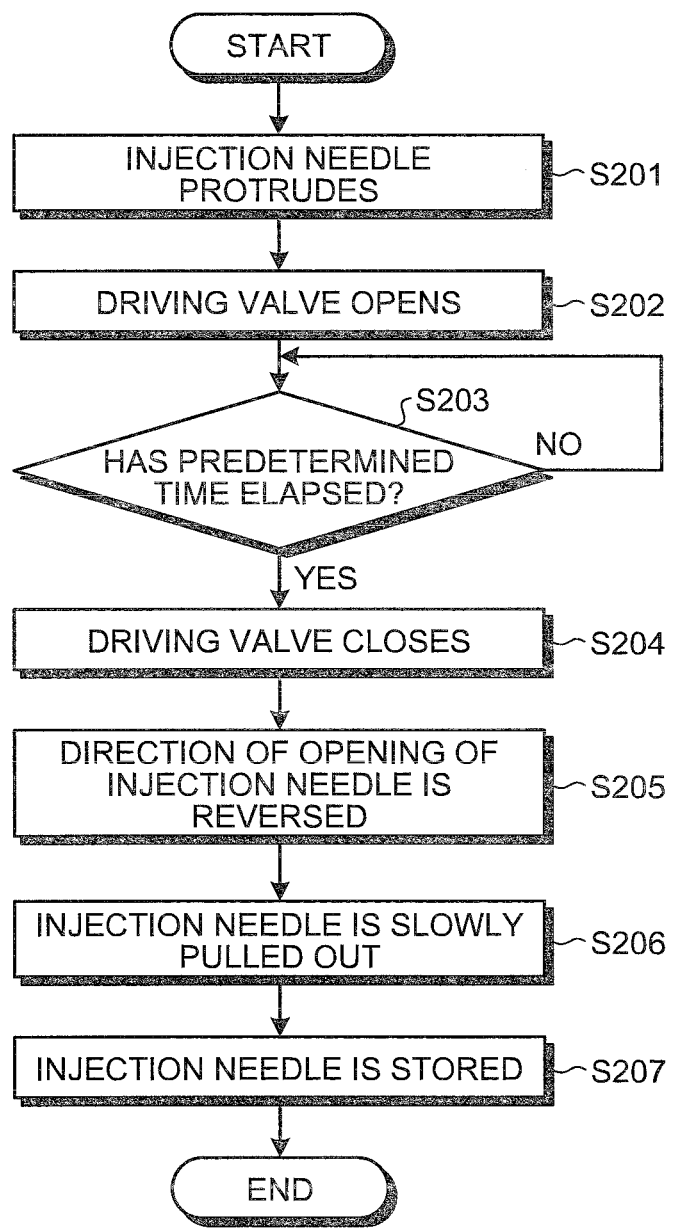
FIG. 14 is a flowchart of a procedure in which the capsule medical apparatus according to the first variation of the third embodiment of the present invention makes an injection into an internal region.

The following describes a series of operations that are performed by the capsule medical apparatus 41 between when the injection needle 33 protrudes toward the internal region and when the injection needle 33 is pulled out from the internal region into which the injection has been performed and is stored into the capsule casing 2. FIG. 14 is a flowchart of a procedure in which the capsule medical apparatus according to the first variation of the third embodiment of the present invention makes an injection into an internal region. The capsule medical apparatus 41 according to the first variation of the third embodiment adjusts the injection needle 33 to hit an internal region of interest, e.g., an affected area, inside the subject when reaching the internal region of interest, similarly to the capsule medical apparatus 31 according to the third embodiment described above.

When the capsule medical apparatus 41 reaches the internal region of interest, e.g., the affected area, inside the subject, the control unit 49 performs, based on the control signal from the external apparatus described above, the following processes as shown in FIG. 14. The control unit 49 first controls the rotation driving unit 46 so that the front opening of the injection needle 33 is directed toward the internal region. Further, the control unit 49 controls the driving unit 36 so that the injection needle 33 protrudes from the capsule casing at a predetermined puncture speed (Step S201). At Step S201, the rotation driving unit 46 rotates the injection needle 33 so that the front opening of the injection needle is directed toward the internal region that is to be punctured. The control unit 49 can determine the direction of the front opening of the injection needle 33 based on the rotation of the rotation driving unit 46. When the front opening of the injection needle is not directed toward the internal region that is to be punctured, the control unit 49 controls the rotation driving unit 46 so that the front opening of the injection needle 33 is directed toward the internal region. When the front opening of the injection needle 33 is directed toward the internal region that is to be punctured, the control unit 49 controls the rotation driving unit 46 so that the injection needle 33 is maintained as it is.

At Step S201, under the control of the control unit 49, the driving unit 36 makes the injection needle 33 protrude from the capsule casing 2, and the injection needle 33 then punctures the internal region at the puncture speed that is controlled by the control unit 49, similarly to the third embodiment described above. The injection needle 33 punctures the internal region with the front opening directed toward the internal region.

Then, similarly to Step S102 shown in FIG. 11, the control unit 49 makes the driving valve 9 open while the injection needle 33 remains in the internal region (Step S202). Next, similarly to Step S103 shown in FIG. 11, the control unit determines whether a predetermined time has elapsed since the driving valve 9 opens itself while the injection needle 33 remains in the internal region (Step S203). When the control unit 49 determines that the predetermined time has not elapsed at Step S203 (Step S203, No), the control unit 49 repeats this Step S203. On the other hand, when the control unit 49 determines that the predetermined time has elapsed at Step S203 (Step S203, Yes), the control unit 49 makes the driving valve 9 close similarly to Step S104 shown in FIG. 11 (Step S204).

When the driving valve 9 is closed as described (i.e., when the injection operation that injects the drug solution 7 using the discharge balloon 8 is completed), the control unit 49 controls the rotation driving unit 46 so that the direction of the opening of the injection needle 33 is reversed (Step S205). At Step S205, the control unit 49 controls the rotation driving unit 46 so that the direction of the front opening of the injection needle 33 that has punctured the internal region is reversed. The rotation driving unit 46 rotates the injection needle 33 that punctures the internal region around the longitudinal direction of the injection needle 33 so that the front opening of the injection needle 33, which has been directed toward the inside of the internal region (where the drug solution is to be injected), is directed in the capsule medical apparatus 2 (the outside of the punctured region).

The control unit 49 controls the rotation driving unit 46 so that the direction of the front opening of the injection needle 33 is maintained as it is. Similarly to Step S105 in FIG. 11, the control unit 49 at the same time controls the driving unit 36 so that the injection needle 33 is pulled out at a low speed from the internal region into which the injection has been performed (Step S206). In this way, the time required for the contraction of the internal region (i.e., living tissue) to seal the puncture hole that is made by the injection needle 33 in the internal region is guaranteed.

Then, similarly to Step S106 shown in FIG. 11, the control unit 49 controls the driving unit 36 so that the injection needle 33 is stored inside the capsule casing 2 (Step S207). Thus, the series of operations (the procedure) are completed.

At Steps S205 and S206, the control unit 49 may control the rotation driving unit 46 and the driving unit 36 to do the both operations at the same time: reversing the direction of the front opening of the injection needle 33 that punctures the internal region, and pulling out the injection needle from the internal region at the low speed. The front opening of the injection needle 33 is required to be directed toward the capsule casing 2 by the time when the injection needle 33 is pulled out and exposed to the outside the puncture hole in the internal region. Therefore, the front opening of the injection needle 33 that is still in the puncture hole may be directed in any direction.

Figure 15A:
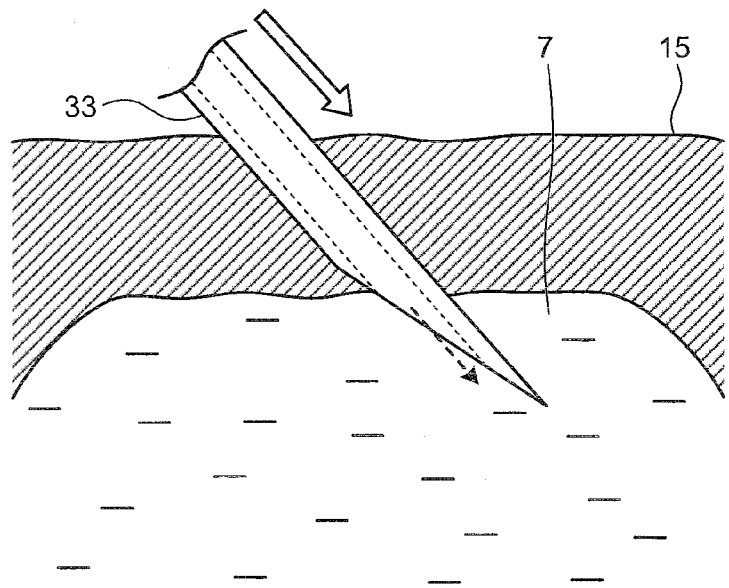
FIGS. 15A and 15B are schematic diagrams in which a puncture hole contracts due to a slow-speed pullout of the injection needle with the opening front end thereof directed toward the capsule casing.
Figure 15B:
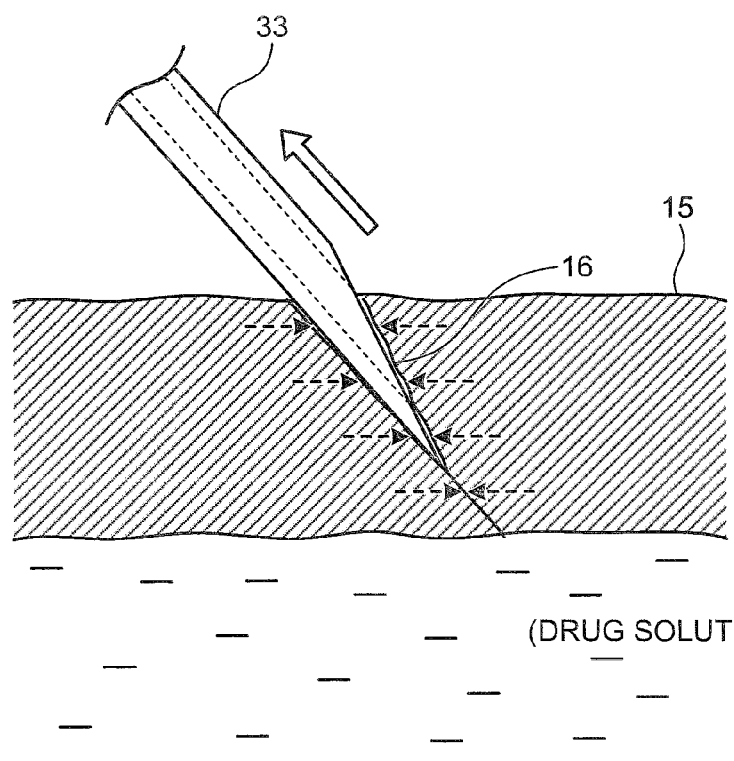

An effect caused to the puncture hole in the affected area through Steps S205 and S206 performed by the capsule medical apparatus 41 is described below in detail. The affected area is an example of the internal region of interest. FIGS. 15A and 15B are schematic diagrams in which the injection needle is pulled out from the affected area at a low pullout speed with the front opening directed toward the capsule casing so as to seal the puncture hole. The injection needle 33 that punctures the affected area is in the same state as the third embodiment described above.

AS shown in FIG. 15A, when the injection needle 33 completes the injection of the drug solution 7 into the affected area 15, the rotation driving unit 46 reverses the direction of the front opening of the injection needle 33 that punctures the affected area 15 so that the front opening is directed toward the outside of the affected area 15 (toward the capsule casing 2). Then, the driving unit 36 moves the injection needle 33 gradually to the outside of the affected area 15 at the pullout speed that is lower than the speed of the contraction of the affected area 15.

The injection needle 33 punctures the internal region in a manner such that the injection needle 33 makes an acute angle with the surface of the internal region (wall surface of organs) inside the subject, i.e., that the injection needle 33 is oblique to the surface. The injection needle 33 is completely pulled out from the puncture hole 16 in the affected area 15 with the front opening thereof directed toward the outside of the affected area 15 similarly to the pullout shown in FIG. 15B. Thus, the front opening is exposed relatively in an early stage of the pullout. As described, the driving unit 36 pulls out the injection needle 33 from the puncture hole 16 with the front opening thereof directed toward the outside of the affected area 15 so that the outer diameter of the part of the injection needle 33 that still remains inside the puncture hole can contract relatively in the early stage. As a result, the opening size of the puncture hole 16 can contract due to the contraction of the affected area 15 more easily and earlier compared to a case where the front opening of the injection needle 33 is directed toward the inside of the affected area 15 so that the puncture hole 16 is sealed.

When the puncture hole 16 in the affected area 15 is sealed as described, the drug solution 7 do not leak from the puncture hole 16 and remains inside the affected area 15 even after the injection needle 33 is completely pulled out from the puncture hole 16. As a result, the drug solution 7 inside the affected area 15 do not spread over internal regions other than the affected area 15 inside the subject.

As described, in the first variation of the third embodiment of the present invention, the rotation driving unit rotates the injection needle around the longitudinal direction of the injection needle so that the injection needle is pulled out with the front opening thereof directed toward the outside of the punctured region (toward the capsule casing). Other configurations are the same as those of the third embodiment. Therefore, the capsule medical apparatus can provide the same operation effects as those of the third embodiment described above. Further, the outer diameter of the part of the injection needle that remains inside the internal region can contract relatively in the early stage using the capsule medical apparatus, whereby the puncture hole in the internal region can be sealed more easily and earlier.

A fourth embodiment of the present invention is described. In the first embodiment described above, the injection needle 3 that punctures the internal region is heated and contracts so that the puncture hole in the internal region that is made by the injection needle is sealed. In contrast, in the fourth embodiment, living tissue of the internal region, which is punctured by the injection needle, is cauterized so as to seal the puncture hole in the internal region.

Figure 16:
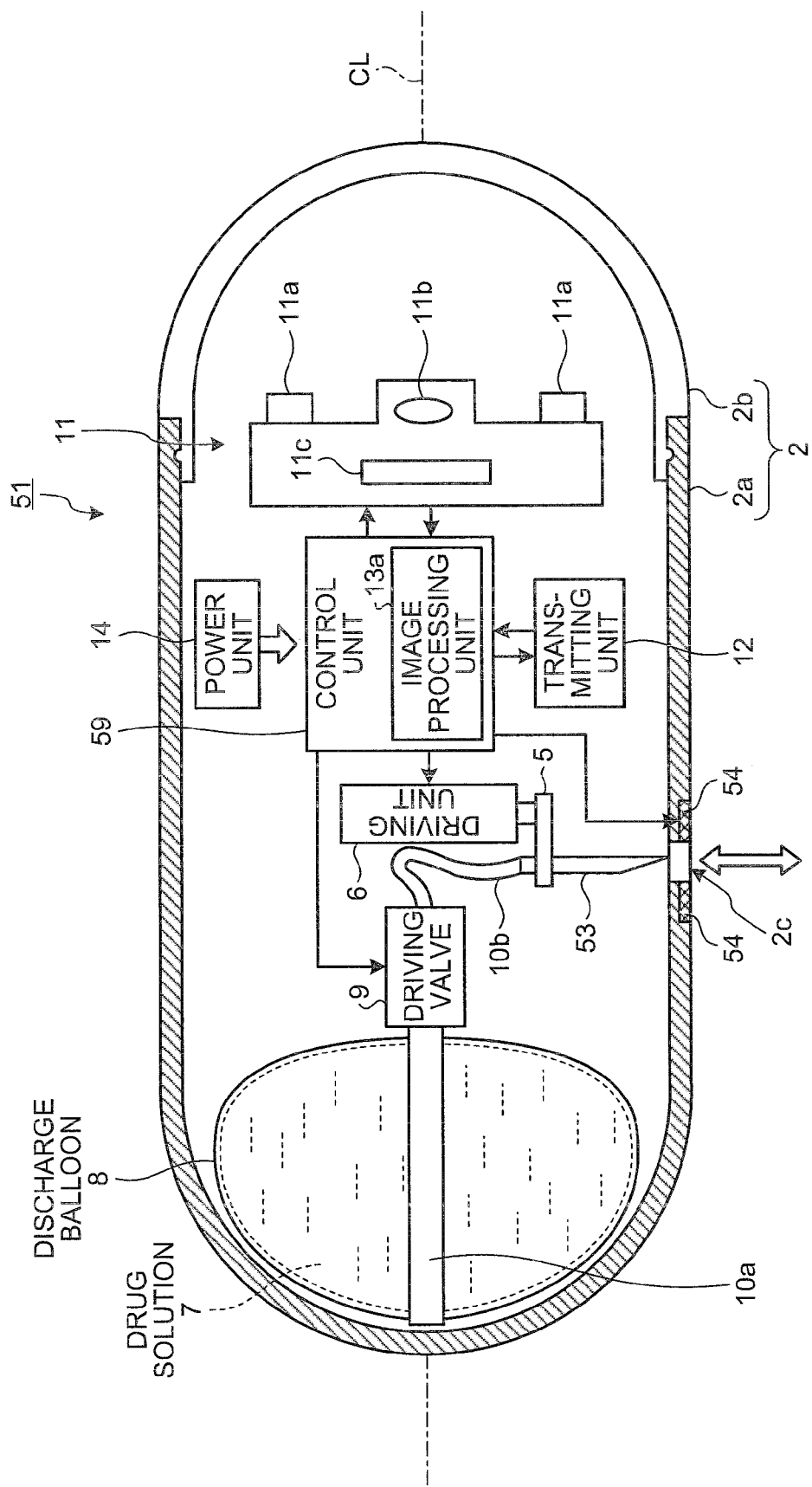
FIG. 16 is a schematic diagram of an exemplary configuration of a capsule medical apparatus according to a fourth embodiment of the present invention.

FIG. 16 is a schematic diagram of an exemplary configuration of a capsule medical apparatus according to the fourth embodiment of the present invention. As shown in FIG. 16, a capsule medical apparatus 51 according to the fourth embodiment includes an injection needle 53, a cauterization unit 54, and a control unit 59 instead of the injection needle 3, the heater 4, and the control unit 13 of the capsule medical apparatus 1 according to the first embodiment described above. Other configurations are the same as those of the first embodiment, and same numerals are attached to same components.

The injection needle 53 is a hard hollow needle that is made of metals or the like. The injection needle 53 does not contract due to the contraction of an internal region that is punctured by the injection needle 53. The tube 10b is attached to the rear end of the injection needle 53. The injection needle 53 is communicated with the driving valve 9 through the tube 10b. The supporter 5 is attached to the injection needle 53 near the rear end of the injection needle 53. The injection needle 53 has a hollow structure similar to that of the injection needle 3 according to the first embodiment.

The cauterization unit 54 functions as a sealing unit that is an exemplary leak prevention unit. The cauterization unit 54 is located near the opening 2c in the capsule casing 2 and surrounds the opening 2c from which the injection needle 53 protrudes. The cauterization unit 54 cauterizes a puncture hole in an internal region that is made by the injection needle 53. The cauterization unit 54 includes a resistance heating device or the like as a cauterization function unit that cauterizes living tissue. The cauterization unit 54 is exposed to the outside of the capsule casing 2 and touches the internal region that is punctured by the injection needle 53. The cauterization unit 54 then cauterizes the living tissue around the injection needle 53 that punctures the internal region using the power supplied from the control unit 59, so that the puncture hole in the internal region made by the injection needle 53 is sealed. In the fourth embodiment, when the puncture hole in the internal region is in a sealed state, the living tissue around the puncture hole hardens due to the cauterization process performed by the cauterization unit 54 so that the puncture hole is sealed.

The control of the control unit 59 controls the cauterization unit 54 so that the living tissue around the injection needle 53 that punctures the internal region is cauterized and thereby so that the puncture hole is sealed. The control unit 59 can control actuation of the cauterization process of the cauterization unit 54 by changing the instant when the power starts to be supplied to the cauterization unit 54. The control unit 59 can further control temperature and duration of cauterization by changing the amount and duration of power supplied to the cauterization unit 54. Besides the function to control the cauterization unit 54, the control unit 59 has the same functions as those of the control unit 13 of the capsule medical apparatus 1 according to the first embodiment.

Figure 17A:
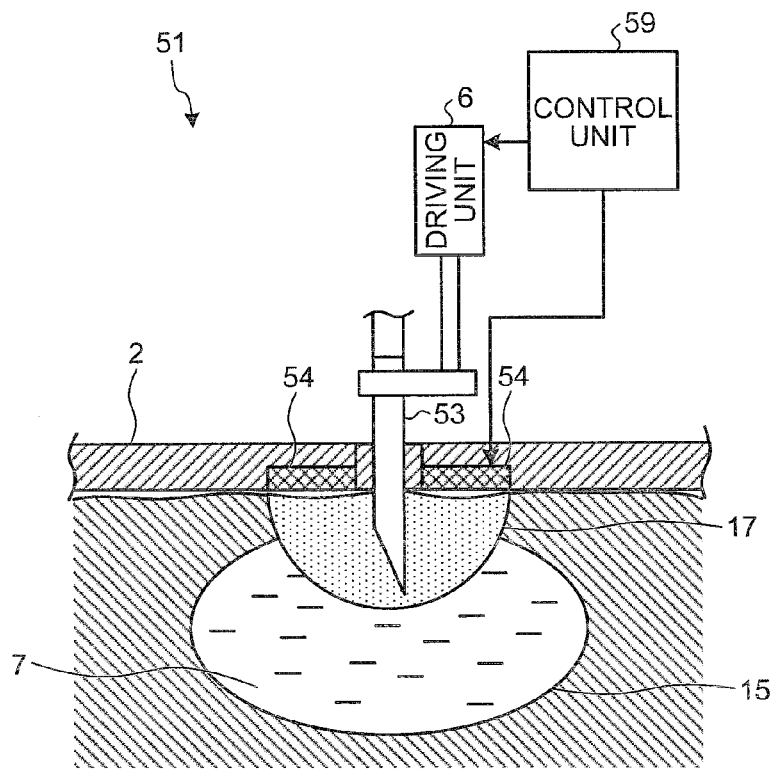
FIGS. 17A and 17B are schematic diagrams in which a puncture hole of an internal region contracts due to a cauterization process performed on living tissue around the injection needle.
Figure 17B:
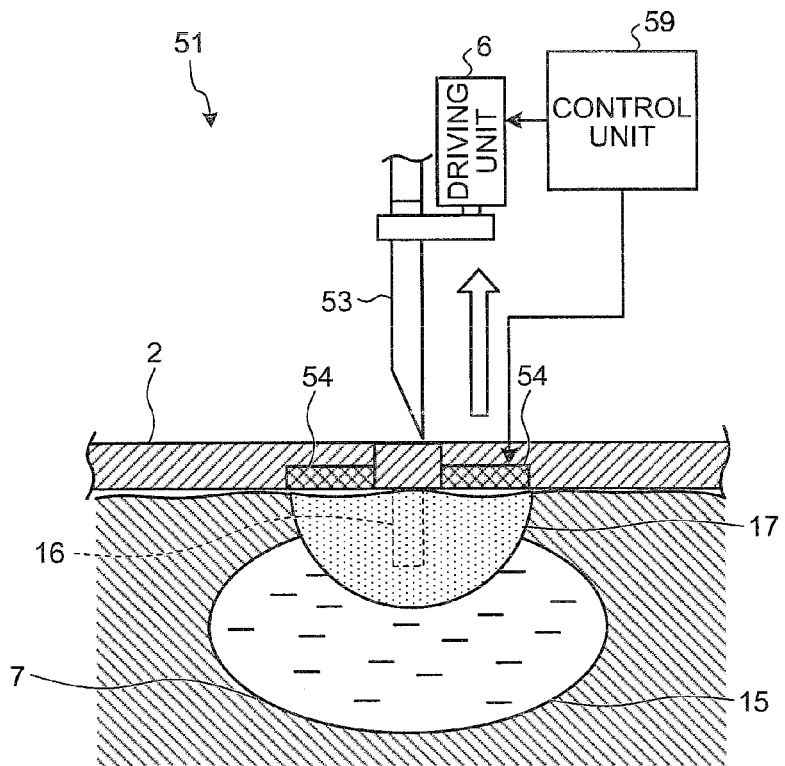

An operation of the capsule medical apparatus 51 according to the fourth embodiment of the present invention is described in more detail. As an example of such an operation, the capsule medical apparatus 51 injects a drug solution into the affected area, which is an example of an internal region of interest, inside the subject. FIGS. 17A and 17B are schematic diagrams in which the puncture hole in the internal region is sealed due to the cauterization process performed on the living tissue around the injection needle. In the operation described below, the capsule medical apparatus 51 seals the puncture hole 16 in the affected area 15 that is made by the injection needle 53 with reference to FIGS. 17A and 17B. Other than the operation that seals the puncture hole 16 in the affected area 15 that is made by the injection needle 53, the capsule medical apparatus 51 according to the fourth embodiment performs the same operations as those of the capsule medical apparatus 1 according to the first embodiment described above.

After the capsule medical apparatus 51 injects the drug solution 7 into the affected area 15 through the injection needle 53 that punctures the affected area 15, the cauterization unit 54 cauterizes living tissue 17 around the injection needle 53 for a predetermined time while the driving unit 6 keeps the injection needle 53 remaining in the affected area 15, under the control of the control unit 59. These processes are shown in FIG. 17A. In more detail, the control unit 59 supplies power to the cauterization unit 54 for a predetermined time when the driving valve 9 closes itself.

The cauterization unit 54 touches the affected area 15 that is punctured by the injection needle 53 and cauterizes the living tissue 17 around the injection needle 53 that punctures the internal region for the predetermined time. The living tissue 17 that has been cauterized by the cauterization unit 54 for the predetermined time hardens and seals the puncture hole 16 in the affected area 15 that is made by the injection needle 53. The living tissue 17 that has hardened completely blocks the puncture hole 16 so that the inside of the affected area 15 (where the drug solution 7 remains) and the outside of the puncture hole 16 (where the capsule medical apparatus 51 is located) are not communicated.

In a predetermined time after the cauterization unit 54 starts the cauterization process, the control unit 59 stops supplying power to the cauterization unit 54. Thus, the cauterization process of the cauterization unit 54 is completed. As shown in FIG. 17B, the control unit 59 then pulls out the injection needle 53 from the affected area 15 and stores the injection needle 53 inside the capsule casing 2 similarly to the first embodiment described above.

When the injection needle 53 is pulled out from the puncture hole (the site of puncture) 16 in the affected area 15, the puncture hole 16 is sealed by the living tissue 17 that has hardened. Therefore, the drug solution 7 does not leak from the puncture hole 16 and remains in the affected area 15 even after the injection needle 53 is pulled out. As a result, the drug solution 7 inside the affected area 15 do not spread over internal regions other than the affected area 15 inside the subject.

As described above, in the fourth embodiment of the present invention, the cauterization unit is exposed outside the capsule casing. The cauterization unit cauterizes living tissue around the injection needle that punctures an internal region so that the puncture hole in the internal region that is made by the injection needle is sealed. Other configurations are the same as those of the first embodiment described above. As a result, the puncture hole in the internal region can be completely sealed by the living tissue that has been cauterized by the cauterization unit and has hardened. The capsule medical apparatus can provide the same operational effects as those of the first embodiment. Furthermore, the injected liquid can be prevented from leaking from the puncture hole more accurately using the capsule medical apparatus.

A first variation of the fourth embodiment of the present invention is described. In the fourth embodiment described above, the cauterization unit 54 is arranged on the outer surface of the capsule casing 2 (specifically, near the opening 2c, from which the injection needle 53 protrudes). The cauterization unit 54 cauterizes living tissue around the injection needle 53 that has punctured and remains in an internal region so that the puncture hole 16 is sealed. In contrast, in the first variation of the fourth embodiment, the injection needle has a cauterization function. The injection needle punctures an internal region and then cauterizes the puncture hole using its own cauterization function so that the puncture hole is sealed.

Figure 18:
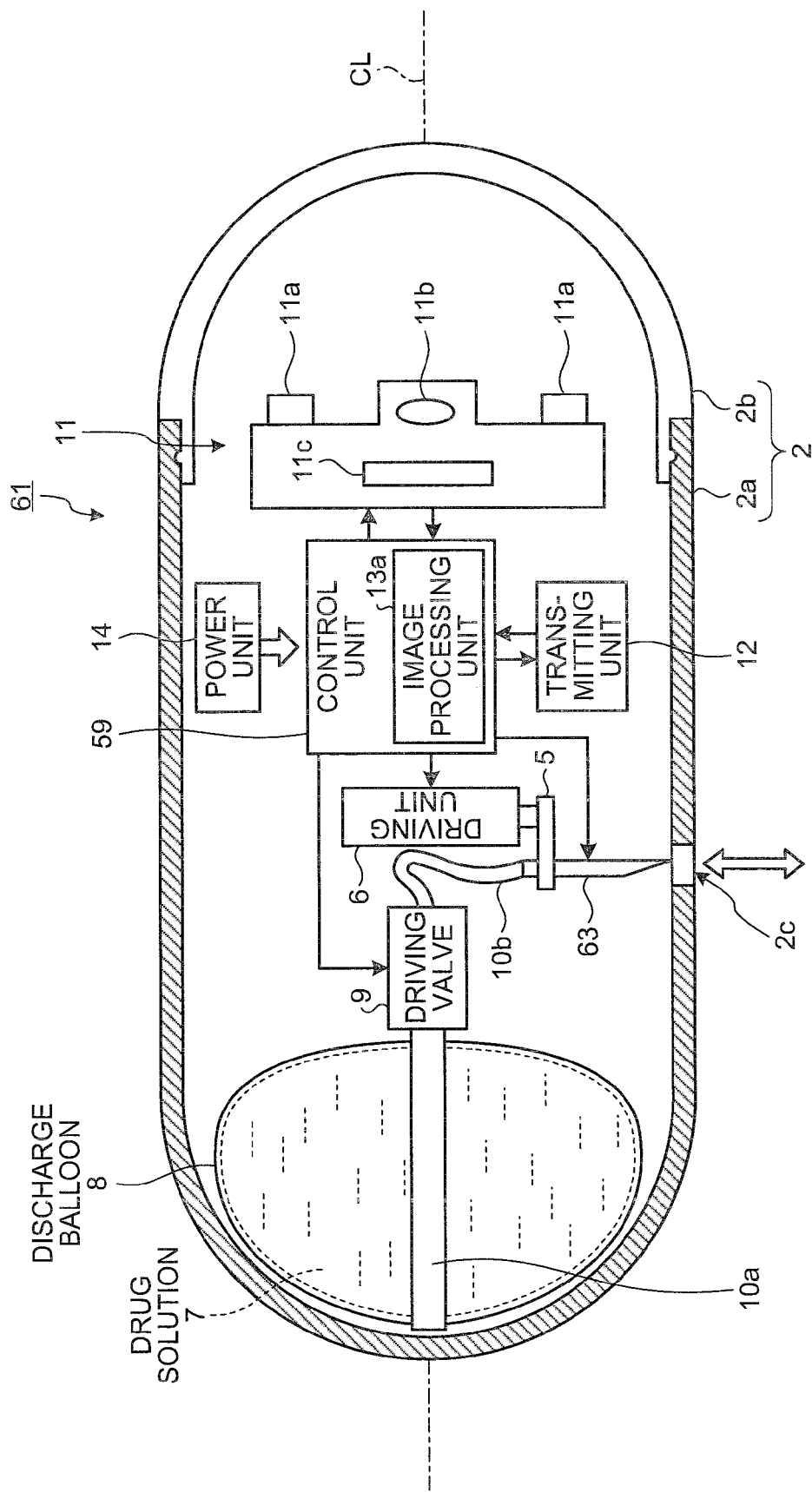
FIG. 18 is a schematic diagram of an exemplary configuration of a capsule medical apparatus according to a first variation of the fourth embodiment of the present invention.

FIG. 18 is a schematic diagram of an exemplary configuration of a capsule medical apparatus according to the first variation of the fourth embodiment of the present invention. As shown in FIG. 18, a capsule medical apparatus 61 according to the first variation of the fourth embodiment includes an injection needle 63 that has a cauterization function to cauterize living tissue, instead of the injection needle 53 of the capsule medical apparatus 51 according to the fourth embodiment described above. The capsule medical apparatus 61 does not include the cauterization unit 54. In the capsule medical apparatus 61, the control unit 59 supplies power to the injection needle 63 instead of the cauterization unit 54 and thus controls the cauterization of living tissue performed by the injection needle 63. Other configurations are the same as those of the fourth embodiment, and same numerals are attached to same components.

The injection needle 63 has a function as a hollow needle through which a liquid, e.g., a drug solution, is injected into an internal region. The injection needle 63 further includes a function as a sealing unit that is an exemplary leak prevention unit. The injection needle 63 cauterizes a puncture hole in an internal region so that the puncture hole is sealed. In detail, the injection needle 63 is a hard hollow needle that includes a resistance heating device that generates heat when power is supplied to the device. The injection needle 63 does not contract due to the contraction of the internal region that is punctured by the injection needle 63. The tube 10b is attached to the rear end of the injection needle 63 and is communicated with the driving valve 9 by the tube 10b. The supporter 5 is attached to the injection needle 63 near the rear end of the injection needle 63. The injection needle 63 is driven by the driving unit 6 and protrudes from the capsule casing 2 similarly to the injection needle 53 according to the fourth embodiment described above. The injection needle 63 is hollow similarly to the injection needle 53 according to the fourth embodiment described above. The tube 10b is made of heat-resistant materials and thus is resistant to heat generated by the injection needle 63.

In the capsule medical apparatus 61 according to the first variation of the fourth embodiment, the control unit 59 controls the injection needle 63 so that the living tissue around the injection needle 63 that has punctured and remains in the internal region is cauterized and thereby the puncture hole is sealed. The control unit 59 can control actuation of the cauterization process of the injection needle 63 that cauterizes the living tissue by changing the instant when power is supplied to the injection needle 63, similarly to the cauterization unit 54 according to the fourth embodiment described above. The control unit 59 further controls temperature and duration of cauterization of the living tissue by changing the amount and duration of power supplied to the injection needle 63.

The injection needle 63, which also has the cauterization function, cauterizes the living tissue around the puncture hole in the internal region for the predetermined time while the injection needle 63 remains in the internal region of interest, e.g., the affected area 15. In other words, the injection needle 63 cauterizes the living tissue around the injection needle 63 that punctures the internal region. The injection needle 63 performs the cauterization using the power supplied from the control unit 59 for the predetermined time. The living tissue around the puncture hole that is cauterized by the injection needle 63 hardens so that the puncture hole in the internal region is sealed, similarly to the fourth embodiment described above. The living tissue that has hardened completely blocks communication between the inside of the internal region (where the liquid is injected) and the outside of the puncture hole (where the capsule medical apparatus is located). Because the puncture hole in the internal region is sealed, the drug solution 7 does not leak from the puncture hole even after the injection needle 63 and remains inside the internal region.

As described above, in the first variation of the fourth embodiment of the present invention, the injection needle functions as a hollow needle that injects the drug solution or the like into the internal region and also as a cauterization unit that cauterizes the living tissue around the puncture hole. The injection needle cauterizes the living tissue around the puncture hole in the internal region punctured by the injection needle and thus the living tissue hardens so that the puncture hole is sealed. Other configurations are the same as those of the fourth embodiment. The capsule medical apparatus can provide the same operational effects as those of the fourth embodiment described above. The capsule medical apparatus includes a less number of components so that the capsule medical apparatus can be produced easily with less production cost.

A second variation of the fourth embodiment of the present invention is described. In the fourth embodiment, the cauterization unit 54 is arranged on the outer surface of the capsule casing 2 (specifically, near the opening 2c, from which the injection needle 53 protrudes). The cauterization unit 54 cauterizes living tissue around the injection needle 53 that has punctured and remains in the internal region so that the puncture hole is sealed. In contrast, in the second variation of the fourth embodiment, the capsule medical apparatus includes a cauterization unit that can protrude from the capsule casing 2. Such a cauterization unit touches the internal region and cauterizes the living tissue around the injection needle so that the puncture hole in the internal region is sealed.

FIG. 19 is a schematic diagram of an exemplary unit of a capsule medical apparatus according to the second variation of the fourth embodiment of the present invention. As shown in FIG. 19, a capsule medical apparatus 71 according to the second variation of the fourth embodiment includes a cauterization unit 74 that can protrude instead of the cauterization unit 54 of the capsule medical apparatus 51 according to the fourth embodiment described above. The capsule medical apparatus 71 includes a control unit 79 instead of the control unit 59. The capsule medical apparatus includes a supporter 75 that supports the cauterization unit 74, and a driving unit 76 that makes the cauterization unit 74 protrude from the capsule casing 2. Other configurations are the same as those of the fourth embodiment, and same numerals are attached to same components.

The cauterization unit 74 functions as a sealing unit that is an exemplary leak prevention unit. The cauterization unit 74 cauterizes a puncture hole in an internal region that is made by the injection needle 53. The cauterization unit 74 can be a resistance heating device that generates heat when power is supplied thereto. The cauterization unit 74 is a cylinder shape through which the injection needle 53 can be inserted. The cauterization unit 74 is supported by the supporter 75. The driving unit 76 is connected with the supporter 75 and makes the cauterization unit 74 protrude from the opening 2c in the capsule casing 2. The cauterization unit 74 cauterizes the living tissue in the internal region. In other words, the cauterization unit 74 cauterizes living tissue around the injection needle 53 (i.e., living tissue around the puncture hole) that punctures the internal region. The cauterization unit 74 performs the cauterization using the power supplied from the control unit 79. Thus, the puncture hole in the internal region that is made by the injection needle 53 is sealed by the cauterization unit 74, similarly to the fourth embodiment described above.

The supporter 75 is fixed being near the rear end of the cauterization unit 74. The supporter 75 supports the cauterization unit 74 in a manner such that the injection needle 53 is inserted into the cauterization unit, which is cylinder-shaped, and such that the cauterization unit 74 can protrude from the opening 2c in the capsule casing 2. The supporter 75 is connected with the driving unit 76.

The driving unit 76 can operate independently of the driving unit 6 that protrudes the injection needle 53. The driving unit 76 functions as a cauterization driving unit that protrudes the cauterization unit 74 from the opening 2c in the capsule casing 2. The driving unit 76 can be a linear actuator or the like. The driving unit 76 reciprocates the cauterization unit 74 along a direction in which the injection needle 53 is protruded (i.e., a direction in the arrow drawn with a thick line in FIG. 19) using the supporter 75 described above. The driving unit 76 is controlled by the control unit 79 and makes the cauterization unit 74 protrude from the capsule casing 2 with the injection needle 53. The cauterization unit 74 then touches the internal region that is to be punctured. The driving unit 76 keeps the cauterization unit 74 in contact with the internal region while the cauterization unit 74 cauterizes the living tissue around the injection needle 53 that has punctured and remains in the internal region. The cauterization unit 74, which is driven by the driving unit 76, can touch the internal region before the injection needle 53 punctures the internal region or can do so after the injection needle 53 punctures the internal region. After the cauterization unit 74 cauterizes the living tissue around the puncture hole in the internal region, the driving unit 76 stores the cauterization unit 74 inside the capsule casing 2, under the control of the control unit 79.

The control unit 79 controls the cauterization unit 74 so that the living tissue around the injection needle 53 that punctures the internal region is cauterized and thereby the puncture hole is sealed. The control unit 79 controls the instant of the cauterization of the cauterization unit 74 by changing an instant when power is supplied to the cauterization unit 74, similarly to the control of the cauterization unit 54 according to the fourth embodiment described above. The control unit 79 controls temperature and duration of the cauterization of the cauterization unit 74 by changing an amount and duration of power supplied to the cauterization unit 74. The control unit 79 controls the driving unit 6 so that the injection needle 53 protrudes, and the control unit 79 controls the driving unit 76 so that the cauterization unit 74 protrudes. The control unit 79 controls the driving unit 76 so that the cauterization unit 74 is stored inside the capsule casing 2 after the cauterization unit 74 has cauterized the living tissue around the puncture hole in the internal region. Other than the function to control the cauterization unit 74 and the driving unit 76, the control unit 79 has the same functions as those of the control unit 59 of the capsule medical apparatus 51 according to the fourth embodiment described above.

Figure 20A:
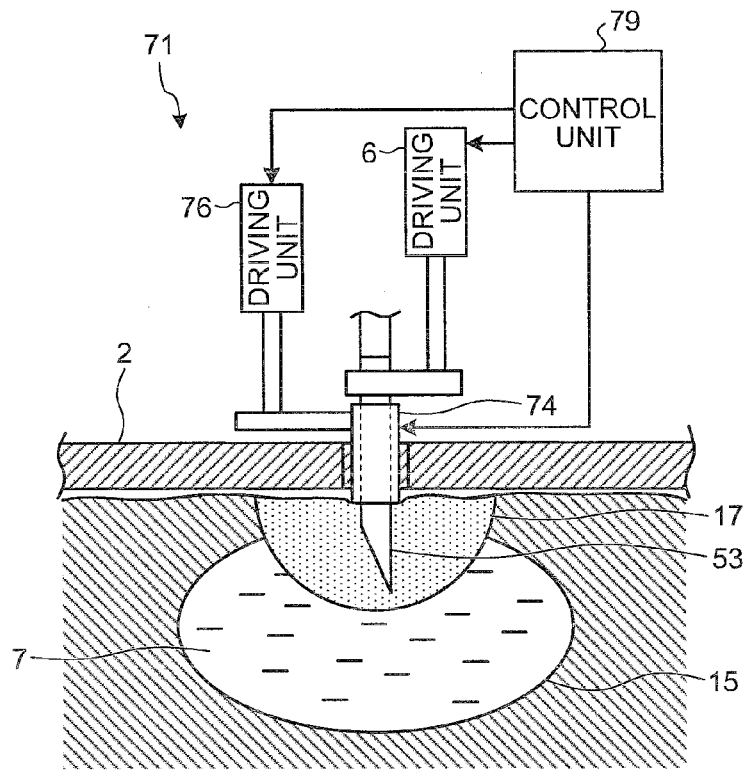
FIGS. 20A and 20B are schematic diagrams in which a puncture hole of an internal region contracts due to a cauterization process performed on living tissue around the injection needle.
Figure 20B:
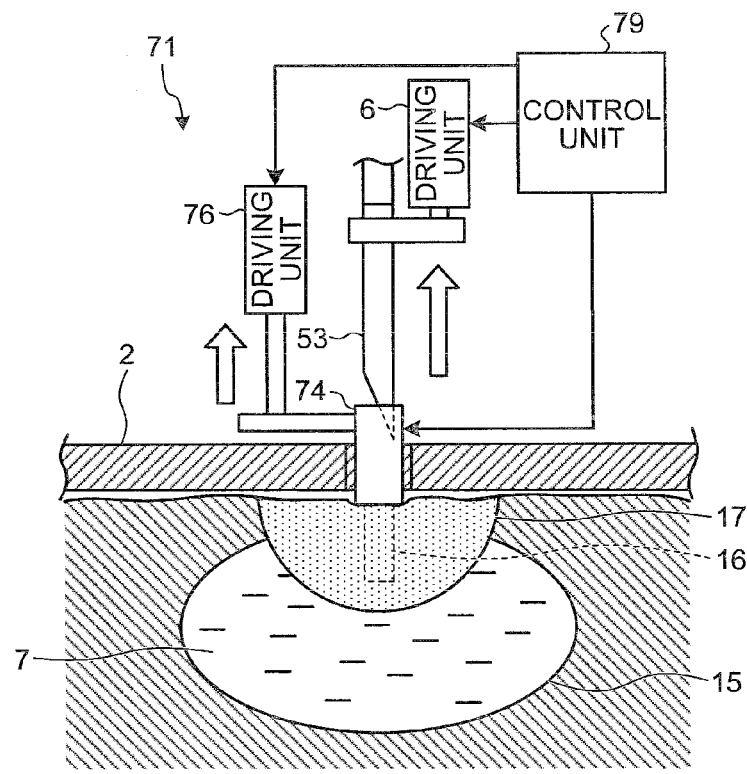

An operation of the capsule medical apparatus 71 according to the second variation of the fourth embodiment of the present invention is described in detail below. As an example of the operation, the capsule medical apparatus 71 according to the second variation of the fourth embodiment of the present invention injects the drug solution into the affected area, which is an example of the internal region of interest, inside the subject. FIGS. 20A and 20B are schematic diagrams in which the puncture hole in the internal region is sealed due to the cauterization of living tissue around the injection needle. Described below with reference to FIGS. 20A and 20B are the operations of the capsule medical apparatus 71 for sealing the puncture hole 16 that is made in the affected area 15 by the injection needle 53 and for storing the cauterization unit 74 inside the capsule casing 2. Other than the operations related to the cauterization unit 74 (i.e., operations for sealing the puncture hole and storing the cauterization unit 74), the capsule medical apparatus 71 operates in the same way as the capsule medical apparatus 51 according to the fourth embodiment described above.

When the capsule medical apparatus 71 reaches the affected area 15 inside the subject, the control unit 79 controls the driving unit 6 and the driving unit 76 so that the injection needle 53 and the cauterization unit 74 protrude together. The driving unit 76 protrudes the cauterization unit 74 in a manner such that the cauterization unit 74 does not hinder the protrusion of the injection needle 53. The cauterization unit 74 then touches the affected area 15 that is to be punctured. The driving unit 6 protrudes the injection needle 53 from the capsule casing 2 similarly to the fourth embodiment so that the injection needle 53 punctures the affected area 15. The injection needle 53 protrudes from the capsule casing 2 through the cauterization unit 74 and thus punctures the affected area 15. The control unit 79 controls the driving valve 9 similarly to the fourth embodiment so that the required amount of the drug solution 7 is injected into the affected area 15 through the injection needle 53 that punctures the internal region. Thus, the capsule medical apparatus 71 completes injecting the required amount of the drug solution 7 into the affected area 15 by the required amount.

After the capsule medical apparatus 71 injects the required amount of the drug solution 7 into the affected area 15, the control unit 79 controls the cauterization unit 74 so that the living tissue 17 around the injection needle 53 is cauterized for a predetermined time. During the cauterization, the control unit 79 controls the driving unit 6 so that the injection needle 53 remains in the affected area 15 as shown in FIG. 20A. The control unit 79 supplies power to the cauterization unit 74 for the predetermined time after the driving valve 9 closes itself.

The cauterization unit 74 touches the affected area 15 punctured by the injection needle 53 and cauterizes the living tissue 17 around the injection needle 53 that punctures the internal region, under the control of the control unit 79. The living tissue 17 that is cauterized for the predetermined time by the cauterization unit 74 hardens similarly to the fourth embodiment so that the puncture hole 16 that is made in the affected area 15 by the injection needle 53 is sealed. The living tissue 17 that has hardened blocks completely the communication between the inside of the affected area 15 (where the drug solution 7 is injected) and the outside of the puncture hole 16 (where the capsule medical apparatus 71 is located).

In a predetermined time after the cauterization unit 74 starts the cauterization process, the control unit 79 stops supplying power to the cauterization unit 74. Thus, the cauterization process of the cauterization unit 74 is completed. As shown in FIG. 20B, the control unit 79 then controls the driving unit 6 so that the injection needle 53 is pulled out from the affected area 15 and the injection needle 53 is then stored inside the capsule casing 2. To store the injection needle 53, the injection needle 53 is moved through the cauterization unit 74 into the capsule casing 2. The control unit 79 controls the driving unit 76 so that the cauterization unit 74, which has cauterized the affected area 15 (i.e., has sealed the puncture hole 16), is stored inside the capsule casing 2. The driving unit 76 may store the cauterization unit 74 inside the capsule casing 2 after the injection needle 53 is stored inside the capsule casing 2. The driving unit 76 may also store the cauterization unit 74 inside the capsule casing 2 when the injection needle 53 is stored.

When the injection needle 53 is pulled out, the puncture hole (the site of puncture) 16 is sealed by the living tissue 17 that has hardened. Therefore, the drug solution 7 does not leak from the puncture hole 16 and remains in the affected area 15 even after the injection needle 53 is pulled out from the affected area 15. Thus, the drug solution 7 inside the affected area 15 does not spread over internal regions other than the affected area 15 inside the subject.

As described above, in the second variation of the fourth embodiment of the present invention, the capsule medical apparatus includes the cauterization unit that can be driven by the driving unit and can protrude. The capsule medical apparatus protrude the cauterization unit from the capsule casing so that the cauterization unit touches the internal region that is to be punctured. The cauterization unit then cauterizes the living tissue around the injection needle that has punctured and remains in the internal region (i.e., living tissue around the puncture hole) so that the puncture hole in the internal region is sealed. Other configurations are the same as those of the fourth embodiment. The capsule medical apparatus can provide the same operational effects as those of the fourth embodiment. Furthermore, the cauterization unit can more accurately touch the internal region that is to be punctured, using the capsule medical apparatus. As a result, the capsule medical apparatus can cauterize and harden the living tissue around the puncture hole more accurately.

A fifth embodiment is described below. In the first embodiment described above, the injection needle 3 that has punctured and remains in an internal region is heated and contracts so that the puncture hole that is made in the internal region by the injection needle 3. In contract, in the fifth embodiment, the surface of the internal region that is punctured by the injection needle is extended. Then, the injection needle is pulled out while the internal region remains being extended so that the puncture hole in the internal region is sealed.

Figure 21:
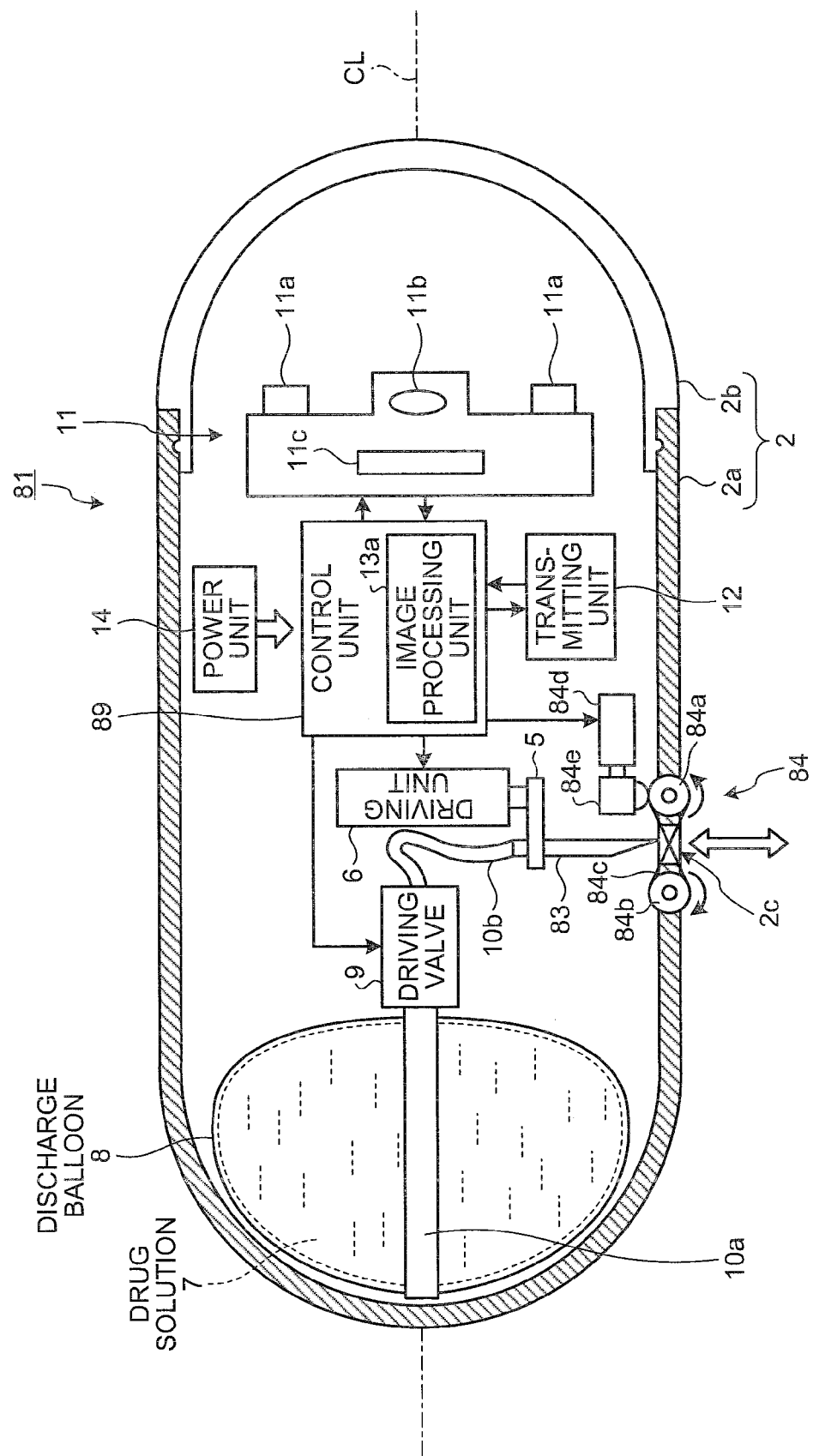
FIG. 21 is a schematic diagram of an exemplary configuration of a capsule medical apparatus according to a fifth embodiment of the present invention.

FIG. 21 is a schematic diagram of an exemplary configuration of the capsule medical apparatus according to the fifth embodiment of the present invention. As shown in FIG. 21, a capsule medical apparatus 81 according to the fifth embodiment includes an injection needle 83, a tissue-shape changing system 84, and a control unit 89 instead of the injection needle 3 of the capsule medical apparatus 1 according to the first embodiment. Other configurations are the same as those of the first embodiment, and same numerals are attached to same components.

The injection needle 83 is a hard hollow needle that is made of metals or the like. The injection needle 83 does not contract due to the contraction of the internal region that is punctured by the injection needle 83. The tube 10*b* is attached to the rear end of the injection needle 83. The injection needle 83 is communicated with the driving valve 9 through the tube 10*b*. The supporter 5 is attached to the injection needle 83 near the rear end of the injection needle 83. Similarly to the injection needle 3 according to the first embodiment described above, the driving unit 6 drives the injection needle 83 so that the injection needle 83 protrudes. The injection needle 83 is hollow similarly to the injection needle 3 according to the first embodiment described above.

The tissue-shape changing system 84 functions as a sealing unit that is an exemplary leak prevention unit. The tissue-shape changing system 84 changes the shape of the surface tissue (living tissue) around an internal region that is punctured by the injection needle 83. The tissue-shape changing system 84 includes a pair of high-friction rotation units 84*a* and 84*b*, a rotation propagation unit 84*c*, a driving unit 84*d*, and a rotation-direction changing unit 84*e*. The pair of the high-friction rotation units 84*a* and 84*b* extend the surface tissue (living tissue) of the internal region that is punctured by the injection needle 83. The rotation propagation unit 84*c* propagates the rotation of the high-friction rotation unit 84*a* to the high-friction rotation unit 84*b*. The driving unit 84*d* rotates the pair of the high-friction rotation units 84*a* and 84*b*. The rotation-direction changing unit 84*e* changes the rotation direction of drive force of the driving unit 84*d* into the rotation direction of the high-friction rotation unit 84*a*.

The high-friction rotation units 84*a* and 84*b* are made of high-frictional materials that causes high friction for moving the surface tissue of the internal region (e.g., living tissue in the inner surface of organs). The high-friction rotation units 84*a* and 84*b* have a structure of a roller and are attached to capsule casing 2 in a manner such that the rotation axis of the high-friction rotation unit 84*a* is arranged in parallel with that of the high-friction rotation unit 84*b*, such that the opening 2*c* from which the injection needle 83 protrudes is sandwiched by the high-friction rotation units 84*a* and 84*b*, and such that the high-friction rotation units 84*a* and 84*b* are rotatable. The pair of the high-friction rotation units 84*a* and 84*b* are exposed to the outer surface of the capsule casing 2. When the capsule medical apparatus 81 inside the subject reaches the internal region that is to be punctured (i.e., the internal region of interest that is to be punctured by the injection needle 83), the high-friction rotation units 84*a* and 84*b* touch the surface tissue of the internal region.

The rotation propagation unit 84*c* is a high-friction component that is continuous without an end. The rotation propagation unit 84*c* is attached to the high-friction rotation units 84*a* and 84*b* in a manner such that the rotation propagation unit 84*c* looks similar to the shape of "∞" as shown in FIG. 21. When the high-friction rotation unit 84*a* is rotated by the driving force of the driving unit 84*d*, the rotation propagation unit 84*c* that is attached as described above propagates the rotation of the high-friction rotation unit 84*a* to the high-friction rotation unit 84*b* so that the pair of the high-friction rotation units 84*a* and 84*b* rotate in the opposite different directions (in the directions drawn with a thin line in FIG. 21). The rotation propagation unit 84*c* is arranged outside a path in which the injection needle 83 moves, so that the rotation propagation unit 84*c* does not hinder the protrusion of the injection needle 83.

The rotation-direction changing unit 84*e* is realized by a gear box or the like that includes one or more gears. The rotation-direction changing unit 84*e* includes a rotation unit that propagates drive force of the driving unit 84*d* to the high-friction rotation unit 84*a*. The rotation-direction changing unit 84*e* is arranged inside the capsule casing 2 in a manner such that the rotation unit touches the high-friction rotation unit 84*a*. The rotation-direction changing unit 84*e* changes the rotation direction of the drive force of the driving unit 84*d* into the rotation direction of the high-friction rotation unit 84*a* (the counterclockwise direction in FIG. 21) and then propagates the drive force to the high-friction rotation unit 84*a*. Thus, the high-friction rotation unit 84*a* described above rotates using the drive force of the driving unit 84d that is propagated by the rotation-direction changing unit 84e.

The tissue-shape changing system 84 configured as above rotates the pair of the high-friction rotation units 84a and 84b in different directions as shown in FIG. 21, using the drive force of the driving unit 84d that is controlled by the control unit 89. The tissue-shape changing system 84 changes a shape of a surface (i.e., extends a surface) of an internal region that is touched by the high-friction rotation units 84a and 84b (i.e., an internal region where the injection needle 83 remains). Using the tissue-shape changing system 84, the opening size of the puncture hole in the internal region is minimized after the injection needle 83 is pulled out so that the puncture hole is sealed.

The control unit 89 controls the tissue-shape changing system 84 so that the extended surface tissue of the internal region where the injection needle 83 is maintained. The control unit 89 controls actuation of the driving unit 84d so as to control the instant and duration of the extension of the surface tissue of the internal region. Other than the function to control the tissue-changing system 84, the control unit 89 has the same functions as those of the control unit 13 of the capsule medical apparatus 1 according to the first embodiment.

Figure 22:
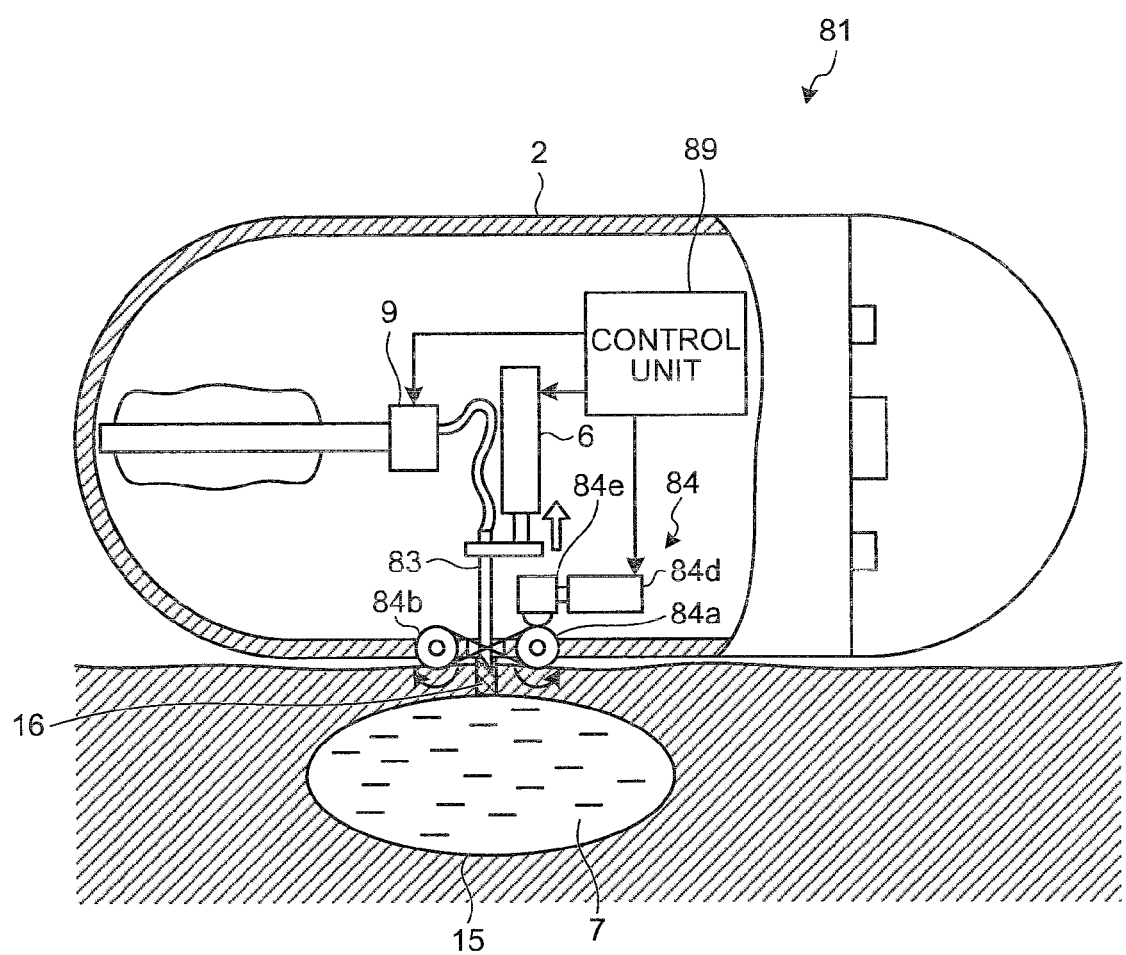
FIG. 22 is a schematic diagram in which a tissue-shape changing system extends surface tissue in an affected area puncture by the injection needle.
Figure 23A:
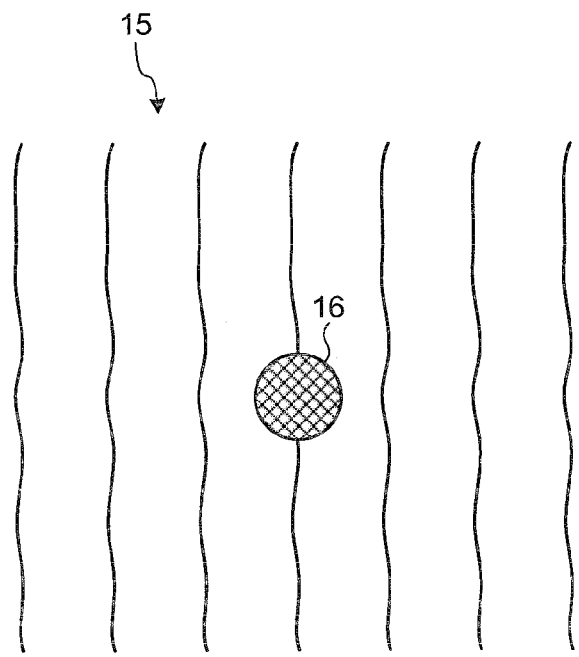
FIGS. 23A and 23B are schematic diagrams in which a puncture hole of an affected area contracts due to the extension of the surface tissue.
Figure 23B:
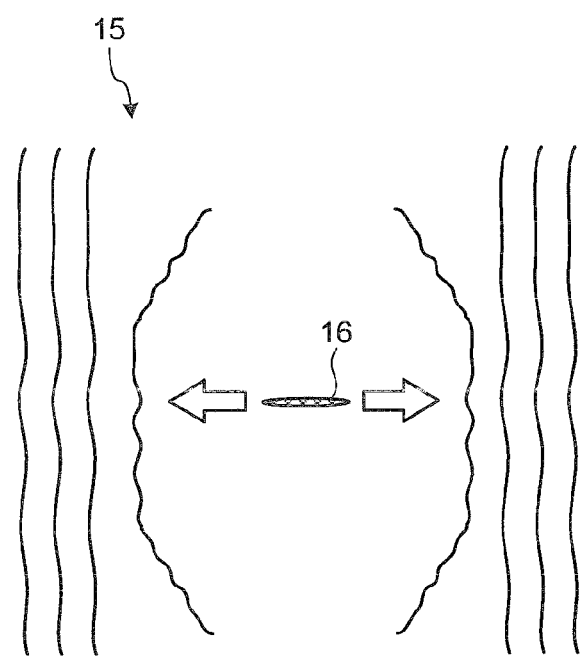

An operation of the capsule medical apparatus 81 according to the fifth embodiment of the present invention is described in detail below. As an example of the operation, the capsule medical apparatus 81 injects a drug solution to an affected area, which is an example of an internal region of interest, inside the subject. FIG. 22 is a schematic diagram in which the tissue-shape changing system extends the surface tissue of the internal region that is punctured by the injection needle. FIGS. 23A and 23B are schematic diagrams in which the puncture hole in the internal region is sealed due to the extension of the surface tissue. Described below with reference to FIGS. 22 and 23 is an operation of the capsule medical apparatus 81 for sealing the puncture hole 16 that is made by the injection needle 83 in the affected area 15. Other than the operation for sealing the puncture hole in the internal region, the capsule medical apparatus 81 according to the fifth embodiment is operated similarly to the capsule medical apparatus 1 according to the first embodiment described above.

After the capsule medical apparatus 81 completes injecting the drug solution 7 into the affected area 15 through the injection needle 83 that punctures the affected area 15, the control unit 89 controls the driving unit 6 so that the injection needle 83 remains in the injection needle 83. The control unit 89 controls the tissue-shape changing system 84 so that the extended surface tissue of the affected area 15 where the injection needle 83 is maintained. In detail, the control unit 89 actuates the driving unit 84d when the driving valve 9 closes itself. Under the control of the control unit 89, the driving unit 84d generates rotation force for the high-friction rotation units 84a and 84b. The high-friction rotation units 84a and 84b are rotated in different directions as shown in FIG. 22, using the drive force of the driving unit 84d that is propagated by the rotation-direction changing unit 84e. Thus, the surface tissue of the affected area 15 (specifically, the surface tissue near the puncture hole 16) is extended in a direction outward from the puncture hole 16 that is made by the injection needle 83 in the affected area 15.

Then, the control unit 89 controls the driving unit 84d so that the high-friction rotation units 84a and 84b keep the surface tissue of the affected area 15 extended. At the same time, the control unit 89 controls the driving unit 6 so that the injection needle 83 is pulled out from the affected area 15 and the injection needle 83 is then stored inside the capsule casing 2. Thus, the driving unit 6 pulls out the injection needle 83 from the puncture hole 16 in the affected area 15 that remains being extended and stores the injection needle 83 inside the capsule casing 2.

After the injection needle 83 is pulled out from the affected area 15, the surface tissue near the puncture hole 16 remains being extended by the high-friction rotation units 84a and 84b of the tissue-shape changing system 84 described above. The affected area 15 being extended contracts so that the opening size of the puncture hole 16 that is made due to the puncturing of the injection needle 83 becomes smaller than that of the puncture hole 16 being punctured shown in FIG. 23A. The opening size of the puncture hole 16 is eventually minimized so that the puncture hole 16 is sealed (as shown in FIG. 23B that illustrates the puncture hole 16 after the injection needle 83 is pulled out).

Even after the injection needle 83 is pulled out from the affected area 15 under the control of the driving unit 6, the control unit 89 controls the driving unit 84d so that for a predetermined time the extended surface tissue of the affected area 15 caused by the high-friction rotation units 84a and 84b is maintained. In a predetermined time after the injection needle 83 is stored inside the capsule casing 2, the control unit 89 controls the driving unit 84d so that maintaining the extension of the surface tissue of the affected area 15 is stopped.

Because the tissue-shape changing system 84 maintains the extension of the surface tissue of the affected area 15 for the predetermined time, the puncture hole (the site of the puncture) 16 in the affected area remains sealed after the tissue-shape changing system 84 stops maintaining the extension of the surface tissue. Therefore, the drug solution 7 does not leak from the puncture hole 16 and remains inside the affected area 15 even after the injection needle 83 is pulled out from the affected area 15. As a result, the drug solution 7 in the affected area 15 does not spread over internal regions other than the affected area 15 inside the subject.

When the capsule medical apparatus 81 completes injecting the drug solution 7 into the affected area 15 through the injection needle 83, the control unit 89 controls the driving unit 84d so that the rotation of the high-friction rotation units 84a and 84b extends the surface tissue of the affected area 15. Not limited to this, the tissue-shape changing system 84 may extend the surface tissue of the affected area 15 in a different period of time. For example, when the injection needle 83 punctures the affected area 15 (i.e., before injecting the drug solution 7 into the affected area 15), the control unit 89 may control the driving unit 84d as the driving unit 84d rotates the high-friction rotation units 84a and 84b so that the surface tissue of the affected area 15 is extended. Further, while the drug solution 7 is injected into the affected area 15 through the injection needle 83, the control unit 89 may control the driving unit 84d as the driving unit 84d rotates the high-friction rotation units 84a and 84b so that the surface tissue of the affected area 15 is extended.

As described above, in the fifth embodiment of the present invention, the capsule medical apparatus includes the tissue-shape changing system that extends the surface tissue of the internal region that is to be punctured. The tissue-shape changing system extends the surface tissue of the internal region that is punctured by the injection needle (i.e., extends the living tissue near the puncture hole). The tissue-shape changing system maintains the extension of the surface tissue of the internal region at least until the injection needle is pulled out from the internal region so that the puncture hole in the internal region is sealed. Other configurations are the same as those of the first embodiment. Thus, the capsule medical apparatus can provide the same operational effects as those of the first embodiment. Further, the capsule medical apparatus can seal the puncture hole can be sealed without involving the contraction of the injection needle. As a result, the capsule medical apparatus can adopt a relatively simple configuration and can inject the drug solution into more than one regions of interest inside the subject.

In the second variation of the fourth embodiment described above, the injection needle 53 is inserted into the cauterization unit 74, which is cylinder-shaped. The cauterization unit 74 protrudes together with the protrusion of the injection needle 53 from the capsule casing 2. Alternatively, the protrusion of the cauterization unit 74 may not be operated together with the protrusion of the injection needle 53 from the capsule casing 2. In this case, in the capsule medical apparatus 71 according to the second variation of the fourth embodiment, the cauterization unit 74 may be arranged inside the capsule casing 2 being independent of the injection needle 53 as shown in FIG. 24 so that the cauterization unit can protrude from the capsule casing 2 being independent of the injection needle 53. The cauterization unit 74 shown in FIG. 24 is driven by the driving unit 76 that is controlled by the control unit 79. The cauterization unit 74 shown in FIG. 24 can protrude from the capsule casing 2 through the opening 2c in the instant from that when the injection needle 53 protrudes. Similarly to the cauterization unit that is cylinder-shaped described above, the cauterization unit 74 shown in FIG. 24 cauterizes the living tissue around the puncture hole in the internal region that is punctured by the injection needle 53 so that the puncture hole is sealed. The cauterization unit 74 shown in FIG. 24 may be any shape, e.g., a cylinder shape (i.e., cylindrical column), a bar shape (i.e., polygonal column) as long as the cauterization unit 74 can protrude from the opening 2c in the capsule casing 2.

In the first embodiment described above, the heater 4 that heats the injection needle 3, which is made of thermoplastic materials, is shaped as a thin-film. The heater 4 is attached to and surrounds the outer surface of the injection needle 3. Not limited to this, the heater that heats the injection needle 3 may be arranged inside the wall surface of the injection needle 3 or be arranged on the inner wall surface of the injection needle 3. Not limited to the heating process of the heater 4 (i.e., heating process using an electrical heater), the injection needle 3, which is made of thermoplastic materials, may soften due to the contact with the drug solution that is heated. Alternatively, the injection needle 3 inside the capsule casing 2 may be cooled inside the capsule casing 2 using a peltiert device or the like so that the injection needle 3 that has puncture the internal region softens due to the body temperature of the subject.

In the second embodiment described above, in order to seal the puncture hole in the internal region, the thin-film tube 24 is crushed flatly by the contraction of the internal region. Not limited to this, the thin-film tube 24 may be made of elastic materials and contract due to its elasticity. The elastic thin-film tube 24, which is elastic, contracts due to the contraction of the internal region so as to seal the puncture hole in the internal region. When the thin-film tube 24 is pulled out from the puncture hole in the internal region, the shape of the thin-film tube 24 returns to a cylinder shape.

In the first, second, fourth, and fifth embodiments, and in the first and second variations of the fourth embodiment described above, the injection needle protrudes along the radial direction of the capsule casing 2 so that the injection needle punctures the internal region in a manner such that the injection needle is substantially vertical to the surface of the internal region. Not limited to this, the injection needle may protrude from the capsule casing 2 in a manner such that the longitudinal direction of the injection needle oblique to the radial direction of the capsule casing 2 as shown in the third embodiment and the first variation of the third embodiment. Thus, the injection needle punctures the internal region in a manner such that the injection needle makes an acute angle with the surface of the internal region. In this case, similarly to the third embodiment and the first variation of the third embodiment, the length of the puncture hole that is made in the internal region by the injection needle is longer than that of the puncture hole that is made by the injection needle that punctures the internal region vertically. As a result, the drug solution is further unlikely to leak out from the puncture hole.

In the third embodiment described above, the injection needle protrudes from the capsule casing 2 in a manner such that the longitudinal direction of the injection needle is oblique to the radial direction of the capsule casing 2. Thus, the injection needle punctures the internal region in a manner such that the injection needle makes an acute angle with the surface of the internal region. Not limited to this, as described in the first, second, fourth, and fifth embodiment, and in the first and second variations of the fourth embodiment, the injection needle may protrude in the radial direction of the capsule casing 2 so that the injection needle that is substantially vertical to the surface of the internal region punctures the internal region.

In the fourth embodiment and the second variation of the fourth embodiment described above, the injection needle is pulled out after the cauterization unit cauterizes the living tissue around the puncture hole. Not limited to this, the injection needle that has punctured the internal region may be gradually pulled out while the cauterization unit cauterizes the living tissue around the puncture hole in the internal region. Thus, in the fourth embodiment and the second variation of the fourth embodiment, the cauterization process of the living tissue by the cauterization unit and the pullout of the injection needle from the internal region are performed at the same time so that the injection needle is gradually pulled out from the puncture hole while the cauterization unit cauterizes the living tissue around the puncture hole.

In the first variation of the fourth embodiment described above, the injection needle 63 that has the cauterization function is pulled out from the internal region after cauterizing the living tissue around the puncture hole. Not limited to this, the injection needle 63 may be gradually pulled out from the internal region while the injection needle 63 cauterizes the living tissue around the internal region. In this case, the injection needle 63 completes cauterizing the living tissue around the puncture hole by the time when the injection needle 63 is completely pulled out from the internal region.

In the fifth embodiment described above, the tissue-shape changing system 84 extends the surface tissue of the internal region that is punctured by the injection needle 83. Not limited to this, the tissue-shape changing system 84 may extend the internal region that is not yet punctured by the injection needle 83. In this case, the capsule medical apparatus 81 described above punctures the internal region with the injection needle 83 when the surface tissue of the internal region is extended by the tissue-shape changing system 84. After the injection needle 83 is pulled out from the internal region, the tissue-shape changing system 84 ends the extension process. The puncture hole that is made by the injection needle 83 contracts due to the contraction of the internal region that has been extended.

In the fifth embodiment described above, the tissue-shape changing system 84 extends the surface tissue of the internal region that is punctured by the injection needle 83. Not limited to this, the tissue-shape changing system 84 may extend the surface tissue of the internal region, which is punctured by the injection needle 83, toward the puncture hole so that the surface tissue contracts. In this case, the driving unit 84d of the tissue-shape changing system 84 is rotated in the reverse direction so as to rotate the high-friction rotation units in the reverse directions thereof. The puncture hole that is made by the injection needle 83 is thus sealed because the shape of the tissue is changed by the tissue-shape changing system 84. The tissue-shape changing system 84 may make the surface tissue of the internal region contract while the injection needle 83 is pulled out from the internal region or after the injection needle 83 is completely pulled out from the internal region.

In the first, second, third, fourth, and fifth embodiments, and in the variations thereof described above, the capsule medical apparatus injects the drug solution that affects the internal region of the subject. Not limited to this, the capsule medical apparatus may inject any liquid into the internal region of the subject. The liquid that is injected by the capsule medical apparatus into the internal region may be a transparent liquid or a colored liquid (e.g., a liquid used for marking).

In the first, second, third, fourth, and fifth embodiments, and in the variations thereof described above, single driving unit that is actuated using power protrudes the injection needle from the capsule casing, punctures the internal region of the subject with the injection needle, and pulls out the injection needle that punctures the internal region from the internal region. Not limited to this, two driving units may be used: one driving unit that protrudes the injection needle from the capsule casing; and another driving unit that punctures the internal region with the injection needle and pulls out the injection needle from the internal region. In this case, the driving unit that protrudes the injection needle from the capsule container may be an electric actuator or the like that is actuated using power similarly to the driving unit 6 described above or may be a magnetic actuator that is actuated by external magnetic field that is applied from the outside. The driving unit that punctures the injection needle with the injection needle and pulls out the injection needle from the internal region may be an electric actuator or the like that is actuated using power or may be a magnet that is actuated by external magnetic field.

Figure 25:
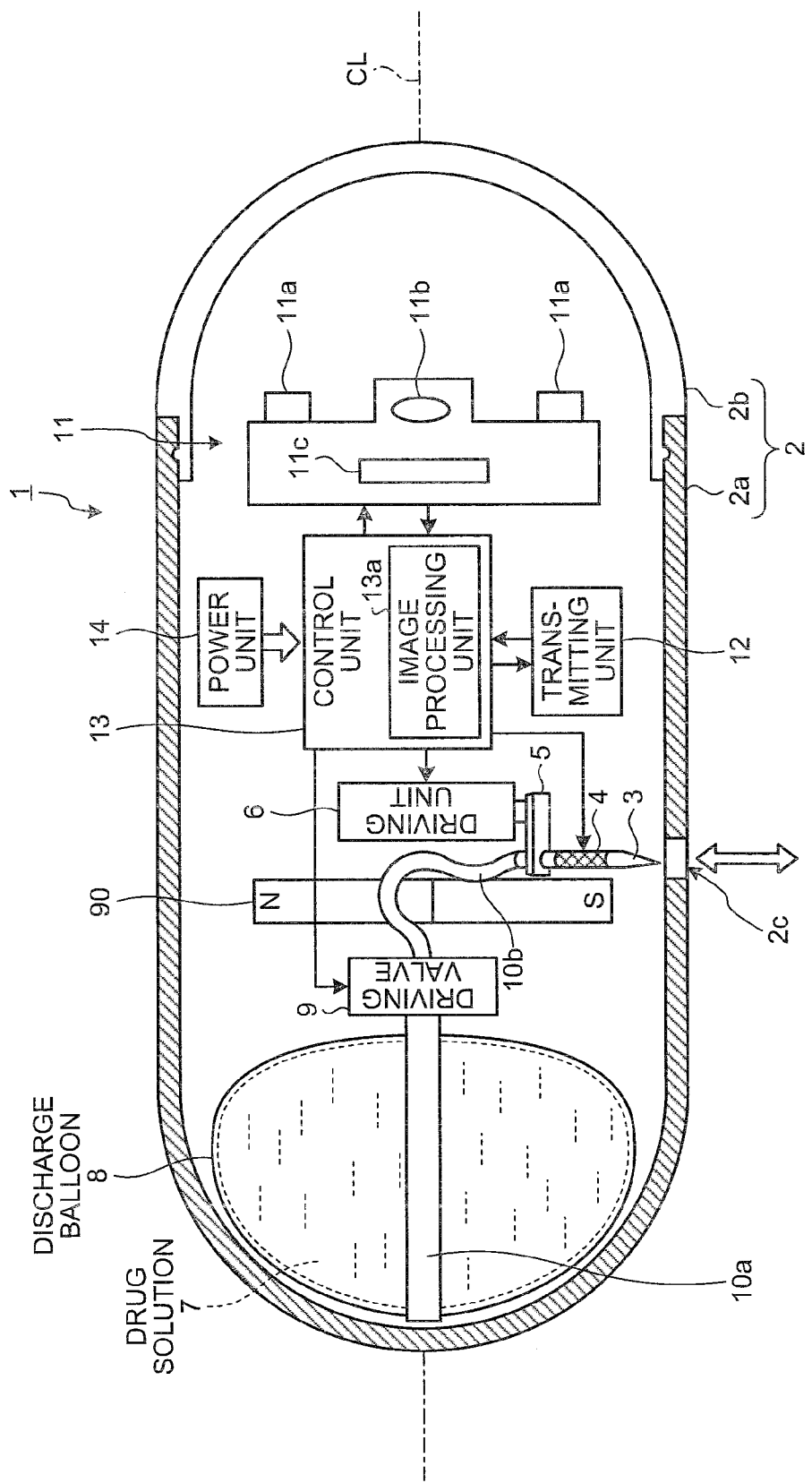
FIG. 25 is a schematic diagram of an exemplary configuration of a capsule medical apparatus that includes a driving unit that drives the protrusion of the injection needle and another driving unit that drives puncture and pullout of the injection needle.

Thus, the capsule medical apparatus 1 according to the first embodiment described above may include a driving unit 6 that drives the protrusion of the injection needle 3, and a driving unit, which is not the driving unit 6, that performs the puncturing and the pullout of the injection needle 3. FIG. 25 is a schematic diagram of an exemplary configuration of a capsule medical apparatus that includes a driving unit that drives the protrusion of the injection needle and another driving unit that drives puncture and pullout of the injection needle.

In the capsule medical apparatus 1 shown in FIG. 25, the injection needle 3 is supported by the supporter 5 in a manner such that the injection needle 3 is tilted in the driving direction of the driving unit 6 (i.e., the direction drawn with a thick line in FIG. 25, to which the injection needle 3 protrudes). The driving unit 6 is actuated by the control unit 13 and protrudes the injection needle 3. A magnet 90 is arranged inside the capsule casing 2 in a manner such that a direction to which the magnet 90 is magnetized is consistent with the radial direction of the capsule casing 2. The magnet 90 rotates the capsule casing 2 due to the external magnetic filed that is applied by an external apparatus that is located outside the subject so that the injection needle 3 that has been protruded punctures the internal region. The magnet 90 then pulls out the injection needle 3 from the internal region.

Figure 26:
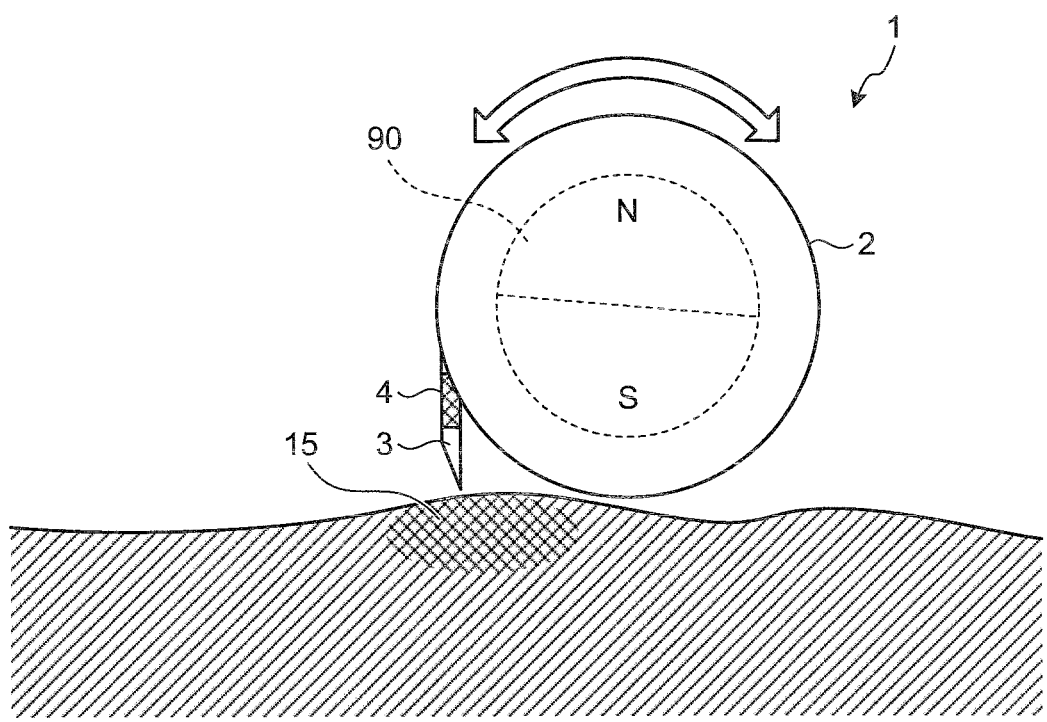
FIG. 26 is a schematic diagram in which the injection needle punctures an internal region due to an external magnetic field.

In more detail, as shown in FIG. 26, the magnet 90 rotates the capsule casing 2 in a circular direction due to the external magnetic field so as to rotate the injection needle 3 that has been protruded from the capsule casing 2, and the injection needle 3 then moves toward the internal region (e.g., the affected area 15). The injection needle 3, with the heater 4, thus punctures the affected area 15. When the injection needle 3 is pulled out as described in the first embodiment above, the magnet 90 rotates the capsule casing 2 in a circular direction (a reverse direction to the circular direction for puncturing the affected area 15). The magnet 90 rotates the injection needle 3 that has contracted so that the injection needle 3, with the heater 4, moves away from the affected area 15. Thus, the injection needle 3 that has contracted is pulled out, with the heater 4, from the affected area 15. The driving unit 6 then stores the injection needle 3 that has contracted and heater 4 inside the capsule casing 2. Further, after the injection needle 3 punctures the affected area 15 due to the external magnetic field, static magnetic field may be applied so that the capsule medical apparatus 1 stops rotating. When the drug solution 7 is injected into the affected area 15 and the injection needle 3 contracts due to the heating process of the heater 4 as described above, the injection needle 3 is further unlikely to be pulled out through rebound of the internal region near the affected area 15, and the drug solution 7 can be injected more accurately.

The capsule medical apparatus 1 shown in FIG. 25 protrudes the injection needle 3 from the capsule casing 2, punctures the internal region with the injection needle 3, and pulls out the injection needle 3 that punctures the internal region from the internal region similarly to the capsule medical apparatus 1 of the first embodiment. The capsule medical apparatus 1 shown in FIG. 25 provides the same operational effects as those of the first embodiment. In FIG. 25, the capsule medical apparatus 1 includes the driving unit that performs the protrusion of the injection needle and the driving unit that performs the puncturing and the pullout of the injection needle. Not limited to this, such a configuration may be applied to other capsule medical apparatus according to the second, third, fourth, and fifth embodiments and the variations thereof. In this case, the capsule medical apparatus provides the same operational effects as those of the capsule medical apparatus according to the second, third, fourth, and fifth embodiments and the variations thereof.

Figure 27:
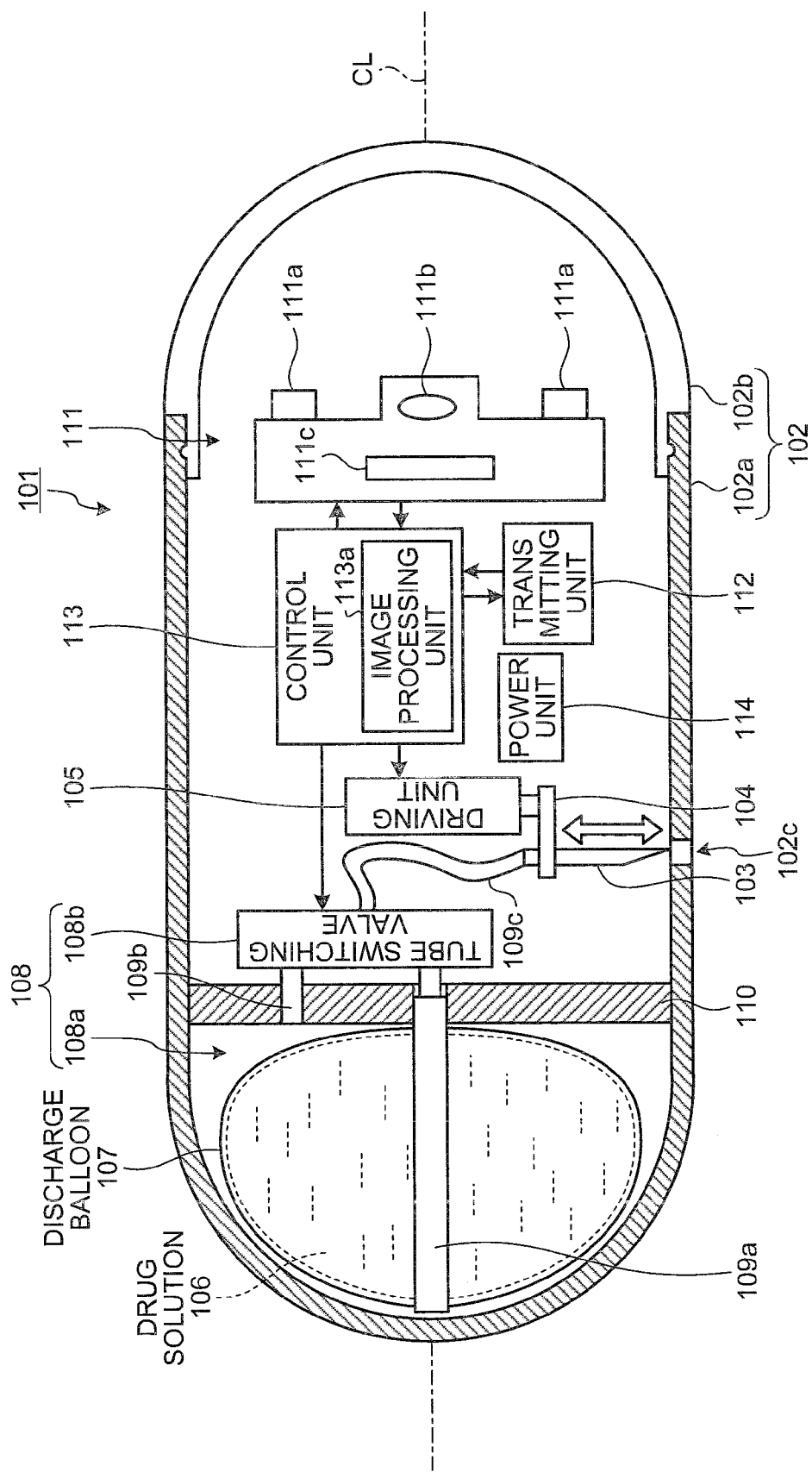
FIG. 27 is a schematic diagram of an exemplary configuration of a capsule medical apparatus according to a sixth embodiment of the present invention.

FIG. 27 is a schematic diagram of an exemplary configuration of a capsule medical apparatus according to a sixth embodiment of the present invention. As shown in FIG. 27, a capsule medical apparatus 101 according to the sixth embodiment includes a capsule casing 102, an injection needle 103, a supporter 104, and a driving unit 105. The capsule casing 102 consists of a cylinder-shaped container 102a and a dome-shaped container 102b. The injection needle 103 punctures an internal region of a subject. The supporter 104 supports the injection needle 103. The driving unit 105 protrudes the injection needle 103 from the capsule casing 102. The capsule medical apparatus 101 further includes a discharge balloon 107 that injects a drug solution 106 into an internal region through the injection needle 103, a pressure suppressing unit 108 that is an exemplary leak prevention unit and suppresses an increase in pressure of the drug solution 106 that is injected into the internal region, communicating tubes 109a and 109b, and a tube 109c. The capsule medical apparatus 101 further includes an imaging unit 111 that captures in-vivo images of the subject, a transmitting unit 112 that transmits and receives wireless signals to and from a transmitting apparatus (not shown) that is located outside a subject, a control unit 113 that controls each of the components of the capsule medical apparatus 101, and a power unit 114, which can be a battery or the like.

The capsule casing 102 is shaped like a capsule and is of a size that can be introduced into a subject, e.g., a patient. The capsule casing 102 is made by sealing the open end of the cylinder-shaped container 102a, which is dome-shaped at its other end, with the dome-shaped container 102b. The dome-shaped container 102b is an optical member and is transparent to light of a predetermined waveband (e.g., visible light). In contrast, the cylinder-shaped container 102a is substantially opaque to visible light. There is an opening 102c on the cylinder-shaped container 102a, from which the injection needle 103 protrudes. The capsule casing 102 contains each of the components (the injection needle 103, the driving unit 105, the discharge balloon 107, the pressure suppressing unit 108, the communicating tubes 109a and 109b, the imaging unit 111, the transmitting unit 112, the control unit 113, the power unit 114, and the like). The capsule casing 102 has a predetermined watertight structure (not shown) and maintains a watertight state of electric components, e.g., the driving unit 105, the imaging unit 111, the transmitting unit 112, the control unit 113, and the power unit 114.

The injection needle 103 is a hollow needle that has a pointed end (front end) and is made of a thermoplastic resin. The tube 109c is attached to the other end (rear end) of the injection needle 103. The supporter 104 is fixed near the rear end of the injection needle 103. The supporter 104 supports the injection needle 103 in a manner such that the injection needle 103 can protrude from the opening 102c in the capsule casing 102. The supporter 104 is connected with the driving unit 105.

The driving unit 105 functions as a protrusion driving unit. The driving unit 105 protrudes the injection needle 103 toward an internal region of a subject, punctures the internal region with the injection needle 103, and pulls out the injection needle 103 that punctures the internal region from the internal region. The driving unit 105 can be a linear actuator or the like. The driving unit 105 is connected with the supporter 104 of the injection needle 103. The driving unit 105 reciprocates the injection needle 103 linearly in a predetermined direction (i.e., the direction in the arrow drawn with a thick line in FIG. 27) using the supporter 104. The driving unit 105 protrudes the injection needle 103 through the opening 2c to the outside of the capsule casing 102 and punctures the internal region of the subject with the injection needle 103. Under the operational timing of the control unit 113, the driving unit 105 pulls out the injection needle 103 from the internal region and stores the injection needle 103 inside the capsule casing 102.

The discharge balloon 107 functions as a liquid injection unit that injects a liquid into an internal region using the injection needle 103 that punctures the internal region of the subject. The discharge balloon 107 can be made of an extendable elastic film. The discharge balloon 107 is attached to the communicating tube 109a. The discharge balloon 107, when it is expanded, contains and stores the drug solution 106 therein. The inside of the discharge balloon 107 is communicated with the communicating tube 109a and, depending on a state of the pressure suppressing unit 108 described later, is communicated with the injection needle 103 through the communicating tube 109a, the tube 109c, and the like. When the discharge balloon 107 is communicated with the injection needle 103, the discharge balloon 107 discharges the drug solution 106 to the injection needle 103 due to a contraction of the discharge balloon 107. The drug solution 106 is then injected into the internal region using the injection needle 103. When the communicated state between the discharge balloon 107 and the injection needle 103 is blocked due to the switching of the pressure suppressing unit 108 or the discharge balloon 107 cannot contract any more, the discharge balloon 107 stops discharging the drug solution 106.e., injection stops).

The pressure suppressing unit 108 suppresses, using the injection needle 103, an increase in pressure of the liquid that is injected into the internal region of the subject. The pressure suppressing unit 108 includes a suction unit 108a, and a tube-path switching valve 108b. The pressure suppressing unit 108 suppresses, using the injection needle 103 that punctures the internal region, an increase in the drug solution 106 that is injected into the internal region through the injection needle 103 that punctures the internal region.

The suction unit 108a sucks in, through the injection needle 103, a liquid (backflow liquid) that is a part of the liquid injected into the internal region of a subject and flows backward from the internal region. As shown in FIG. 27 is made by a part of a rear end (which is dome-shaped) of the cylinder-shaped container 102a and a wall part 110 inside the cylinder-shaped container 102a. The wall part 110 divides the internal space of the capsule casing 102. The wall part 110 separates space containing electric components from space containing the discharge balloon 107, and thus the discharge balloon 107 is sealed inside the rear end of cylinder-shaped container 102a. As described above, the suction unit 108a seals and contains the discharge balloon 107 and the communicating tube 109a. Depending on the switching of the tube-path switching valve 108b, the suction unit 108a is communicated with the tube-path switching valve 108b by the communicating tube 109b. The suction unit 108a is communicated with the injection needle 103 through the communicating tube 109b, the tube 109c, and the like. When the suction unit 108a is communicated with the injection needle 103, the suction unit 108a sucks in the drug solution 106 in the internal region through the injection needle 103, due to the negative pressure that is generated by the contraction of the discharge balloon 107 (i.e., by the discharge operation that discharges the drug solution 106). As a result, the suction unit 108a sucks in the backflow liquid (that is a part of the drug solution 106) that flows back toward the injection needle 103 due to the pressure in the internal region. The suction unit 108a contains the part of the drug solution 106 therein and prevents the drug solution 106 from leaking therefrom. When the suction unit 108a is not communicated with the injection needle 103 because of the switching of the tube-path switching valve 108b, the suction unit 108a stops sucking in the drug solution 106 in the internal region.

The tube-path switching valve 108b functions as a communicated state switching unit. The tube-path switching valve 108b switches the state of the injection needle 103 from the communicated state between the injection needle 103 and the discharge balloon 107 to the communicated state between the injection needle 103 and the suction unit 108a and vice versa. As shown in FIG. 27, the tube-path switching valve 108b is communicated with the discharge balloon 107 by the communicating tube 109a, communicated with the suction unit 108a by the communicating tube 109b, and communicated with the injection needle 103 by the tube 109c. Under the control of the control unit 113, the tube-path switching valve 108b switches the state of the injection needle 103 from the communicated state between the injection needle 103 and the discharge balloon 107 to the communicated state between the injection needle 103 and the suction unit 108a and vice versa. The tube-path switching valve 108b can block both the communicated state between the injection needle 103 and the discharge balloon 107 and the communicated state between the injection needle 103 and the suction unit 108a. Thus, the tube-path switching valve 108b may switch to one of the states: the communicated state between the injection needle 103 and the discharge balloon 107; the communicated state between the injection needle 103 and the suction unit 108a; and a blocked state in which both of the communicated states are blocked.

The tube 109c connects the tube-path switching valve 108b with the injection needle 103 so that the tube-path switching valve 108b and the injection needle 103 are communicated. The tube 109c may be a flexible tube or a tube that is made of extendable elastic materials. The tube 109c may be of any length that does not hinder the protrusion of the injection needle 103.

The imaging unit 111 captures in-vivo images of a subject. The imaging unit 111 includes an illumination unit 111a (e.g., an LED), an optical system 111b (e.g., a collective lens), a solid-state imaging device 111c (e.g., CCD and CMOS imaging sensors and the like). The imaging unit 111 is fixed in the capsule casing 102 in a manner such that the optical axis of the optical system 111b is consistent with an axis along a predetermined relative direction of the capsule casing 102 (e.g., a central axis CL along the longitudinal direction of the capsule casing 102) and such that the imaging view of the imaging unit 111 is directed in a predetermined direction (e.g., the longitudinal direction of the capsule casing 2). One or more illumination units 111a of the imaging unit 111 (it is preferable that the number be more than one) illuminate the inside of the organ of the subject. The internal organs of the subject are the photographic subject of the imaging unit 111. The optical system 111b collects reflective light from the photographic subject and forms an optical image of the photographic subject on the light-receiving surface of the solid-state imaging device 111c. The solid-state imaging device 111c captures an optical image of the photographic subject, i.e., an in-vivo image of the subject, which has been formed by the optical system 111b. The solid-state imaging device 111c generates a signal by performing a photoelectric conversion process. The imaging unit 111 transmits the signal to the control unit 113.

The transmitting unit 112 transmits and receives wireless signals to and from an external apparatus (not shown), e.g., an image displaying apparatus. The transmitting unit 112 includes a wireless antenna (not shown) and transmits and receives wireless signals via the wireless antenna. Under the control of the control unit 113, the transmitting unit 112 wirelessly transmits the in-vivo image of the subject captured by the imaging unit 111 described above to the external apparatus outside the subject. The transmitting unit 112 performs a modulation process or the like on the image signals (including data of in-vivo images) obtained from the control unit 113 in order to generate wireless signals that include the image signals. The transmitting unit 112 transmits the generated wireless signals to the external apparatus that is located outside the subject via the wireless antenna. Under the control of the control unit 113, the transmitting unit 112 receives the wireless signals transmitted from the receiving apparatus that is located outside the subject and then performs a demodulation process or the like on the received wireless signals to extract control signals from the wireless signals. The transmitting unit 112 transmits the control signal obtained from the external apparatus to the control unit 113.

The control unit 113 controls each of the components in the capsule medical apparatus 101 (e.g., the driving unit 105, the tube-path switching valve 108b, the imaging unit 111, and the transmitting unit 112) and controls input and output of signals among the components. Further, the control unit 113 controls the tube-path switching valve 108b, which in turn controls the discharge operation (injection operation) of the discharge balloon 107 and the suction operation of the suction unit 108a described above. According to the control signal that is transmitted from the external apparatus and obtained by the transmitting unit 112, the control unit 113 controls the driving unit 105 and the tube-path switching valve 108b. In doing so, a series of operations are completed that is performed during a period of time between the puncturing of an internal region with the injection needle 103 and the injecting the drug solution 106 into the internal region. The series of operations include the protruding process that protrudes the injection needle 103 using the driving unit 105, the discharge (injection) operation that discharges the drug solution 106 using the discharge balloon 107, the suction operation by the suction unit 108a, and the tube-path switching operation performed by the tube-path switching valve 108b.

The control unit 113 further includes an image processing unit 113a. The control unit 113 controls the operational timing of the imaging unit 111, and thus the solid-state imaging device 111c captures an image of a photographic subject (i.e., an in-vivo image of the subject), which is illuminated by the illumination unit 111a. The image processing unit 113a obtains the signal, on which the photoelectric conversion is performed by the solid-state imaging device 111c, and performs predetermined signal processes on the obtained signal to generate the image signal, which includes the data of the in-vivo image of the subject. Under the control of the control unit 113, the transmitting unit 112 wirelessly transmits the image signal to the external apparatus that is located outside the subject. Each time the image processing unit 113a generates an image signal (i.e., each time the imaging unit 111 captures an in-vivo image of the subject), the control unit 113 repeats the control process on the transmitting unit 112. The control unit 113 also controls the transmitting unit 112 when the transmitting unit 12 obtains the control signal from the external apparatus that is located outside the subject.

The power unit 114 can be a switch, a button-shaped battery, and the like. When the power unit 114 is switched to an ON state by the switch, the power unit 114 supplies power for the driving unit 105, the tube-path switching valve 108b, the imaging unit 111, the transmitting unit 112, and the control unit 113, which have been described above, as needed. When the power unit 114 is switched to an OFF state by the switch, the power unit 114 stops supplying power for each of the components, e.g., the control unit 113. The switch of the power unit 114 can be a magnetic switch that switches the state of the power unit 114 from the ON state to the OFF state and vice versa according to a magnetic field that is applied from the outside, or an optical switch that switches the state of the power unit 114 from the ON state to the OFF state and vice versa according to a predetermined optical signal, e.g., infrared light.

The capsule medical apparatus 101 configured as above is swallowed and introduced into the organs of a subject. The capsule medical apparatus 1 moves through the organs (i.e., inside the digestive tracts) of the subject due to the peristalsis or the like. The capsule medical apparatus 101 captures in-vivo images of the subject in sequence using the imaging unit 111 at predetermined intervals (e.g., 0.5-second intervals). The capsule medical apparatus 101 wirelessly transmits image signals of the in-vivo images in sequence to the external apparatus that is located outside the subject using the transmitting unit 112.

As described, the capsule medical apparatus 101 inside the subject continuously captures the in-vivo images of the subject in sequence and wirelessly transmits these in-vivo images while moving through the organs of the subject. The capsule medical apparatus 101 eventually reaches an internal region of interest, into which the drug solution 106 is to be injected. The capsule medical apparatus 101 that has reached the internal region punctures the internal region of interest with the injection needle 103 and injects the drug solution 106 through the injection needle 103. The capsule medical apparatus 101 suppresses the increase in pressure of the drug solution 106 inside the internal region and then pulls out the injection needle 103 from the internal region. After storing the injection needle 103 into the capsule casing 102, the capsule medical apparatus 101 moves through the organs of the subject until excreted by the subject.

Figure 28:
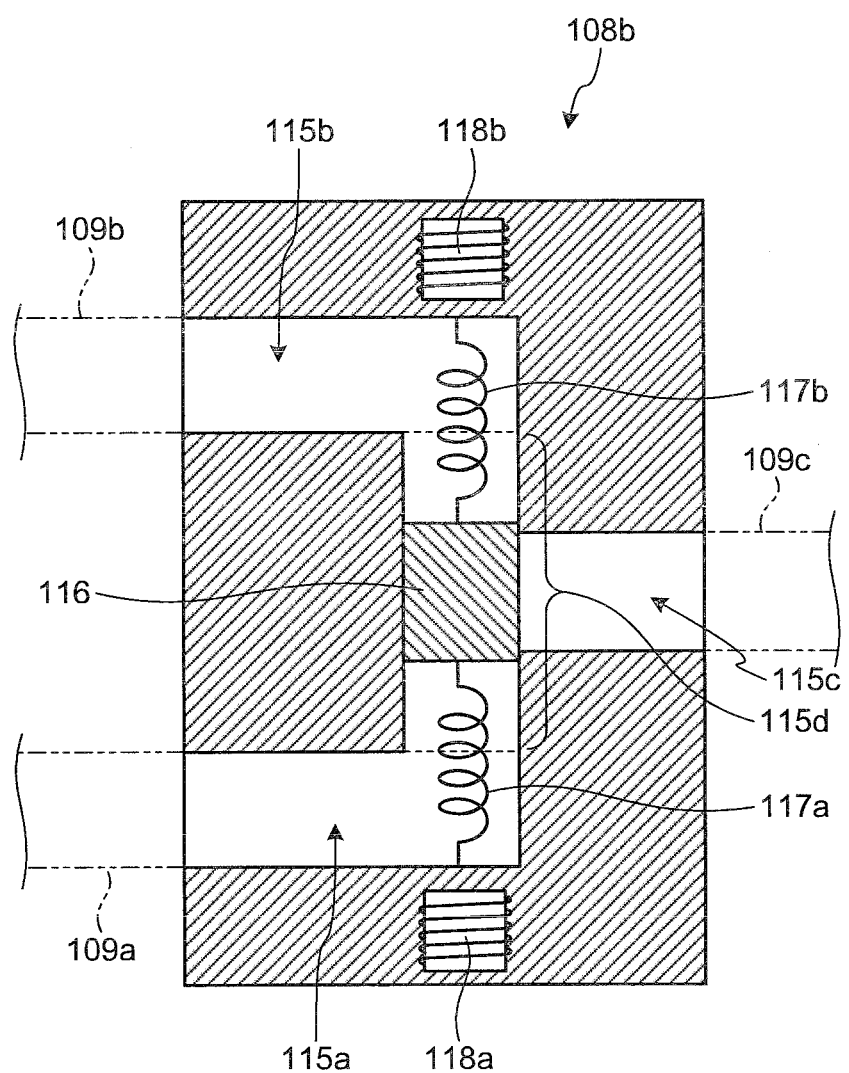
FIG. 28 is a cross-sectional schematic diagram of an exemplary configuration of a tube-path switching valve.
Figure 29:
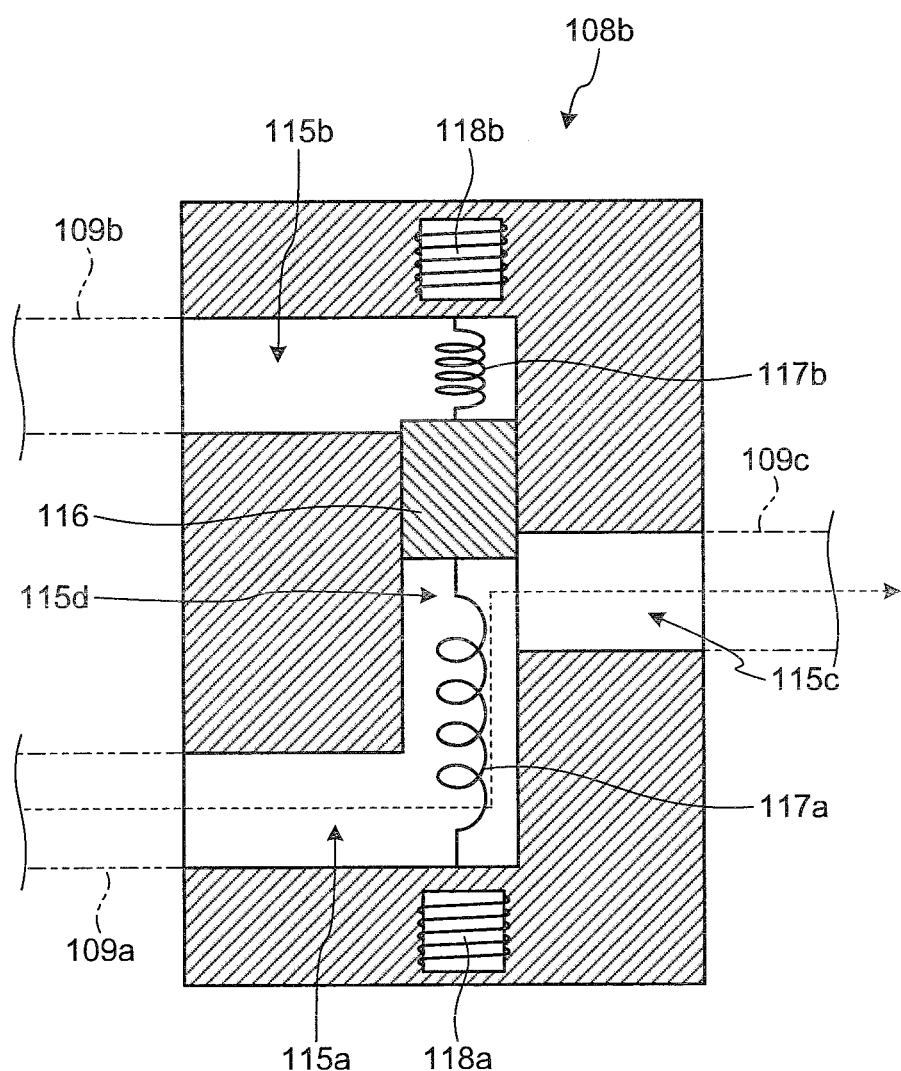
FIG. 29 is a schematic diagram in which the injection needle is communicated with a discharge balloon by the tube-path switching valve.
Figure 30:
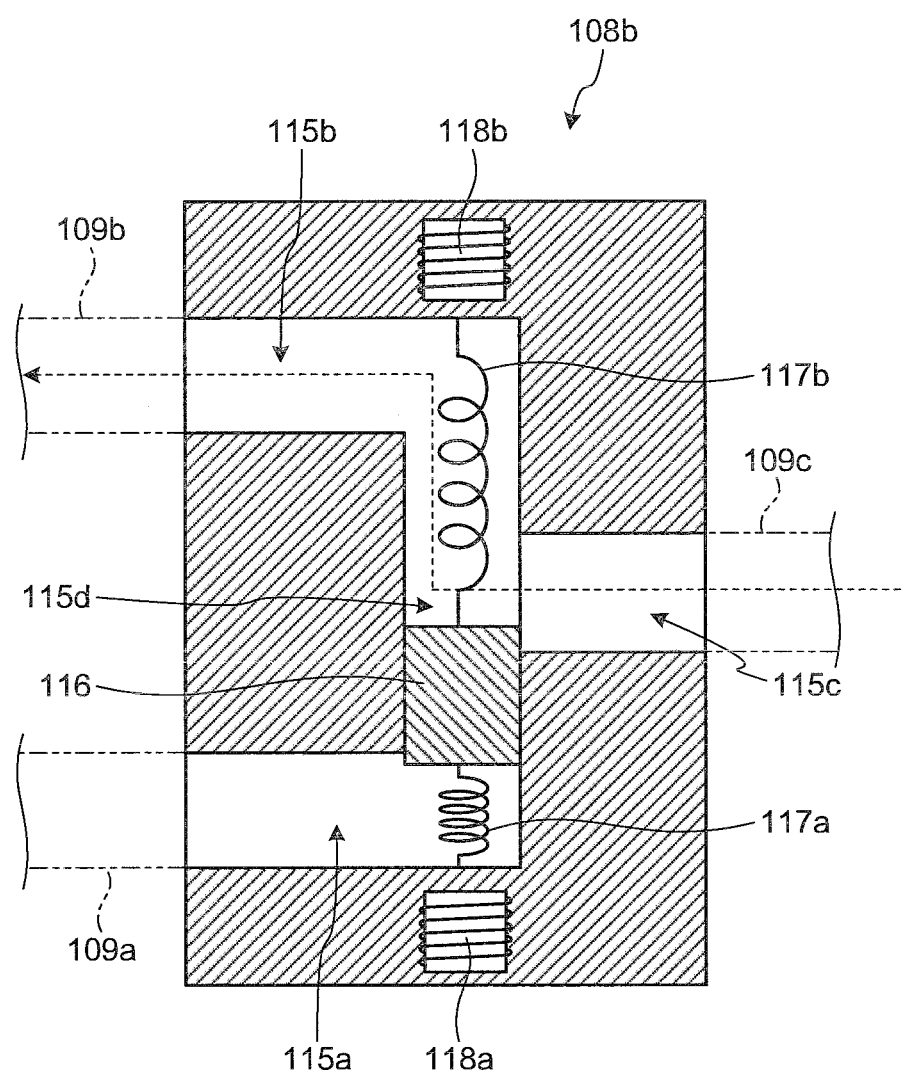
FIG. 30 is a schematic diagram in which the injection needle is communicated with a suction unit by the tube-path switching valve.

The tube-path switching valve 108b of the pressure suppressing unit 108 is described below in detail. FIG. 28 is a cross-sectional schematic diagram of an exemplary configuration of the tube-path switching valve. FIG. 29 is a schematic diagram in which the injection needle is communicated with the discharge balloon by the tube-path switching valve. FIG. 30 is a schematic diagram in which the injection needle is communicated with the suction unit by the tube-path switching valve. FIG. 28 illustrates the tube-path switching valve 108b that is in the blocked state described above.

As shown in FIG. 28, there are tube paths 115a to 115d in the tube-path switching valve 108b. The tube-path switching valve 108b includes a blocking component 116, springs 117a and 117b, and solenoids 118a and 118b that apply a magnetic field to the blocking component 116.

In the tube-path switching valve 108b, the communicating tube 109a is attached to the opening of the tube path 115a, the communicating tube 109b is attached to the opening of the tube path 115b, and the tube 109c is attached to the opening of the tube path 115c. In the tube-path switching valve 108b, the tube path 115a is communicated with the discharge balloon 107 through the communicating tube 109a, the tube path 115b is communicated with the suction unit 108a through the communicating tube 109b, and the tube path 115c is communicated with the injection needle 103 through the tube 109c. As shown in FIG. 28, the tube paths 115a to 115c are linked at the tube path 115d.

The blocking component 116 opens and closes the communication among the tube paths 115a to 115d. Entire or a part of the blocking component 116 is a magnetic body. The blocking component 116 has a shape that is suitable for the tube path 115d (a whole circumference of the outer surface of the blocking component touches the inner surface of the tube path 115d). The blocking component 116 slides within the tube path 115d to open or close the communication among the tube paths 115a to 115d. The springs 117a and 117b are attached to both ends of the blocking component 116, respectively.

The springs 117a and 117b control a position of the blocking component 116 within the tube path 115d. One end of the spring 117a is connected to the blocking component 116 and the other end thereof is connected to the inner surface of the tube path 115a. The springs 117a and 117b can be extended by the movement (sliding) of the blocking component 116 within the tube path 115d. The blocking component 116 can be positioned to block the opening of the tube path 115c using the springs 117a and 117b (see FIG. 28).

The solenoids 118a and 118b generate a magnetic field that causes the blocking component 116 to slide within the tube path 115d. As shown in FIG. 28, the solenoid 118a is arranged near the tube path 115a while the solenoid 118b is arranged near the tube path 115b. Under the control of the control unit 113, the solenoids 118a and 118b apply the magnetic field to the blocking component 116 so as to move the blocking component 116 to the tube path 115a or to the tube path 115b.

Depending on the position of the blocking component 116 within the tube path 115d, the tube-path switching valve 108b switches to one of the states: the blocked state described above; the communicated state between the injection needle 103 and the discharge balloon 107; and the communicated state between the injection needle 103 and the suction unit 108a. When the control unit 113 does not supply power to the solenoids 118a and 118b, the blocking component 116 is positioned at the opening of the tube path 115c according to elastic force of the springs 117a and 117b (see FIG. 28) so that the opening of the tube path 115c is blocked. When the control unit 113 does not supply power to the solenoids 118a and 118b, the solenoids 118a and 118b do not generate any magnetic field. The blocking component 116 blocks a communication path between the tube path 115a and the tube path 115c and also blocks a communication path between the tube path 115b and the tube path 115c. Thus, the tube-path switching valve 108b blocks the communication between the injection needle 103 and the discharge balloon 107 and the communication between the injection needle 103 and the suction unit 108a.

When the control unit 113 supplies power only to the solenoid 118b, the solenoid 118a does not generate the magnetic field while the solenoid 118b generates the magnetic field that is applied to the blocking component 116. The blocking component 116 then extends the springs 117a and 117b as shown in FIG. 29 and moves to the tube path 115b due to magnetic attracting force generated by the solenoid 118b so that the opening of the tube path 115c becomes open only to the tube path 115a. As a result, the blocking component 116 opens the communicating path between the tube path 115a and the tube path 115c (see the arrow drawn with a dot line in FIG. 29) while blocking the communicating path between the tube path 115b and the tube path 115c. Thus, the tube-path switching valve 108b opens the communication between the injection needle 103 and the discharge balloon 107 while blocking the communication between the injection needle 103 and the suction unit 108a. The discharge balloon 107 then injects the drug solution 106 into the internal region through the injection needle 103.

When the control unit 113 supplies power only to the solenoid 118a, the solenoid 118b does not generate a magnetic field while the solenoid 118a applies a magnetic field to the blocking component 116. In this case, as shown in FIG. 30, the blocking component 116 moves to the tube path 115a due to magnetic attracting force generated by the solenoid 118a, causing the spring 117b to extend and the spring 117a to contract so that the opening of the tube path 115c becomes open only to the tube path 115b. As a result, the blocking component 116 opens the communicating path between the tube path 115b and the tube path 115c (see the arrow drawn with a dot line in FIG. 30) while blocking the communicating path between the tube path 115a and the tube path 115c. Thus, the tube-path switching valve 108b opens the communication between the injection needle 103 and the suction unit 108a while blocking the communication between the injection needle 103 and the discharge balloon 107. The suction unit 108a then sucks in a part of the drug solution 106 from the inside of the internal region through the injection needle 103 as described above.

Figure 31A:
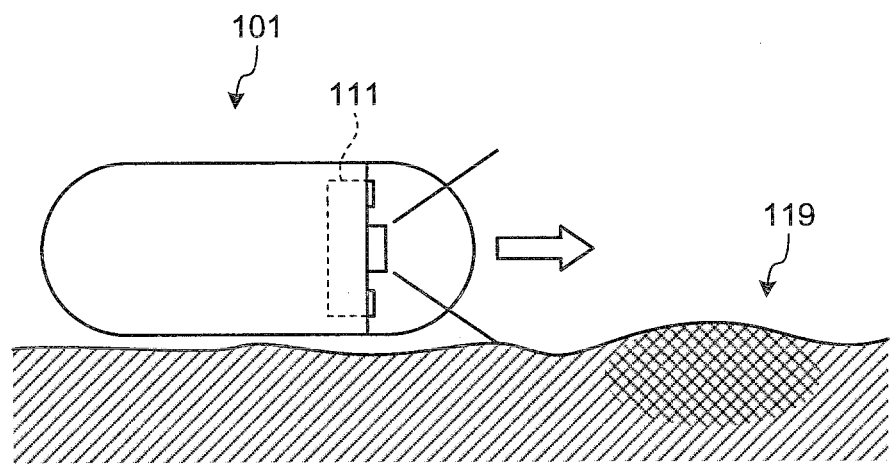
FIGS. 31A and 31B are schematic diagrams in which the capsule medical apparatus inside the subject approaches (FIG. 31A) and reaches (FIG. 31B) an affected area.
Figure 31B:
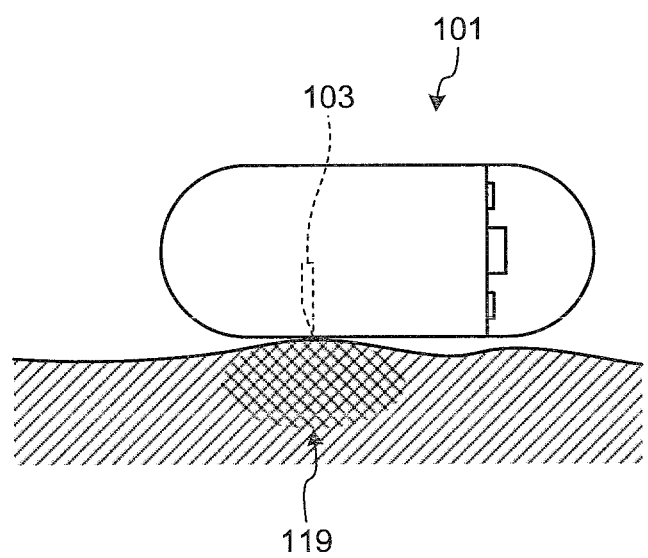
Figure 33A:
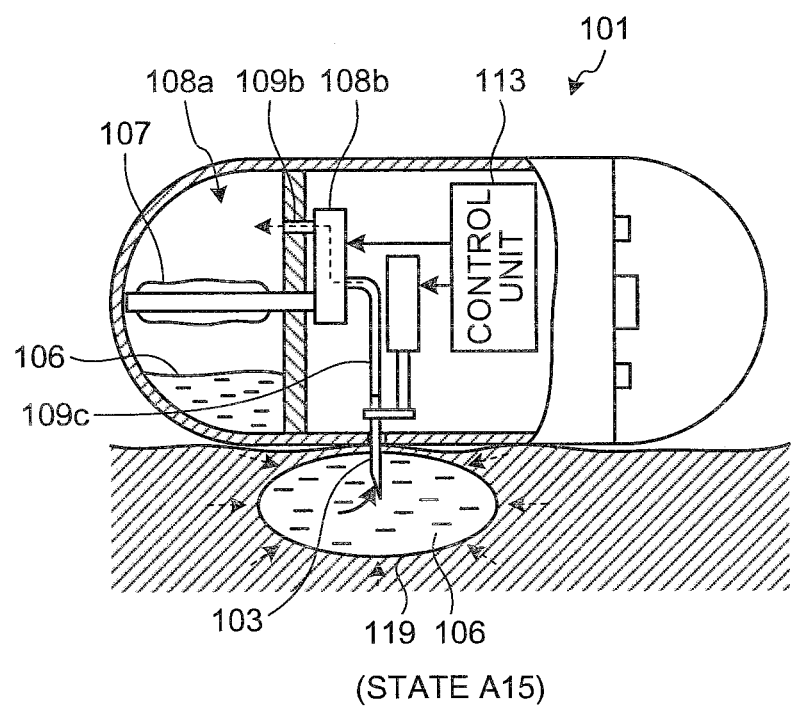
FIGS. 33A and 33B are schematic diagrams in which the capsule medical apparatus inside the subject suppresses an increase in pressure of the drug solution inside the affected area and stores the injection needle.
Figure 33B:
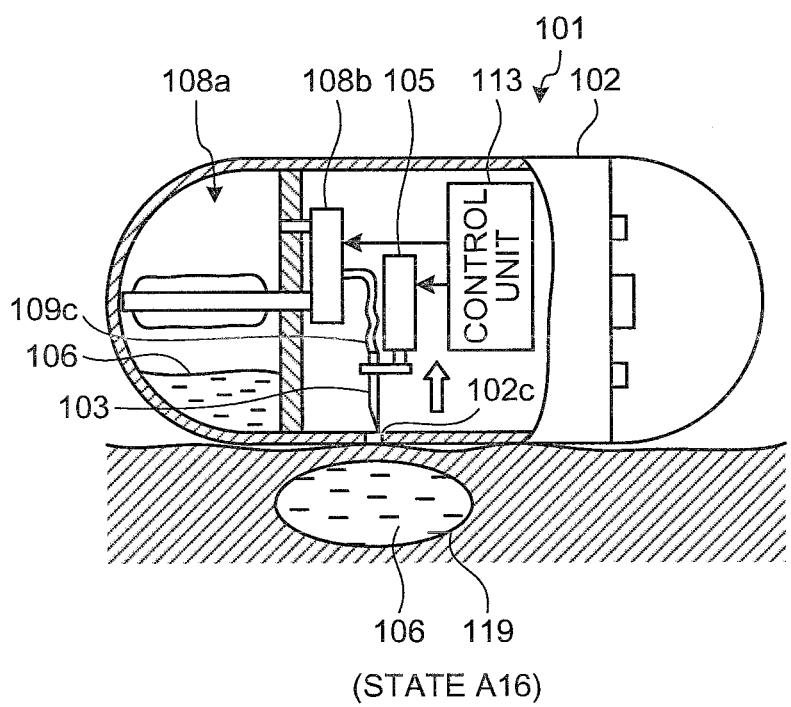

An operation of the capsule medical apparatus 101 according to the sixth embodiment of the present invention is described below in detail. As an example of the operation, the capsule medical apparatus 101 injects a drug solution into an affected area, which is an example of an internal region of interest, inside a subject. FIGS. 31A and 31B are schematic diagrams in which the capsule medical apparatus inside the subject approaches (FIG. 31A) and reaches (FIG. 31B) the affected area. FIG. 33A and FIG. 33B are schematic diagrams in which the capsule medical apparatus inside the subject suppresses an increase in pressure of the drug solution inside the affected area and stores the injection needle.

As described, the capsule medical apparatus 101 is swallowed and introduced into the organs of the subject, e.g., a patient. The capsule medical apparatus 101 inside the subject captures in-vivo images of the subject and wirelessly transmits the in-vivo images in sequence while moving through the digestive organs due to the peristalsis or the like. As shown in FIG. 31A, the capsule medical apparatus 101 eventually approaches an affected area 119 (State A11). The capsule medical apparatus 101 wirelessly transmits the in-vivo images captured by the imaging unit 111 to the external apparatus that is located outside the subject. The external apparatus displays the in-vivo images received from the capsule medical apparatus 101 on a display. Users, such as doctors and nurses, view information displayed by the external apparatus to confirm that the capsule medical apparatus 101 inside the subject has approached the affected area 119.

As shown in FIG. 31B, the capsule medical apparatus 101 near the affected area 119 reaches the affected area 119 due to the peristalsis or the like and adjusts the injection needle 103 to hit the affected area 119 (State A12). The users view the information displayed by the external apparatus to confirm that the capsule medical apparatus 101 inside the subject has reached the affected area 119.

The external apparatus generates a control signal for the capsule medical apparatus 101 based on commands from users and wirelessly transmits the generated control signal to the capsule medical apparatus 101 inside the subject. The capsule medical apparatus 101 inside the subject receives the control signal from the external apparatus via the transmitting unit 112 described above. Based on the received control signal, the capsule medical apparatus 101 performs a series of operations that are performed during a period time between when the injection needle 103 punctures the affected area 119 and when the drug solution 106 is injected into the affected area 119.

Figure 32A:
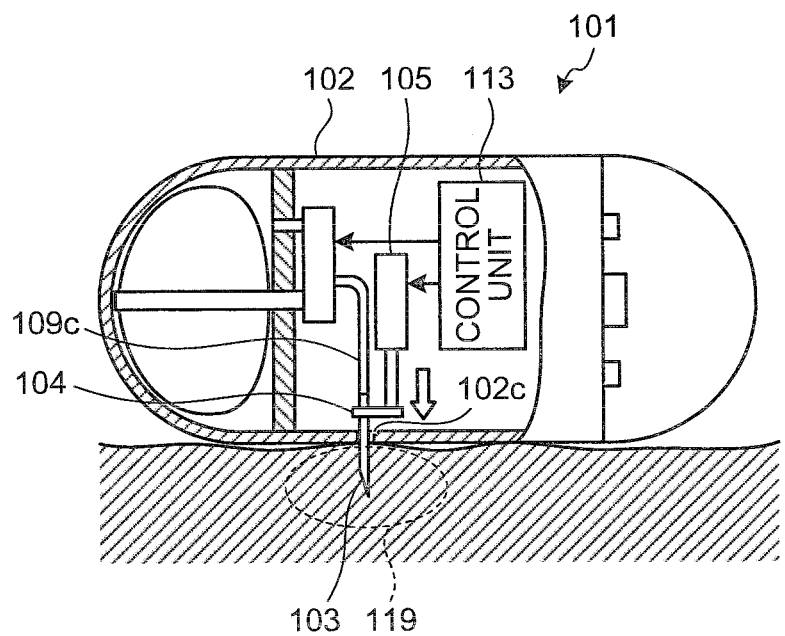
FIGS. 32A and 32B are schematic diagrams in which the capsule medical apparatus inside the subject injects a drug solution into the affected area.

In the capsule medical apparatus 101, the control unit 113 controls the driving unit 105 so that the injection needle 103 protrudes from the capsule casing 102 according to the above-described control signal from the external apparatus. Firstly, the driving unit 105 moves the supporter 104 toward the opening 102c. As shown in FIG. 32A, the injection needle 103 supported by the supporter 104 moves through the opening 102c and protrudes from the capsule casing 102 to puncture the affected area 119 (State A13). The tube 109c does not hinder the protrusion of the injection needle 103.

When the affected area 119 is punctured by the injection needle 103, the control unit 113 control the tube-path switching valve 108b as the tube-path switching valve 108b starts the discharge operation that discharges the drug solution 106 into the affected area 119 using the discharge balloon 107. The tube-path switching valve 108b switches the state between the discharge balloon 107 and the injection needle 103 to the communicated state so that the discharge balloon 107 and the injection needle 103 are communicated by the communicating tube 109a and the tube 109c. The discharge balloon 8 makes the drug solution 106 flow through the communicating tube 109a, the tube-path switching valve 108b, and the tube 109c to inject the drug solution 106 into the affected area 119 through the injection needle 103 that punctures the affected area 119. After the drug solution 106 is discharged through the injection needle 103 and injected into the affected area 119, the drug solution 106 causes the inside of the affected area 119 to expand as shown in FIG. 32B (State A14).

As described above, the control unit 113 keeps the injection needle 103 remaining in the affected area 119. In a predetermined time after the drug solution 106 starts to be injected into the affected area 119 through the injection needle 103, the control unit 113 controls the tube-switching valve 108b so that the communicated state between the injection needle 103 and the discharge balloon 107 is switched to the communicated state between the injection needle 103 and the suction unit 108a. In this case, the tube-path switching valve 108b releases (blocks) the communicated state between the injection needle 103 and the discharge balloon 107 to the communicated state between the injection needle 103 and the suction unit 108a. The suction unit 108a is thus communicated with the injection needle 103 that has punctured and remains in the affected area 119 by the communicating tube 109b and the tube 109c. As shown in FIG. 33A, the suction unit 108a sucks in a part of the drug solution 106 that is inside the affected area 119 through the injection needle 103 using negative pressure generated by the contraction of the discharge balloon 107. The suction unit 108a suppresses an increase in pressure of the drug solution 106 inside the affected area 119. The suction unit 108a contains the drug solution 106 that is sucked in as described above (State A15).

Figure 32B:
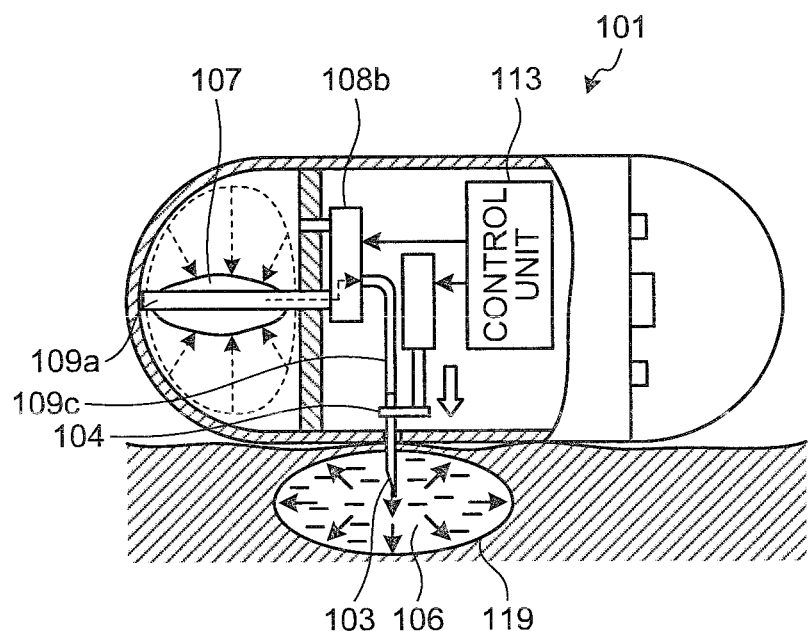

As shown in State A14 in FIG. 32B, the drug solution 106 that has been injected into the affected area 119 causes the inside of the affected area 119 to extend so that the internal space of the affected area 119 expands. The affected area 119, which has expanded due to the drug solution 106, contracts back to an extent that the internal space of the affected area 119 is maintained, even though the affected area 119 does not return to a state before the expansion. Then, some of the drug solution 106 is pushed back to the injection needle 103 by the contraction of the affected area 119 (i.e., a part of the drug solution 106 flows back). The suction unit 108a, using the injection needle 103, sucks in the backflow liquid (the part of the drug solution 106) that is in the affected area 119 and flows back due to the contraction of the affected area 119. The suction unit 108a loosens the affected area 119 that is extended and suppresses the pressure of the drug solution 106 in the affected area 119.

In a predetermined time after the injection needle 103 is communicated with the suction unit 108a as described above (i.e., when the affected area 119 that is extended is loosened), the control unit 113 controls the tube-path switching valve 108b so that a state of the communication is switched to the blocked state described above. The tube-path switching valve 108b blocks both the communication between the injection needle 103 and the discharge balloon 107 and the communication between the injection needle 103 and the suction unit 108a. When the tube-path switching valve 108b is switched to the blocked state, the control unit 113 controls the driving unit 105 so that the injection needle 103 is stored inside the capsule casing 102. As shown in FIG. 33B, the driving unit 105 moves the supporter 104 away from the opening 102c, pulls out the injection needle 103 from the affected area 119, and stores the injection needle 103 inside the capsule casing 102 (State A16).

At State A16, the affected area 119 contains the drug solution 106 and is loosened by the suction unit 108a. The affected area 119 that is loosened cannot contract so that the drug solution 106 does not leak from the site of the puncture that is made by the injection needle 103 even after the injection needle 103 is pulled out.

The amount of the drug solution 106 that the suction unit 108a sucks in is substantially the same as the amount of the liquid that flows back due to the extended affected area 119. The required amount of the drug solution 106 for curing the affected area 119 is maintained. The control unit 113 described above controls the instant when the tube-path switching valve 108b switches the state of communication so as to control the amount of the drug solution 106 that the suction unit 108a sucks in. Thus, the required amount of the drug solution 106 is discharged (injected) into the affected area 119 using the discharge balloon 107.

As described above, in the sixth embodiment, the tube-path switching valve switches to one of the states: the communicated state between the injection needle and the discharge balloon; the communicated state between the injection needle and the suction unit; and the blocked state in which the both of the communicated states are blocked. When the tube-path switching valve switches to the communicated state between the injection needle and the discharge balloon, the discharge balloon injects the drug solution into the internal region of the subject through the injection needle. When the tube-path switching valve switches to the communicated state between the injection needle and the suction unit, the suction unit sucks in the backflow liquid from the internal region through the injection needle that has punctured and remains in the internal region so that the increase in pressure of the drug solution inside the internal region is suppressed. The inside of the internal region that is extended due to the injection of the drug solution is loosened so that the internal region that is extended cannot contract. At the same time, the required amount of the drug solution that is injected into the internal region remains in the inside of the internal region. As a result, using the capsule medical apparatus, the drug solution does not leak from the internal region even after the injection needle is pulled out from the internal region into which the drug solution has been injected.

With the capsule medical apparatus according to the present invention, the drug solution that is injected into an internal region of interest, e.g., an affected area, inside the subject does not leak from the site of the puncture that is made in the internal region of interest. Therefore, the drug solution does not spread over internal regions other than the internal region of interest (i.e., does not spread over unintended internal regions) and does not have unintended effects on those internal regions. Furthermore, when the drug solution is a colored liquid, the capsule medical apparatus has an additional advantage of preventing the colored liquid from leaking from the internal region to be attached to the outer surface of the capsule medical apparatus and impairing the field of view (imaging field) of the capsule medical apparatus.

A seventh embodiment of the present invention is described. In the sixth embodiment described above, the drug solution 106 is injected into the internal region using the injection needle 103 that punctures the internal region, and the suction unit 108a sucks in the backflow drug solution (of the drug solution 106) that flows back from the inside due to the contraction of the extended internal region. In contrast, in the seventh embodiment, the backflow drug solution that flows back due to the contraction of the extended internal region is retrieved into the capsule casing through the injection needle.

Figure 34:
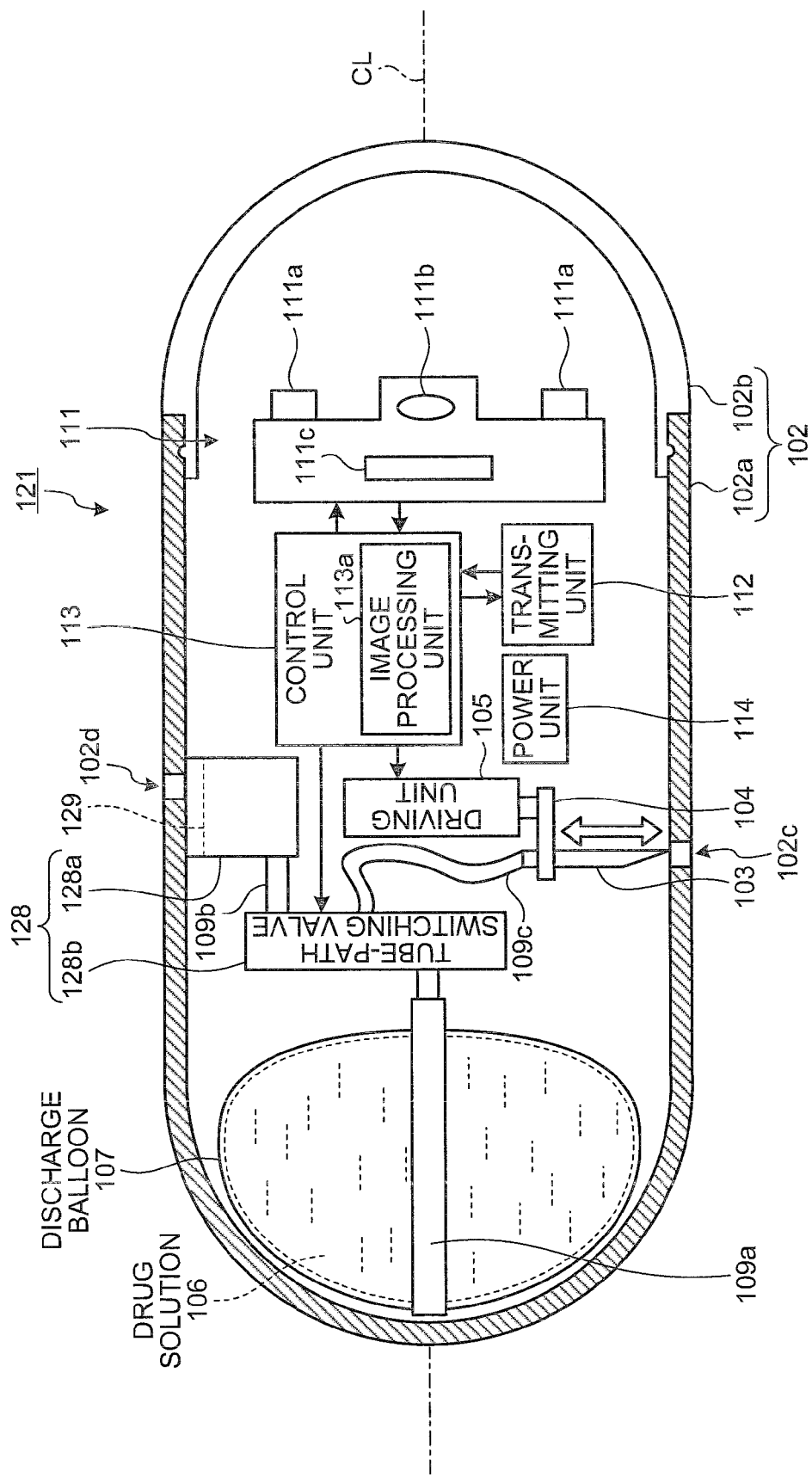
FIG. 34 is a schematic diagram of an exemplary configuration of a capsule medical apparatus according to a seventh embodiment of the present invention.

FIG. 34 is a schematic diagram of an exemplary configuration of the capsule medical apparatus according to the seventh embodiment. As shown in FIG. 34, a capsule medical apparatus 121 according to the seventh embodiment includes a pressure suppressing unit 128 instead of the pressure suppressing unit 108 of the capsule medical apparatus 101 according to the sixth embodiment described above. The pressure suppressing unit 128 includes a drug-solution retrieval unit 128a and a tube-path switching valve 128b instead of the suction unit 108a and the tube-path switching valve 108b. The capsule medical apparatus 121 does not include the wall part 110 that constructs the suction unit 108a. In the seventh embodiment, the communicating tube 109b is communicated with the tube-path switching valve 128b and the drug-solution retrieval unit 128a. There is an opening 102d in the cylinder-shaped container 102a of the capsule casing 102 at a position corresponding to the drug-solution retrieval unit 128a. Other configurations are the same as those of the sixth embodiment, and same numerals are attached to same components.

The pressure suppressing unit 128 suppresses, using the injection needle 103, an increase in pressure of a liquid injected into an internal region of a subject. The pressure suppressing unit 128 includes the drug-solution retrieval unit 128a and the tube-path switching valve 128b. The pressure suppressing unit 128 suppresses, using the injection needle 103 that has punctured the internal region and remains in the internal region, an increase in pressure of the drug solution 106 that is injected into the internal region through the injection needle 103.

The drug-solution retrieval unit 128a retrieves, using the injection needle, a part of the liquid that is injected into the internal region of the subject and that flows back from the internal region. The drug-solution retrieval unit 128a is a box-shaped or a cylinder-shaped component that has a bottom end and an open end. The drug-solution retrieval unit 128a is fixed to the inner wall of the cylinder-shaped container 102a in a manner such that the opening 102d in the cylinder-shaped container 102a is within the open end. The drug-solution retrieval unit 128a is communicated with the tube-path switching valve 128b by the communicating tube 109b. The drug-solution retrieval unit 128a is communicated with the injection needle 103 by the communicating tube 109, the tube 109c, and the like depending on the state of the tube-path switching valve 128b. The drug-solution retrieval unit 128a includes a transmission film 129 near the open end thereof (i.e., near the opening 102d in the cylinder-shaped container 102a). The transmission film 129 is a film that has a porous structure. The transmission film 129 does not allow a liquid to transmit but allows gas to transmit. When the drug-solution retrieval unit 128a is communicated with the injection needle 103, the drug-solution retrieval unit 128a retrieves the backflow liquid that flows back due to the contraction of the extended internal region (i.e., retrieves the part of the drug solution 106 that is injected into the internal region). The drug-solution retrieval unit 128a allows only gas, e.g., air, to transmit to the outside through the opening 102d using the transmission filter 129. The drug-solution retrieval unit 128a retrieves the backflow liquid from the internal region through the injection needle 103. When the communication between the drug-solution retrieval unit 128a and the injection needle 103 is blocked by the tube-path switching valve 128b, the backflow liquid that has been retrieved is sealed inside the drug-solution retrieval unit 128a (i.e., the part of the drug solution 106 is sealed inside the drug solution retrieval unit 128a). Thus, the backflow liquid that has been retrieved is contained the drug-solution retrieval unit 128a and does not leak therefrom.

In the tube-path switching valve 128b, the opening of the tube path 115b shown in FIG. 29 is directed to the drug-solution retrieval unit 128a. Other than that configuration, the tube-path switching valve 128b has the same structure as the tube-path switching valve 108b of the capsule medical apparatus 101 according to the sixth embodiment described above. The tube-path switching valve 128b is communicated with the drug-solution retrieval unit 128a by the communicating tube 109b that is connected to the opening of the tube path 115b. Other than that, the tube-path switching valve 128b has the same functions as those of the tube-path switching valve 108b of the capsule medical apparatus 101 according to the sixth embodiment. Under the control of the control unit 113, the tube-path switching valve 128b switches to one of the states: the communicated state between the injection needle 103 and the discharge balloon 107; the communicated state between the injection needle 103 and the drug-solution retrieval unit 128a; and the blocked state in which both of the communicated states are blocked. When the tube-path switching valve 128b switches its state from the communicated state between the injection needle 103 and the drug-solution retrieval unit 128a to the communicated state between the injection needle 103 and the discharge balloon 107, the injection needle 103 is communicated with the discharge balloon 107 while the communication between the injection needle 103 and the drug-solution retrieval unit 128a is blocked. When the tube-path switching valve 128b switches its state from the communicated state between the injection needle 103 and the discharge balloon 107 to the communicated state between the injection needle 103 and the drug-solution retrieval unit 128a, the injection needle 103 is communicated with the drug-solution retrieval unit 128a while the communication between the injection needle 103 and the discharge balloon 107 is blocked.

In the capsule medical apparatus 21 according to the seventh embodiment, the control unit 113 controls communicated state between the injection needle 103 and the drug-solution retrieval unit 128a instead of the communicated state between the injection needle 103 and the suction unit 108a described above. The communicated state is controlled by switching the tube paths in the tube-path switching valve 128b. The control unit 113 can communicate the injection needle 103 with the drug-solution retrieval unit 128a similarly to the sixth embodiment in which the injection needle 103 is communicated with the suction unit 108a. The control unit 113 blocks the communication between the injection needle 103 and the drug-solution retrieval unit 128a similarly to the sixth embodiment in which the communication between the injection needle 103 and the suction unit 108 is ended (blocked).

Figure 35:
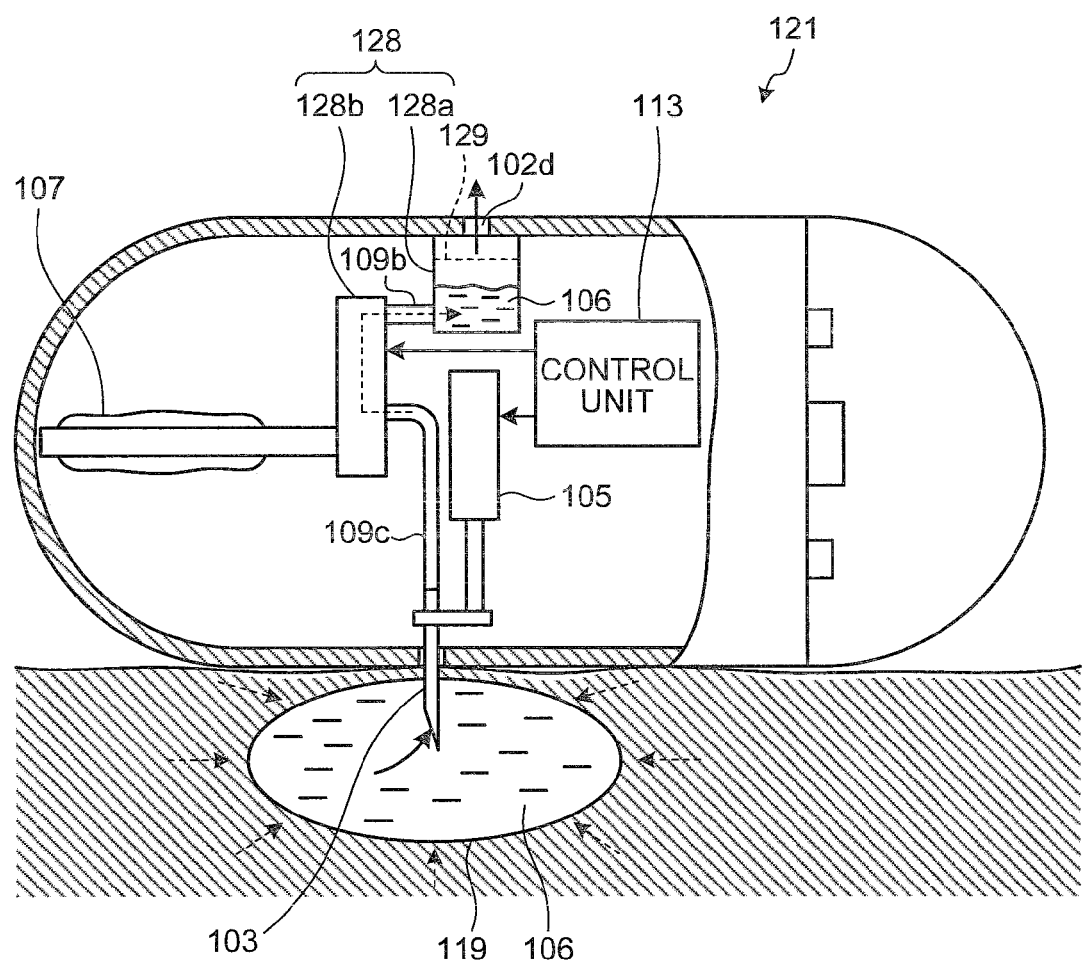
FIG. 35 is a schematic diagram in which the capsule medical apparatus inside the subject suppresses an increase in pressure of the drug solution inside the affected area.

An operation of the capsule medical apparatus 121 according to the seventh embodiment of the present invention is described below. As an example of the operation, the capsule medical apparatus 121 injects a drug solution into an affected area, which is an example of an internal region of interest, inside a subject. FIG. 35 is a schematic diagram in which the capsule medical apparatus inside the subject suppresses an increase in pressure of the drug solution inside the affected area. Other than the operation for suppressing an increase in pressure of the drug solution inside the affected area, the capsule medical apparatus 121 performs the same operations as those of the capsule medical apparatus 101. The operation of the capsule medical apparatus 121 for suppressing an increase in pressure of the drug solution inside the affected area is described below, and other operations are omitted.

The drug solution 106 that is injected into the affected area 119 causes the inside of the affected area 119 to extend so that the internal space of the affected area 119 expands, similarly to the sixth embodiment. The affected area 119 extended by the drug solution 106 contracts to an extent that the internal space is steadily maintained but does not return to its state before the extension. A part of the drug solution 106 inside the affected area 119 is pushed back to the injection needle 103 by the contraction of the affected area 119. The part of the drug solution 106 then flows back through the injection needle 103, the tube 109c, the tube-path switching valve 128b, and the communicating tube 109b in sequence into the drug-solution retrieval unit 128a.

The drug-solution retrieval unit 128a receives the backflow liquid (the part of the drug solution 106) that has flowed back through the injection needle 103 from the affected area 119. At the same time, the drug-solution retrieval unit 128a discharges internal gas through the opening 102d using the transmission film 129. The drug-solution retrieval unit 128a keep receiving the backflow liquid from the affected area 119 until the affected area 119 stops contracting so that the inside of the extended affected area 119 is loosened, and the increase in pressure of the drug solution 106 inside the affected area 119 is suppressed.

In a predetermined time after the injection needle starts to be communicated with the drug-solution retrieval unit 128a (i.e., when the inside of the extended affected area 119 is loosened enough), the control unit 113 controls the tube-path switching valve 128b so that the state is switched to the blocked state described above. Thus, the tube-path switching valve 128b blocks both the communicated state between the injection needle 103 and the discharge balloon 107 and the communicated state between the injection needle 103 and the drug-solution retrieval unit 128a. With the tube-path switching valve 128b being at the blocked state, the drug-solution retrieval unit 128a seals therein the drug solution 106 (backflow liquid) that has been retrieved from the affected area 119. Because the drug solution 106 that has been retrieved from the affected area 119 cannot transmit through the transmission film 129, the drug solution 106 does not leak from the opening 102d.

The affected area 119 is loosened enough while the affected area 119 contains the drug solution 106 that has been injected. The affected area 119 that is loosened cannot contract so that the drug solution 106 does not leak from the site of the puncture that is made by the injection needle 103 even after the injection needle 103 is pulled out.

The amount of the drug solution 106 that the drug-solution retrieval unit 128a retrieves is substantially the same amount as the amount of the liquid that flows back due to the extended affected area 119. The required amount of the drug solution 106 for curing the affected area 119 remains in the affected area 119. The control unit 113 can control the instant when the tube-path switching valve 128b switches its state depending on the amount of the drug solution 106 retrieved by the drug-solution retrieval unit 128a so that the required amount of the drug solution 106 is discharged (injected) into the affected area 119 using the discharge balloon 107.

As described above, the tube-path switching valve switches to one of the states: the communicated state between the injection needle and the discharge balloon; the communicated state between the injection needle and the drug-solution retrieval unit; and the blocked state in which both of the communicated states are blocked. When the injection needle is communicated with the drug-solution retrieval unit by the tube-path switching valve, the drug-solution retrieval unit, using the injection needle that has punctured and remains in the internal region, retrieves the backflow liquid that flows back from the internal region so that the increase in pressure of the drug solution inside the internal region is suppressed. Other configurations are the same as those of the sixth embodiment. Thus, the capsule medical apparatus can provide the same operational effects as those of the sixth embodiment.

In the seventh embodiment of the present invention, the drug-solution retrieval unit retrieves the drug solution that flows back due to the contraction of the extended internal region, without using the negative pressure due to the contraction of the discharge balloon. Thus, the drug-solution retrieval unit is not necessarily arranged in a sealed space that contains the discharge balloon. The drug-solution retrieval unit may be arranged in any position in the capsule casing as long as the drug-solution retrieval unit can be communicated with the tube-path switching valve by the communicating tube. As a result, the inner components of the capsule casing can be configured more freely, whereby the capsule medical apparatus that can provide the same operational effects as those of the sixth embodiment can be produced more easily.

An eighth embodiment of the present invention is described. In the seventh embodiment described above, the backflow drug solution that flows back due to the contraction of the extended internal region is retrieved from the injection needle into the capsule casing so that the increase in pressure of the drug solution inside the internal region is suppressed. In contrast, in the eighth embodiment, gas is injected into and discharged from the internal region through the injection needle for controlling the injection of the drug solution. After the internal region is extended and then loosened, the drug solution is injected into the internal region that is loosened so that the increase in pressure of the injected drug solution is suppressed.

Figure 36:
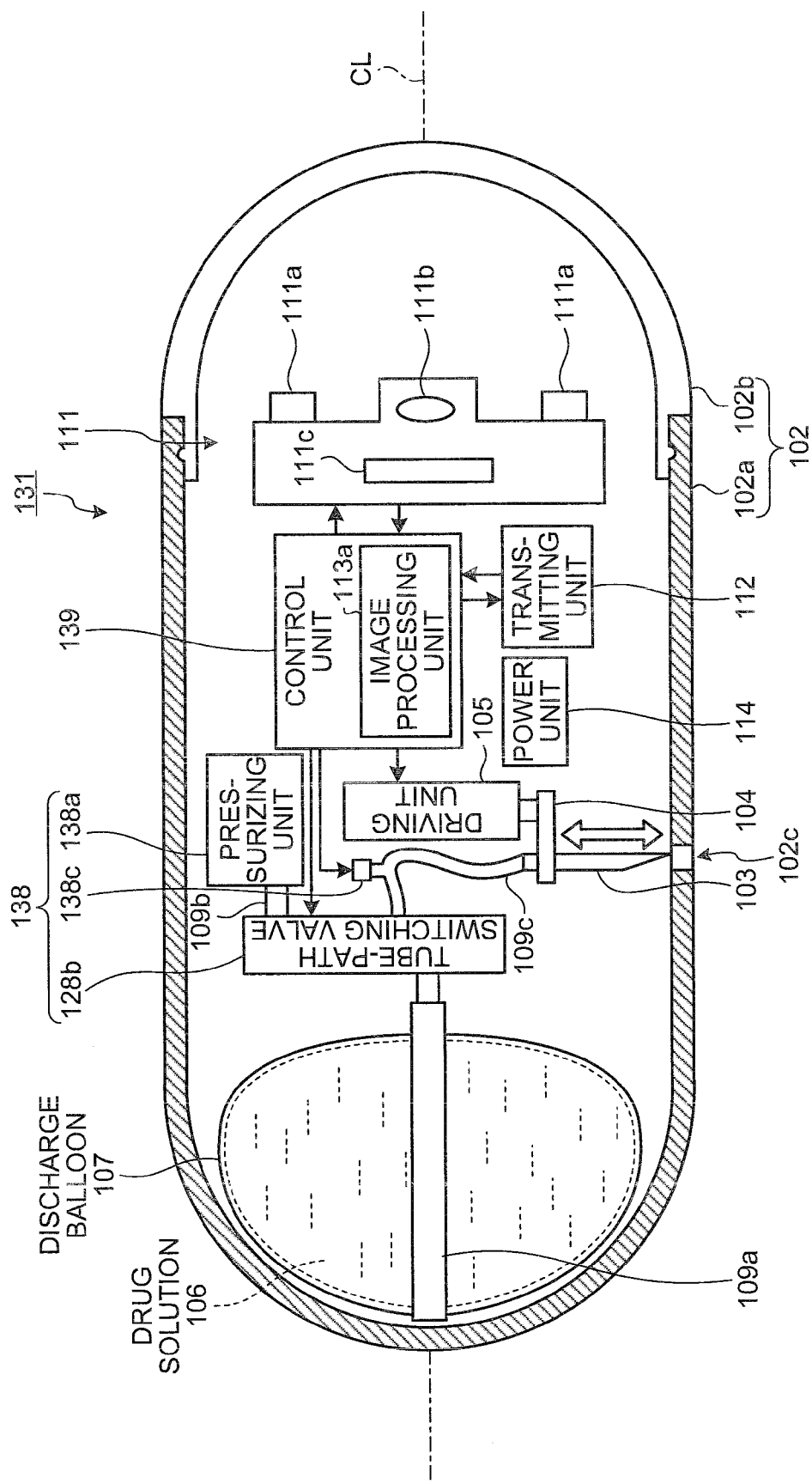
FIG. 36 is a schematic diagram of an exemplary configuration of a capsule medical apparatus according to an eighth embodiment of the present invention.

FIG. 36 is a schematic diagram of a capsule medical apparatus according to the eighth embodiment of the present invention. AS shown in FIG. 36, a capsule medical apparatus 131 according to the eighth embodiment, includes a pressure suppressing unit 138 and a control unit 139 instead of the pressure suppressing unit 128 and the control unit 113 of the capsule medical apparatus 121 according to the seventh embodiment described above. The pressure suppressing unit 138 includes a pressurizing unit 138a, instead of the drug-solution retrieval unit 128a, and further includes an air discharge unit 138c. In the eighth embodiment, the air discharge unit 138c is communicated with the tube 109c. There is no opening 102c in the cylinder-shaped container 102a of the capsule casing 102, which is different from the capsule casing according to the seventh embodiment. Other configurations are the same as those of the seventh embodiment, and same numerals are attached to same components.

The pressure suppressing unit 138, using the injection needle 103, suppresses an increase in pressure of the liquid that is injected into the internal region of the subject. The pressure suppressing unit 138 includes the tube-path switching valve 128b, the pressurizing unit 138a, and the air discharge unit 138c. The pressure suppressing unit 138, using the injection needle 103 that has punctured and remains in the internal region, suppresses the increase in pressure of the drug solution 106 that remains inside the internal region punctured by the injection needle 103.

Before the drug solution 106 or the like is injected into the internal region of the subject, the pressurizing unit 138a pressurizes the inside of the internal region to cause the inside the internal region to extend. The pressurizing unit 138a contains a compressed gas that is harmless to a human, e.g., air, carbon dioxide. The pressurizing unit 138a is communicated with the tube-path switching valve 128b by the communicating tube 109b. Depending on the state of the tube-path switching valve 128b, the pressurizing unit 138a is communicated with the injection needle 103 by the communicating tube 109b, the tube 109c, and the like. When the pressurizing unit 138a is communicated with the injection needle 103 that has punctured and remains in the internal region, the pressurizing unit 139a pressurizes the inside of the internal region by injecting the gas to cause the inside of the internal region to extend. When the communication between the pressurizing unit 138a and the injection needle 103 is blocked due to the switching of the state of the tube-path switching valve 128b, the pressurizing unit 138a stops injecting the gas into the internal region.

The air discharge unit 138c discharges a part of the internal gas of the internal region, which has extended due to the pressurization of the pressurizing unit 138a, using the injection needle 103. The air discharge unit 138c can include an electromagnet or the like and is communicated with the tube 109c. The air discharge unit 138c is communicated with the injection needle 103 by the tube 109c. The air discharge unit 138c is actuated by the control unit 139. The air discharge unit 138c discharges a part of the internal gas using the injection needle 103 that has punctured and remains in the internal region so that the inside of the internal region is loosened. The internal gas of the internal region that has been discharged by the air discharge unit 138c may flow into the inside or the outside of the capsule casing 102.

The tube-path switching valve 128b is communicated with the pressurizing unit 138a instead of the drug-solution retrieval unit 128a. Other than that configuration, the tube-path switching valve 128b is configured similarly to the seventh embodiment. In the eighth embodiment, under the control of the control unit 139, the tube-path switching valve 128b switches to one of the states: the communicated state between the injection needle 103 and the discharge balloon 107; the communicated state between the injection needle 103 and the pressurizing unit 138a; and the blocked state in which both of the communicated states are blocked. When the tube-path switching valve 128b switches its state from the communicated state injection needle 103 and the pressurizing unit 138a to the communicated state between the injection needle 103 and the discharge balloon 107, the tube-path switching valve 128b communicates the injection needle 103 with the discharge balloon 107 while the communication between the injection needle 103 and the pressurizing unit 138a is blocked. When the tube-path switching valve 128b switches its state from the communicated state between the injection needle 103 and the discharge balloon 107 to the communicated state injection needle 103 and the pressurizing unit 138a, the tube-path switching valve 128b communicates the injection needle 103 with the pressurizing unit 138a while the communication between the injection needle 103 and the discharge balloon 107 is blocked.

According to the control signal that is obtained from the external apparatus using the transmitting unit 112, the control unit 139 controls the driving unit 105 so that the injection needle 103 punctures the internal region of the subject, and the control unit 139 also controls the tube-path switching valve 128b so that the state is switched to the communicated state between the injection needle 103 and the pressurizing unit 138a. In a predetermined time after the injection needle 103 starts to be communicated with the pressurizing unit 138a, the control unit 139 controls the tube-path switching valve 128b so that the communication between the injection needle 103 and the pressurizing unit 138a ends (is blocked). At the same time, the control unit 139 controls the air discharge unit 138c so that the internal gas of the internal region is discharged through the injection needle 103. In a predetermined time after the air discharge unit 138c starts the discharge operation, the control unit 139 controls the air discharge unit 138c so that its discharge operation is stopped. At the same time, the control unit 139 controls the tube-path switching valve 128b as the tube-path switching valve 128b switches its state to the communicated state between the injection needle 103 and the discharge balloon 107. In a predetermined time after the discharge operation that discharges the drug solution 106 using the discharge balloon 107 is started, the control unit 139 controls the tube-path switching valve 128b so that the state is switched to the blocked state described above. The control unit 139 then controls the driving unit 105 so that the injection needle 103 is pulled out from the internal region and the injection needle 103 is then stored inside the capsule casing 102. Other than those control functions above, the control unit 139 has the same functions as those of the control unit 113 of the capsule medical apparatus 121 according to the seventh embodiment described above.

Figure 37:
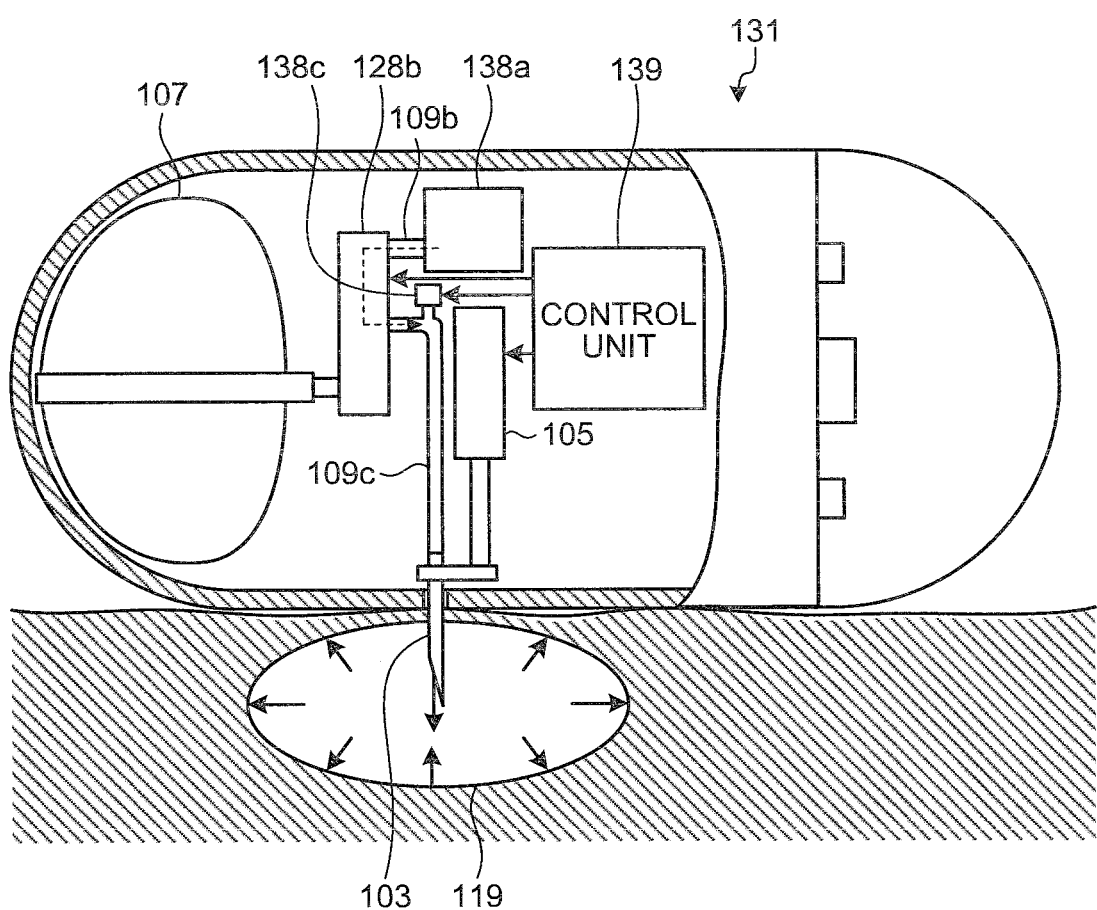
FIG. 37 is a schematic diagram in which the capsule medical apparatus inside the subject pressurizes and extends the inside of an affected area.
Figure 38:
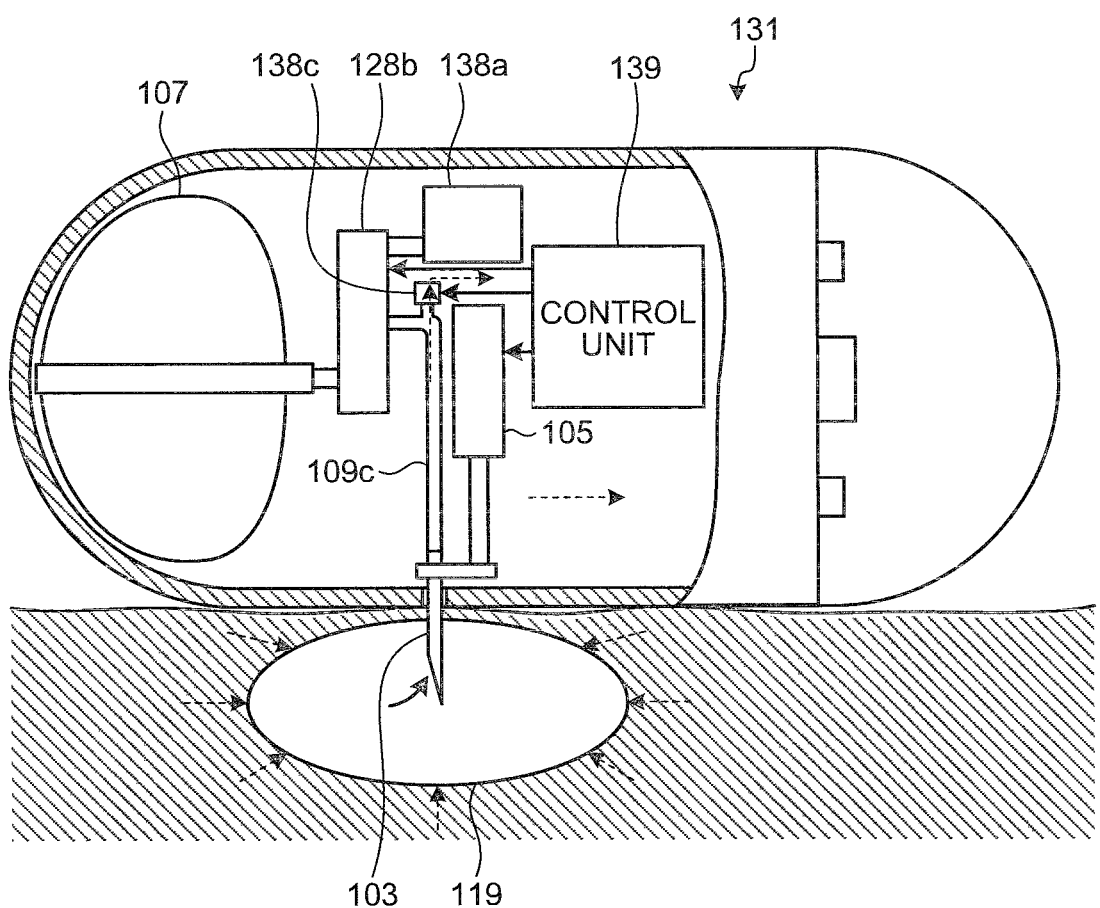
FIG. 38 is a schematic diagram in which the capsule medical apparatus inside the subject loosens the inside of the affected area by discharging gas.

An operation of the capsule medical apparatus 131 according to the eighth embodiment of the present invention is described below. As an example of the operation, the capsule medical apparatus 131 injects a drug solution into an affected area, which is an example of an internal region of interest, inside a subject. FIG. 37 is a schematic diagram in which the capsule medical apparatus inside the subject pressurizes and extends the inside of the affected area. FIG. 38 is a schematic diagram in which the capsule medical apparatus loosens the inside of the affected area by discharging the gas. FIG. 39 is a schematic diagram in which the capsule medical apparatus inside the subject injects the drug solution into the affected area after discharging the gas. Other than the operations for suppressing an increase in pressure of the drug solution in the affected area and for injecting the drug solution into the affected area, the capsule medical apparatus 131 according to the eighth embodiment performs the same operations as those of the capsule medical apparatus 121 according to the seventh embodiment. Described below are the operations of the capsule medical apparatus 131 for suppressing an increase in pressure of the drug solution in the affected area and for injecting the drug solution into the affected area.

As shown in FIG. 37, when the capsule medical apparatus 131, using the driving unit 105, punctures the affected area 119 inside the subject with the injection needle 103, the control unit 139 controls the tube-path switching valve 128b so that the state is switched to the communicated state between the injection needle 103 and the pressurizing unit 138a. In this case, the tube-path switching valve 128b communicates the injection needle 103 with the pressurizing unit 138a while the communication between the injection needle 103 and the discharge balloon 107 is blocked. The pressurizing unit 138a is thus communicated with the injection needle 103 that has punctured and remains in the affected area 119 by the tube-path switching valve 128b, the tube 109c, and the like. The pressurizing unit 138a injects the gas into the affected area 119 through the injection needle 103 that remains in the internal region. By injecting (pushing) the gas into the affected area 119 as described above, the pressurizing unit 138a pressurizes the inside of the affected area 119 and causes the inside of the affected area 119 to extend.

The control unit 139 keeps the injection needle 103 remaining in the affected area 119. In a predetermined time after the pressurizing unit 138a starts to inject the compressed gas into the affected area 119 through the injection needle 103 (i.e., when the inside of the affected area 119 is extended enough by the pressurizing unit 138a), the control unit 139 controls the tube-path switching valve 128b so that the communicated state between the injection needle 103 and the pressurizing unit 138a is blocked. At the same time, the control unit 139 controls the air discharge unit 138c so that the internal gas of the affected area 119 is discharged. Then, the tube-path switching valve 128b switches its state to the blocked state so that the pressurizing unit 138a stops injecting the gas into the affected area 119. The air discharge unit 138c discharges the internal gas of the affected area 119 through the tube 109c and the injection needle 103 so that the inside of the affected area 119 is depressurized.

The affected area 119 that has been extended due to the pressurization (that pushes and injects gas) by the pressurizing unit 138a contracts to an extent that the internal space is maintained but does not return to its state before the extension. The internal gas of the affected area 119 flows back to the injection needle 103 due to the contraction of the affected area 119. As shown in FIG. 38, the internal gas flows through the injection needle 103 and the tube 109c sequentially. The air discharge unit 138c discharges the internal gas of the affected area 119 using the contraction of the affected area 119. The air discharge unit 138c continuously discharges the internal gas of the affected area 119 until the affected area dose not contract any more. The air discharge unit 138c thus loosens the inside of the extended affected area 119.

The control unit 139 keeps the injection needle 103 remaining in the affected area 119. In a predetermined time after the internal gas of the affected area 119 starts to be discharged through the injection needle 103 (i.e., when the inside of the extended affected area 119 is loosened by the air discharge unit 138c), the control unit 139 controls the air discharge unit 138c so that causing the gas to be discharged is stopped. At the same time, the control unit 139 controls the tube-path switching valve 128b so that the state is switched to the communicated state between the injection needle 103 and the discharge balloon 107. The tube-path switching valve 128b communicates the injection needle 103 with the discharge balloon 107 while the communication between the injection needle 103 and the pressurizing unit 138a is blocked. As shown in FIG. 39, the discharge balloon 107 is communicated with the injection needle 103 by the communicating tube 109a, the tube-path switching valve 128b, and the tube 109c. The discharge balloon 107 injects the drug solution 106 into the affected area 119 through the injection needle 103.

The control unit 139 controls the amount of the drug solution 106 that is injected into the affected area 119 so that the drug solution 106 does not cause the inside of the affected area 119 to extend. In a predetermined time after the injection needle 103 starts to be communicated with the discharge balloon 107, the control unit 139 controls the tube-path switching valve 128b so that the communicated state between the injection needle 103 and the discharge balloon 107 is blocked. The control unit 139 can control the amount of the drug solution 106 that is injected using the discharge balloon 107 by controlling the tube-path switching valve 128b so that the drug solution 106 is injected by a desired amount. The amount of the drug solution 106 that is injected does not cause the inside of the affected area 119, which is loosened as described above, to extend again. For example, the drug solution 106 is injected by half the volume of the affected area 119. The amount of the drug solution 106 that is injected into the affected area 119 does not cause the inside of the affected area 119 to extend again and remains in the loosened affected area 119. The drug solution 106 that remains in the affected area 119 is not affected by the contraction of the affected area 119. As a result, the increase in pressure of the drug solution 106 in the affected area 119 is suppressed.

The affected area 119 does not contract because the affected area 119 is loosened due to the discharging of the internal gas. Therefore, the drug solution 106 does not leak from the site of the puncture that is made by the injection needle 103.

As described above, in the eighth embodiment, the tube-path switching valve switches to one of the states: the communicated state between the injection needle and the discharge balloon; the communicated state between the injection needle and the pressurizing unit; and the blocked state in which both of the communicated states are blocked. The pressurizing unit causes the inside of the affected area to extend using the injection needle that remains in the internal region and that is communicated with the pressurizing unit by the tube-path switching valve. The air discharge unit causes the internal gas of the internal region to be discharged through the injection needle so that the inside of the internal region is loosened. The discharge balloon then injects the drug solution into the internal region by an amount that does not cause the internal region to extend again. Other configurations are the same as those of the seventh embodiment. Thus, the capsule medical apparatus can provide the same operational effects as those of the seventh embodiment described above. Furthermore, the capsule medical apparatus injects only a minimum amount of the drug solution into the internal region. Therefore, the capsule medical apparatus can be further downsized.

In the sixth, seventh, and eighth embodiments described above, the capsule medical apparatus injects a drug solution that affects an internal region of a subject. Not limited to this, the capsule medical apparatus may inject any liquid into the internal region of the subject. In this case, the liquid that is injected into the internal region by the capsule medical apparatus may be transparent or colored (e.g., liquid for marking).

In the eighth embodiment, the compressed gas is filled in the pressurizing unit 138a, and the pressurizing unit 138a pushes and injects the compressed gas into the internal region. Not limited to this, the gas that is injected by the pressurizing unit 138a into the internal region may be gas generated by the a foaming agent. In this case, the pressurizing unit 138a contains a foaming agent (e.g., a sodium acid carbonate) and a liquid (e.g., water). When the pressurizing unit 138a is communicated with the injection needle 103 by the tube-path switching valve 128b, the foaming agent and the liquid are mixed to generate gas, which is then injected into the internal region through the injection needle 103.

In the eighth embodiment, the air discharge unit 138c causes the internal gas of the internal region to be discharged using the contraction of the extended internal region. Not limited to this, the air discharge unit 138c can be a suction pump or the like that causes the internal gas of the extended internal region to be discharged by sucking in the internal gas. In this case, the air discharge unit 138c can cause the gas that flows back due to the contraction of the internal region to be discharged. The air discharge unit 138c can suck in the gas that is injected to extend the inside of the internal region (i.e., the gas that is injected by the pressurizing unit 138a) and thus causes the gas to be discharged.

In the eighth embodiment, after the pressurizing unit 138a pushes and injects the gas into the internal region through the injection needle 103, the air discharge unit 138c causes the internal gas of the extended internal region to be discharged so that the extended internal region is loosened. Not limited to this, after the pressurizing unit 138a pushes and injects the gas into the internal region through the injection needle 103, the injection needle 103 may be pulled out from the extended internal region. Then, the internal gas may be discharged from the site of the puncture, which is made by the injection needle 103, due to the contraction of the internal region so that the extended internal region may be loosened.

In the sixth, seventh, and eighth embodiments described above, single driving unit 105 that is actuated by power protrudes the injection needle 103 from the capsule casing 102, punctures the internal region of the subject with the injection needle 103, and pulls out the injection needle 103 that has punctured the internal region from the internal region. Not limited to this, the capsule medical apparatus may include one driving unit that protrudes the injection needle 103 from the capsule casing 102 and another driving unit that performs the puncturing and the pullout of the injection needle 103 from the internal region. In this case, the driving unit that protrudes the injection needle 103 from the capsule casing 102 can be a electric actuator or the like that is actuated by power or may be a magnetic actuator that is actuated by an external magnetic field that is applied from the outside. The driving unit that performs the puncturing and the pullout of the injection needle 103 may be a electric actuator that is actuated by power or may be a magnet that is actuated by an external magnetic field that is applied from the outside.

In the capsule medical apparatus according to the present invention, the needle driving unit protrudes the injection needle from the capsule casing, punctures an internal region with the injection needle, pulls out the injection needle from the internal region, and stores the injection needle inside the capsule casing. The liquid injection unit injects a liquid into the internal region through the injection needle that has punctured and remains in the internal region. The sealing unit seals the puncture hole that is made in the internal region by the injection needle during a period of time between when the liquid injection unit injects the liquid into the internal region and when the needle driving unit pulls out the injection needle from the internal region. Thus, the puncture hole is sealed while the injected liquid, e.g., a drug solution, does not leak from the puncture hole in the internal region. As a result, when the injection needle is pulled out from the internal region into which the drug solution is injected, the drug solution does not leak from the internal region.

In the capsule medical apparatus according to the present invention, the needle driving unit punctures an internal region of the subject with the injection needle and pulls out the injection needle from the internal region. The liquid injection unit injects a liquid into the internal region through the injection needle that has punctured and remains in the internal region. The pressure suppressing unit suppresses an increase in pressure of the liquid in the internal region. Thus, the pressure of the liquid is suppressed and becomes lower than pressure at which the liquid spouts out of the site of the puncture that is made in the internal region by the injection needle. As a result, when the injection needle is pulled out from the internal region into which the drug solution is injected, the drug solution does not leak from the internal region.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:
1. A capsule medical apparatus, comprising:
a needle driving unit that punctures an internal region of interest in a subject with an injection needle and pulls out the injection needle from the internal region of interest;
a liquid injection unit that injects a liquid into the internal region of interest through the injection needle that punctures the internal region of interest; and
a leak prevention unit that prevents the liquid injected into the internal region of interest from leaking from the internal region of interest;

wherein the leak prevention unit comprises a pressure suppressing unit that suppresses an increase in pressure of the liquid remaining inside the internal region of interest;

wherein the pressure suppressing unit comprises:

a suction unit that sucks a backflow liquid that is the liquid injected into the internal region of interest and that then flows back from the internal region of interest through the injection needle, a path for injecting the liquid into the internal region of interest being the same as a path for sucking the backflow liquid; and a communicated-state switching unit that switches its state from a communicated state between the injection needle and the liquid injection unit to a communicated state between the injection needle and the suction unit and vice versa.

2. The capsule medical apparatus according to claim 1, wherein the leak prevention unit is a sealing unit that changes a state of a puncture hole that is made in the in-vivo region of interest by the injection needle into a sealed state during the period of time between when the liquid injection unit injects the liquid into the internal region of interest and when the needle driving unit pulls out the injection needle from the internal region of interest.

3. The capsule medical apparatus according to claim 2, wherein the sealing unit is a needle-diameter changing unit that changes the outer diameter of the injection needle.

4. The capsule medical apparatus according to claim 3, wherein the needle-diameter changing unit is a heating unit that heats the injection needle, which then contracts so that the state of the puncture hole becomes the sealed state.

5. The capsule medical apparatus according to claim 1, wherein the needle driving unit protrudes the injection needle from the capsule casing of the capsule medical apparatus, punctures the internal region of interest of a subject with the injection needle, pulls out the injection needle that punctures the internal region of interest from the internal region of interest, and stores the injection needle inside the capsule casing.

* * * * *